US009638707B2

(12) United States Patent
Spence et al.

(10) Patent No.: US 9,638,707 B2
(45) Date of Patent: May 2, 2017

(54) METHODS OF PROCESSING SAMPLES

(71) Applicant: Argos Therapeutics, Inc., Durham, NC (US)

(72) Inventors: Simon Jonathon Spence, Hawthorn (AU); Richard Alexander Grant, St. Kilda West (AU); Timothy Doyle Peele, Raleigh, NC (US); William Samuel Hunter, Jan Juc (AU); Ashraf F. Abdelmoteleb, Ferntree Gully (AU); David Thomas Kneen, Richmond (AU); Robert Alister Neil, Richmond (AU); Simon Harris, Keysborough (AU)

(73) Assignee: Argos Therapeutics, Inc., Durham, NC (US)

( * ) Notice: Subject to any disclaimer, the term of this patent is extended or adjusted under 35 U.S.C. 154(b) by 0 days.

(21) Appl. No.: 15/357,347

(22) Filed: Nov. 21, 2016

(65) Prior Publication Data

US 2017/0067925 A1    Mar. 9, 2017

Related U.S. Application Data

(60) Continuation of application No. 15/216,128, filed on Jul. 21, 2016, now Pat. No. 9,527,074, which is a
(Continued)

(51) Int. Cl.
*G01N 35/00* (2006.01)
*B01L 3/00* (2006.01)

(52) U.S. Cl.
CPC ........ *G01N 35/0099* (2013.01); *B01L 3/5085* (2013.01); *G01N 35/00732* (2013.01);
(Continued)

(58) Field of Classification Search
CPC .................................................. G01N 35/0099
See application file for complete search history.

(56) References Cited

U.S. PATENT DOCUMENTS

| 4,683,195 A | 7/1987 | Mullis et al. |
| 4,683,202 A | 7/1987 | Mullis |

(Continued)

FOREIGN PATENT DOCUMENTS

| CA | 2 600 828 A1 | 9/2006 |
| WO | WO 97/16561 A1 | 5/1997 |

(Continued)

OTHER PUBLICATIONS

International Search Report and the Written Opinion of the International Searching Authority corresponding to International Patent Application No. PCT/US 07/01170 (dated Jun. 24, 2008).
(Continued)

*Primary Examiner* — Jyoti Nagpaul
(74) *Attorney, Agent, or Firm* — Myers Bigel, P.A.

(57) ABSTRACT

Processing containers include a first member having a substantially rigid body with a plurality of regions defining spaced apart workstations and a flexible barrier member sealably attached to the first member to define a closed chamber over the plurality of workstations. The flexible barrier is substantially impermeable and includes or is a manipulation tool that is sealably attached to the barrier. The manipulation tool has a first internal interface that resides in the closed chamber under the flexible barrier and a second external interface that resides outside the closed chamber. The processing containers are particularly suitable for automated processing of nucleic acids and other samples. The manipulation tool can cooperate with or include a pipette
(Continued)

head. When the barrier is sealed, the barrier separates the contents of the container from a robotic arm or other manipulation device.

18 Claims, 52 Drawing Sheets

Related U.S. Application Data division of application No. 14/692,131, filed on Apr. 21, 2015, now Pat. No. 9,409,178, which is a continuation of application No. 13/845,725, filed on Mar. 18, 2013, now Pat. No. 9,040,303, which is a continuation of application No. 13/490,863, filed on Jun. 7, 2012, now Pat. No. 8,431,404, which is a division of application No. 13/235,922, filed on Sep. 19, 2011, now Pat. No. 8,211,701, which is a division of application No. 12/159,748, filed as application No. PCT/US2007/001170 on Jan. 17, 2007, now Pat. No. 8,030,080.

(60) Provisional application No. 60/760,087, filed on Jan. 18, 2006.

(52) U.S. Cl.
CPC .... *G01N 35/00871* (2013.01); *B01L 2200/02* (2013.01); *B01L 2300/06* (2013.01); *B01L 2300/123* (2013.01)

(56) References Cited

U.S. PATENT DOCUMENTS

| | | |
|---|---|---|
| 4,815,256 A | 3/1989 | Brown et al. |
| 4,876,187 A | 10/1989 | Duck et al. |
| 4,895,280 A | 1/1990 | Tourigny |
| 5,030,557 A | 7/1991 | Hogan et al. |
| 5,130,238 A | 7/1992 | Malek et al. |
| 5,263,299 A | 11/1993 | Galbierz et al. |
| 5,287,857 A | 2/1994 | Mann |
| 5,356,034 A | 10/1994 | Schlumberger |
| 5,399,491 A | 3/1995 | Kacian et al. |
| 5,409,818 A | 4/1995 | Davey et al. |
| 5,437,990 A | 8/1995 | Burg et al. |
| 5,474,303 A | 12/1995 | Coles |
| 5,485,184 A | 1/1996 | Nakagomi et al. |
| 5,554,516 A | 9/1996 | Kacian et al. |
| 5,554,517 A | 9/1996 | Davey et al. |
| 5,556,365 A | 9/1996 | Drummond et al. |
| 5,578,270 A | 11/1996 | Reichler et al. |
| 5,693,233 A | 12/1997 | Schembri |
| 5,795,784 A | 8/1998 | Arnquist et al. |
| 5,851,492 A | 12/1998 | Blattner |
| 5,934,312 A | 8/1999 | Bellenger et al. |
| 5,939,582 A | 8/1999 | Dassel et al. |
| 5,947,890 A | 9/1999 | Spencer et al. |
| 6,030,582 A | 2/2000 | Levy |
| 6,232,464 B1 | 5/2001 | Lange |
| 6,361,136 B1 | 3/2002 | Watanabe et al. |
| 6,579,497 B2 | 6/2003 | Woodward |
| 2002/0004994 A1 | 1/2002 | Rudd |
| 2002/0086431 A1 | 7/2002 | Markham et al. |
| 2002/0159868 A1 | 10/2002 | Nadicksbernd |
| 2003/0152494 A1 | 8/2003 | Moritz et al. |
| 2003/0211539 A1 | 11/2003 | Frank et al. |
| 2003/0226796 A1 | 12/2003 | Bayer, Jr. et al. |
| 2004/0029260 A1 | 2/2004 | Hansen et al. |
| 2004/0241713 A1 | 12/2004 | Mirzabekov et al. |
| 2005/0042138 A1 | 2/2005 | Ueda et al. |
| 2005/0208539 A1 | 9/2005 | Vann et al. |
| 2005/0233370 A1 | 10/2005 | Ammann et al. |
| 2005/0266411 A1 | 12/2005 | Hofstadler et al. |
| 2006/0008906 A1 | 1/2006 | Wills et al. |

FOREIGN PATENT DOCUMENTS

| | | |
|---|---|---|
| WO | WO 99/57561 A2 | 11/1999 |
| WO | WO 03/036298 A2 | 5/2003 |
| WO | WO 03/100389 A1 | 12/2003 |
| WO | WO 2004/113052 A2 | 12/2004 |

OTHER PUBLICATIONS

Supplementary European Search Report for related EP Application No. 07835665.6 (6 pages) (Apr. 18, 2016).

U.S. Department of Health and Human Services, Guidance for Industry: Sterile Drug Products Produced by Aseptic Processing-Current Good Manufacturing Practice (Sep. 2004).

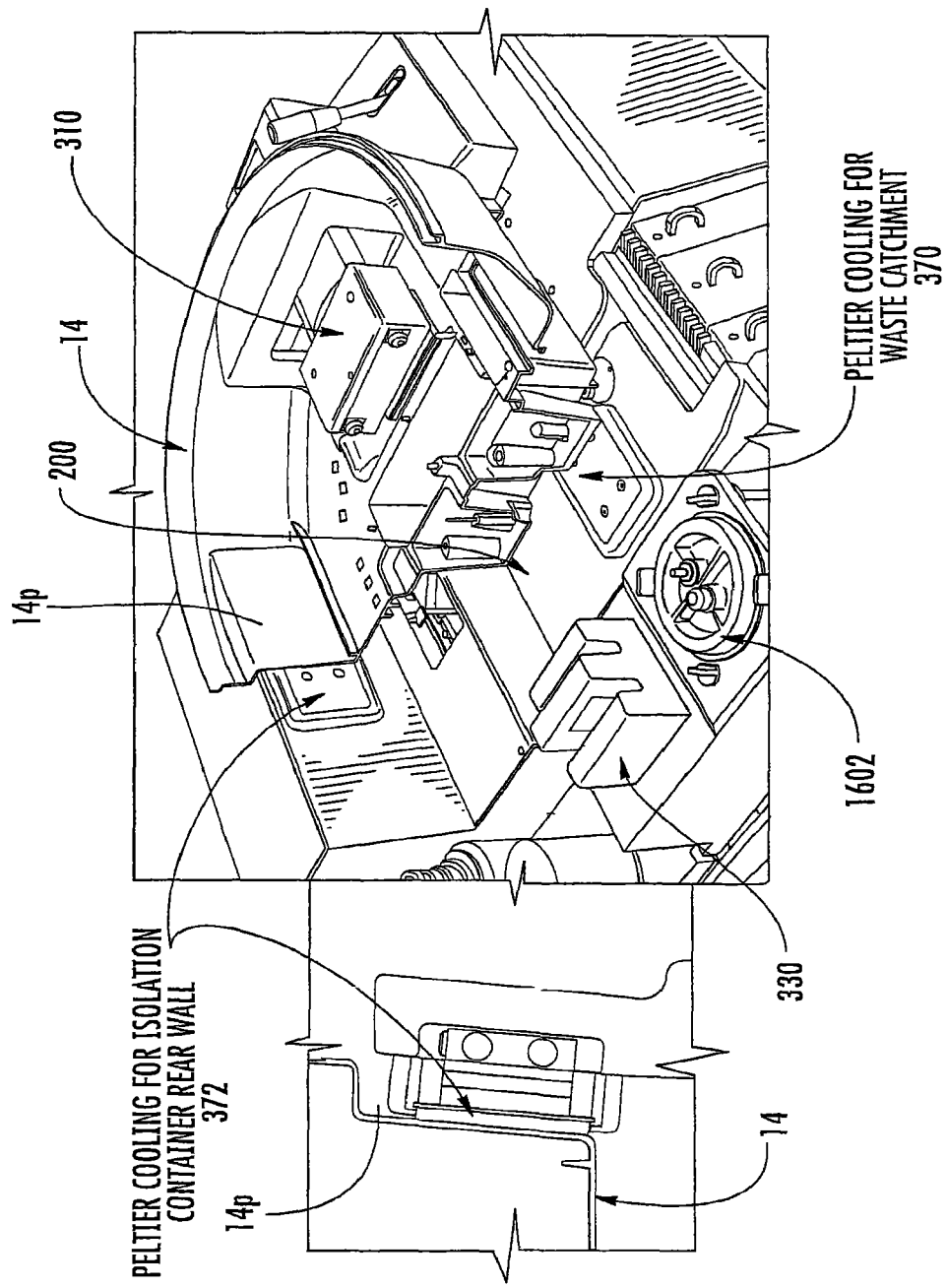

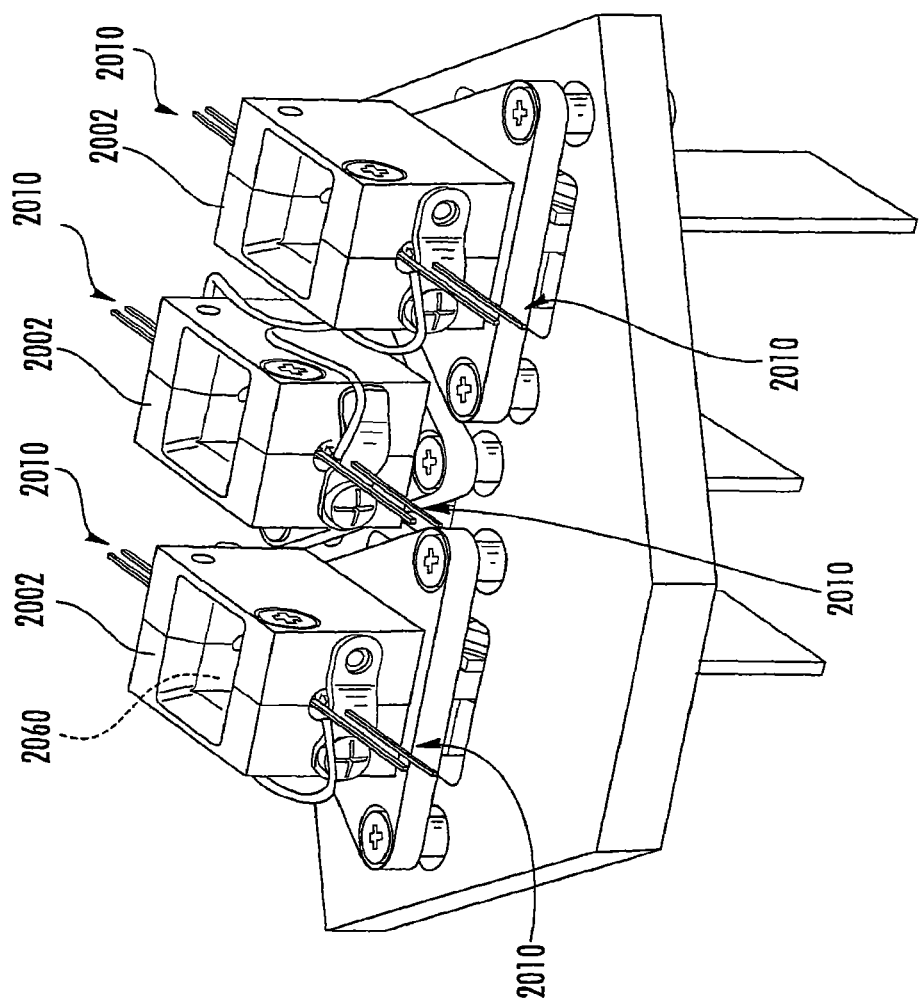

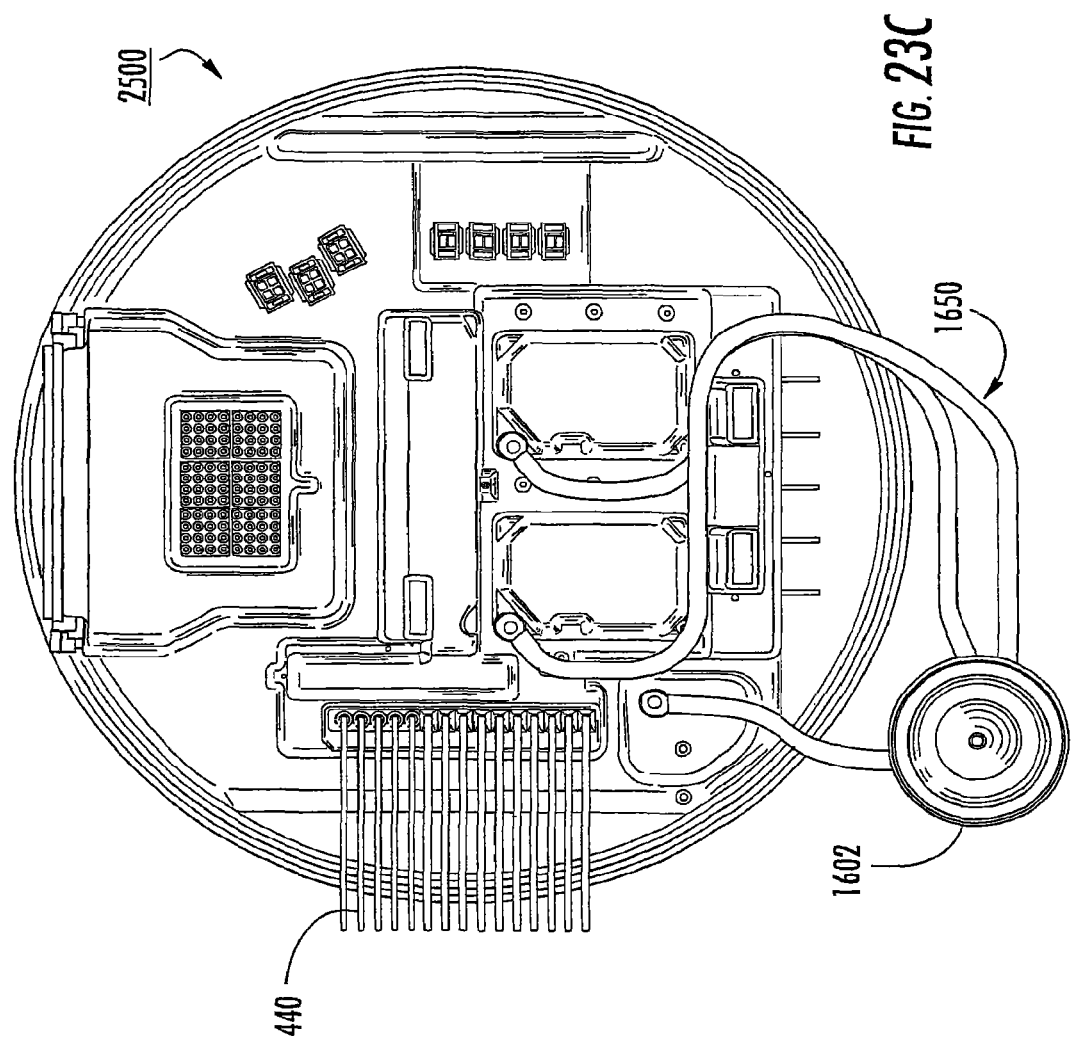

METHODS OF PROCESSING SAMPLES

RELATED APPLICATIONS

This application is a continuation application of U.S. application Ser. No. 15/216,128 filed Jul. 21, 2016, which is a divisional application of U.S. application Ser. No. 14/692,131 filed Apr. 21, 2015, which is a fourth (indirect) divisional application of U.S. application Ser. No. 12/159,748, with a 371(c) date of Feb. 12, 2009, which issued as U.S. Pat. No. 8,030,080, on Oct. 4, 2011, which is a 35 USC 371 national phase application of PCT/US2007/001170, filed Jan. 17, 2007, which claims the benefit of priority to U.S. Provisional Application Ser. No. 60/760,087, filed Jan. 18, 2006. The fourth divisional application U.S. application Ser. No. 14/692,131 filed Apr. 21, 2015, claims priority to U.S. application Ser. No. 12/159,748 through first divisional application U.S. application Ser. No. 13/235,922, filed Sep. 19, 2011, second divisional application U.S. application Ser. No. 13/490,863, filed Jun. 7, 2012, and third divisional application U.S. application Ser. No. 13/845,725, filed Mar. 18, 2013. The contents of the above documents are hereby incorporated by reference as if recited in full herein.

FIELD OF THE INVENTION

The present invention relates to automated processing of samples and materials, and may be particularly suitable for processing nucleic acids in a closed environment.

BACKGROUND OF THE INVENTION

Nucleic acid based amplification reactions are widely used in research and clinical laboratories to aid in the diagnosis of disease and/or identification of pathogenic organisms in a test sample. Such amplification reactions may also be used for development of vaccines, including, for example, autologous vaccines derived from a patient's own tumor cells. Amplification of nucleic acids isolated from tumor tissue allows for autologous vaccine production even from small tumors, and therefore affords the opportunity to treat patients with minimal tumor burden.

Generally stated, the currently known amplification schemes can be broadly grouped into two classes based on whether the enzymatic amplification reactions are driven by continuous cycling of the temperature between the denaturation temperature, the primer annealing temperature, and the amplicon (product of enzymatic amplification of nucleic acid) synthesis temperature, or whether the temperature is kept constant throughout the enzymatic amplification process (isothermal amplification). Typical cycling nucleic acid amplification technologies (thermal cycling) are polymerase chain reaction (PCR), and ligase chain reaction (LCR). Specific protocols for such reactions are discussed in, for example, Short Protocols in Molecular Biology, $2^{nd}$ Edition, *A Compendium of Methods from Current Protocols in Molecular Biology*, (Eds. Ausubel et al., John Wiley & Sons, New York, 1992) chapter 15. Isothermal reactions include transcription-mediated amplification (TMA), nucleic acid sequence-based amplification (NASBA), and strand displacement amplification (SDA).

Nucleic acid amplification is discussed in, for example, U.S. Pat. Nos. 4,683,195; 4,683,202; 5,130,238; 4,876,187; 5,030,557; 5,399,491; 5,409,818; 5,485,184; 5,409,818; 5,554,517; 5,437,990 and 5,554,516. It is well-known that methods such as those described in these patents permit the amplification and detection of nucleic acids without requiring cloning, and are responsible for sensitive assays for nucleic acid sequences. However, it is equally well recognized that, along with the sensitivity of detection possible with nucleic acid amplification, the risk of contamination by minute amounts of unwanted exogenous nucleic acid sequences is extremely great. The utility of amplification reactions may be enhanced by methods to control the introduction of unwanted exogenous nucleic acids and other contaminants.

In particular, for processing of biological samples, including for example the production of therapeutic agents, like vaccines for autologous therapy, current good manufacturing practice (GMP) typically requires manufacture in an aseptic environment.

Accordingly, there remains a need in the art to provide automated systems and methods for processing nucleic acids and other samples.

SUMMARY OF EMBODIMENTS OF THE INVENTION

Embodiments of the present invention are directed to systems, apparatus and methods for automated processing of one or more samples. The systems can be used to manipulate items in a closed environment, and may be particularly useful in the fields of medicine, diagnostics, biotechnology, electronics and nanotechnology. Embodiments of the invention may be particularly relevant for processing biological samples, including, but not limited to, tissues, blood, blood products, nucleic acids (e.g., RNA, DNA), proteins, cell cultures, and the like.

Embodiments of the present invention provide an apparatus for manipulating one or more items in a closed container. The container, also referred to herein as an "isolation container", comprises a tray defining an interior chamber, which is configured to hold any number of items to be manipulated, and a flexible barrier configured and dimensioned to cover the interior area and seal with the container tray. A tool for manipulating items within the interior area is attached to or integrated with or within the flexible barrier.

The tool can have a first interface that is accessible from an exterior side of the barrier that is configured to attach to a robotic device. The tool can also include a second interface that can extend from an opposite side of the barrier, such that it is disposed within the interior area when the flexible barrier is sealed with the container. The tool can be configured to manipulate items within the container when the robotic device is attached to the first interface. In some embodiments, the one or more items in the closed container comprise, for example, any of nucleic acids, other samples, reagents, wash fluids, pipette tips, vessels, other consumables and/or any combination thereof. Other tools or devices may also be disposed within the container, for example tools or devices for processing, manipulating, measuring, analyzing, sampling and/or storing samples or other items within the container.

In some embodiments, systems and methods for automated processing of nucleic acids and other samples include a single-use disposable isolation container assembly with a tray and a flexible barrier configured to seal with the tray, thereby providing a closed work area within the sealed tray. The closed work area may be aseptic.

A pipette head and/or other sample manipulation device can be attached to the inside of the barrier, and the barrier can include an interface for a robotic arm or other device that is used to manipulate items within the sealed work area.

When the barrier is sealed over the tray, the barrier separates the contents of the tray from the robot or other manipulation device. The barrier is flexible, and allows the robotic arm to move the pipette head or other sample manipulation devices throughout the work area of the tray. All samples, reagents, pipette tips and other consumables, tools or devices for processing nucleic acid samples may remain within the closed compartment provided by the isolation container during processing.

In another embodiment, methods of processing nucleic acids, (e.g., RNA and/or DNA) utilize a disposable (single-use) isolation container to reduce the risk of contaminating subject material with undesired biological matter, e.g., from an operator, another subject or the external environment. In some embodiments, the isolation container is designed for RNA isolation from a biological sample, including but not limited to one or more of the following: tumor tissue, blood, blood products, cells, pathogens, etc. In particular embodiments, the biological sample comprises a tumor homogenate, and the system provides all the features and functionality to convert clarified tumor homogenate into in vitro transcribed (IVT) RNA.

Typically, only the inside of the isolation container is exposed to the subject material, thereby preventing possible contamination of the processing system and reducing cleaning requirements between consecutive subject samples processed by the system. In some embodiments, the processing system processes samples in one isolation container at a time. In other embodiments, the systems can be configured to process samples in two or more isolation containers substantially concurrently.

In some embodiments, the present invention provides an apparatus for the transfer of fluid comprising working fluid and a working fluid pump that are separated from a sample device by a diaphragm. In use, a sample or other fluid may be drawn into or expelled from the sample device by a change in pressure which is transmitted across the diaphragm, e.g., by movement of the diaphragm when the working fluid pump changes pressure of the working fluid. In one embodiment, the sample device is a pipette tip or other tube for uptaking, dispensing and/or mixing fluidic samples, and/or for transferring a sample, reagent or other fluid from one location to another location. The pipette tip or tube may be of any suitable shape and size.

In yet other embodiments, the present invention provides an apparatus for measuring the volume of a fluid comprising: at least one light source or emitter and at least one receiver; a cuvette configured with a light path through which the receiver can detect a change in the light path associated with whether the cuvette contains fluid or is empty; and a fluid transfer device in communication with the receiver to determine the volume of fluid that has been removed from the cuvette.

Other embodiments are directed to biological sample processing containers. The containers include a single-use disposable tray having a substantially rigid body with a first workstation configured to hold a vessel for incubation in a thermal block (e.g., a single tube, multi-well plate or strips, a PCR plate, etc.), a second workstation configured to hold reagents, and a third workstation configured to hold pipettes.

Some embodiments are directed to flexible barriers having an outer edge portion configured to seal to a tray to define a sealed closed interior chamber. The flexible barrier includes an elastomer and is sealably attached to a robotic arm interface at a medial portion of the barrier.

Yet other embodiments are directed to an automated pipette tip disengagement system. The system includes: (a) a tray having a sidewall; and (b) a robotic arm merging into a manipulation tool having an outwardly extending lever configured to contact the tray sidewall, whereby contact with the sidewall forces the lever to pivot and release a respective used pipette tip held by the manipulation tool. In some embodiments, the tray has an angled sidewall that contacts the manipulation tool lever.

Some embodiments are directed to systems for processing liquids. The systems include: (a) a robotic arm; and (b) a manipulation tool that cooperates with the robotic aim, the tool configured to releasably engage a pipette tip and automatically translate to pierce a cover on a vessel a plurality of times in different spaced apart locations before withdrawing fluid from the vessel through one of the pierced openings in the cover.

Other embodiments are directed to elution trays. The trays are sterile biocompatible elution trays having a plurality of spaced apart receptacles, a plurality on a first side of an upwardly extending barrier and a plurality on an opposing side of the barrier. The receptacles have a channel that extends on each side of and tapers down in the direction of a primary tubular portion.

Still other embodiments are directed to kits for use with an automated processing system. The kits include: (a) a single-use disposable container comprising a tray and a flexible barrier configured to sealably attach thereto; (b) a single-use disposable reagent rack configured to reside in the container at a first workstation; (c) a single-use disposable binding column manifold configured to reside in the container; and (d) a single-use disposable pipette rack configured to reside in the container.

Some embodiments are directed to methods of transferring liquids. The methods include: (a) programmatically directing a robotic arm to move an interface tool releasably holding a pipette tip; (b) automatically piercing a sealant on a vessel holding a target liquid a plurality of times using the pipette tip; then (c) automatically withdrawing liquid from the vessel with the pierced sealant using the pipette tip.

Some embodiments are directed to methods of releasing liquids from pipettes. The methods include: (a) programmatically directing a robotic arm to move an interface tool releasably holding a pipette to orient the pipette in a downwardly extending angled orientation with the tip proximate to a receiving surface in a closed container; (b) then automatically moving the downwardly oriented angled pipette in a substantially straight line along a plane, while releasing a flowable substance from the pipette.

Yet other embodiments are directed to methods of aspirating liquids into pipettes. The methods include: (a) programmatically directing a robotic arm to move an interface tool releasably holding a pipette to engage a vessel holding a target fluid in a closed container; then (b) automatically moving the pipette inside the vessel to mix the liquid in the vessel; then (c) aspirating the mixed liquid into the pipette.

In some embodiments, the method can include aspirating and dispensing the liquid to mix the liquid (once or multiple times).

Still other embodiments are directed to automated methods of processing a sample in a closed system. The methods include: (a) providing a sample in a sealably closed container having a flexible barrier; and (b) programmatically directing a robotic arm to cooperate with the flexible barrier to move an interface tool inside the closed container through a series of operations while the closed container remains sealed to process the sample.

The method may optionally also include one or more of the following: (c) electronically and automatically measuring volume and concentration of the sample at a plurality of times during the amplification; (d) electronically and automatically monitoring seal integrity of the closed container before, after, and/or during use; and (e) capturing at least one amplified RNA sample in an aliquot vessel without disrupting the sealed status of the closed system.

Still other embodiments of the invention are directed to apparatus for manipulating items in a closed container. The apparatus include: (a) a container having an interior region configured to hold a plurality of items to be manipulated; and (b) a recirculating vacuum system configured to circulate air sealed within the interior region of the container in a closed loop.

Although described in some embodiments herein with respect to method aspects of the present invention, it will be understood that the present invention may also be embodied as systems and computer program products. Also, it is noted that any of the features claimed with respect to one type of claim, such as a system, apparatus, method or computer program, may be claimed or carried out as any of the other types of claimed operations or features.

Other systems, methods, system components and/or computer program products according to embodiments of the invention will be or become apparent to one with skill in the art upon review of the following drawings and detailed description. It is intended that all such additional systems, methods, and/or computer program products be included within this description, be within the scope of the present invention, and be protected by the accompanying claims.

BRIEF DESCRIPTION OF THE DRAWINGS

Other features of the present invention will be more readily understood from the following detailed description of exemplary embodiments thereof when read in conjunction with the accompanying drawings, wherein like references numerals represent like elements. The drawings are merely exemplary to illustrate certain features that may be used singularly or in combination with other features and the present invention should not be limited to the embodiments shown. Features shown with respect to one embodiment or figure may be used with other embodiments or figures.

FIG. 11 is a perspective view of a thermal cycler assembly with a thermal cycler lid drive system according to embodiments of the present invention;

FIG. 18 is a perspective view of a processing system work surface with a cutaway of an isolation tray, showing cooling units for controlling humidity and vapor concentrations according to embodiments of the present invention;

FIG. 20E is a top, side perspective view of a multi-cuvette volume measurement system that can operate as described with respect to FIGS. 20A-20D according to embodiments of the invention;

FIG. 23C is a bottom view of the partially assembled kit shown in FIG. 23B;

DETAILED DESCRIPTION

Figure 1:
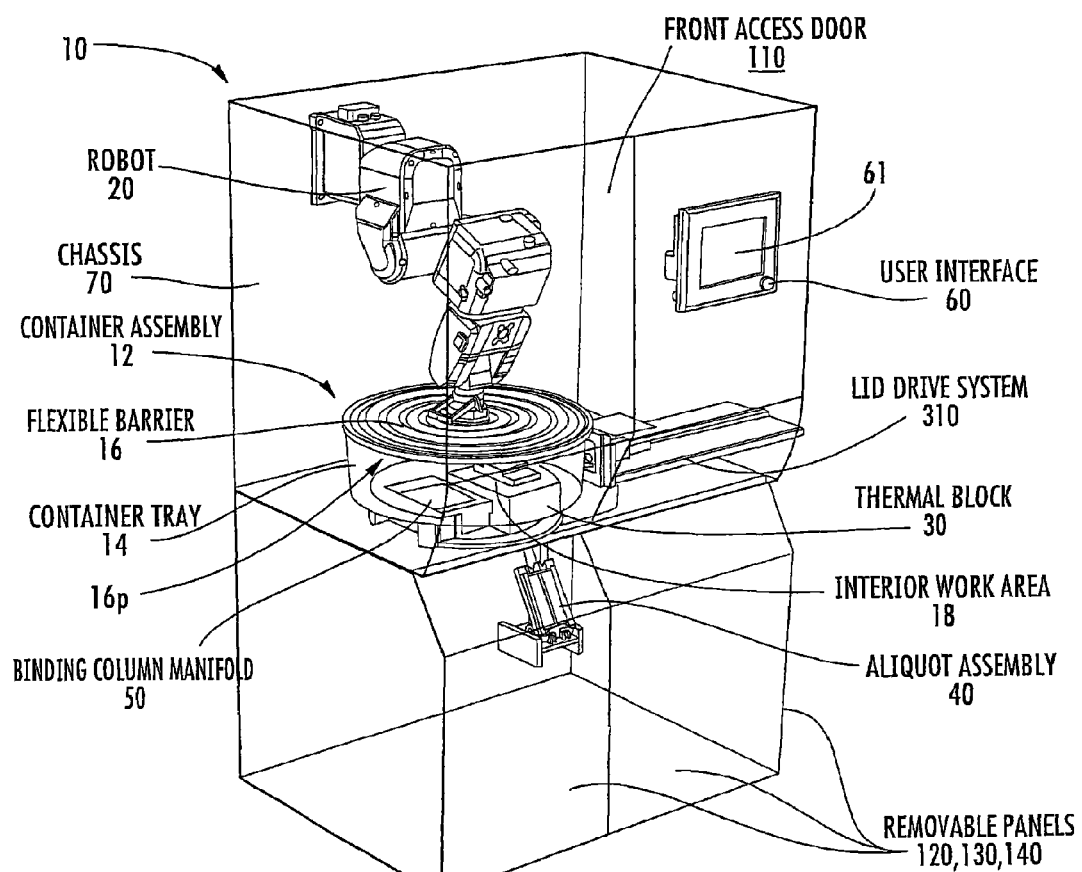
FIG. 1 is a perspective view of a processing system according to embodiments of the present invention.

While the invention may be made in modified and alternative forms, specific embodiments thereof are shown by way of example in the drawings and will be described in detail. It should be understood, however, that there is no intent to limit the invention to the particular forms disclosed, but on the contrary, the invention is to cover all modifications, equivalents, and alternatives falling within the spirit and scope of the invention. Like reference numbers signify like elements throughout the description of the figures.

In the figures, the thickness of certain lines, layers, components, elements or features may be exaggerated for clarity. Broken lines illustrate optional features or operations or hidden components unless specified otherwise. In the claims, the claimed methods are not limited to the order of any steps recited unless so stated thereat.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

The terms "closed system" or "closed container" refers to systems and containers, respectively, that are sealed and operate in a substantially, if not totally, closed manner to inhibit or prevent the introduction of exogenous or external materials into (or out of) the system or container during processing. The closed systems can be configured to inhibit or prevent contamination. In some embodiments, components of the closed systems or containers can be pre-sterilized prior to use at a manufacture site, sterilized at the point of use, and/or sterilized after a respective closed system is assembled and closed prior to use. The closed systems or containers can be pressure- or vacuum-tight to some target or predefined leak rate at certain atmospheric conditions. The leak rate may be detected by an internal and/or external sensor using a vacuum or pressure sensor test or other leak check system and the like. The typical atmospheric conditions may change with location of the apparatus, from sea level to higher altitudes. However, the closed systems contemplated by embodiments of the invention may be used in marine (subsurface, deep sea), flight, and/or space environments as well, with the seal being sufficient to substantially maintain the target leak rate at those atmospheric conditions. The closed systems or containers can be utilized for their respective intended purpose without breach to the integrity of the closed system. The closed systems or containers may be adapted for fluid transfers of target fluid samples in or out while maintaining asepsis, and/or can be connectable to other closed systems while maintaining the integrity of the closed systems. Filters may optionally be used in a flow path that may be open to atmosphere or other components during process. The filters may be configured to filter to a desired clean level or class, to facilitate the closed state, such as class 100,000, class 10,000, class 1000 filters or even class 100 filters.

The term "isolation container" refers to a container configured to hold, enclose and/or isolate internal components and the processing of one or more items or samples held therein from external pathogens, microorganisms and the like and/or other materials that may exist in an external environment. The isolation container may be a single-use disposable container. In some embodiments, the samples in the isolation container are or comprise nucleic acids, e.g., for processing nucleic acids in tissues (e.g., clarified tumor homogenate) into IVT RNA.

The term "single-use disposable" refers to a component that is not reused. That is, after completing its intended use, i.e., processing or production of a target sample or sample(s), it is disposed of. The isolation container can be single-use disposable (and may be labeled as such), such that the isolation container remains a closed system that is disposed of in the closed sealed state with its internal components held therein, to inhibit any inadvertent external release or exposure of its internal content(s) after processing/production of the target product.

The term "aliquot" refers to a desired amount of a target fluid; the amount of fluid may be in a predetermined and/or specific range. The term "aliquot tube" refers to a tube that permits removal of a fluid aliquot from the container. Typically, the term "aliquot tube" refers to a tube that is in communication with the interior of the isolation container to receive at least one (and typically a plurality of) fluid aliquot without breaching the closed status or sealed integrity of the isolation container. The aliquot tube can be flexible and sterile and may comprise an elastomer, such as PVC.

The term "cuvette" refers to a vessel configured to permit mechanical, electrical or optical measurement(s) of a substance, typically a fluid, and typically concentration or volume measurements, contained within that vessel. The cuvette may be sized to hold a relatively small amount of fluid, typically, in the range between about 0.001 mL to about 5.0 mL.

The term "pipette tip" refers to a tube open at both ends to be able to intake and/or discharge fluid, typically liquids in small volumes, and typically in amounts between about 0.1 µL to about 1000 µL. The tube may have an irregular or constant perimeter shape or size, typically tapering down at a lower tip from the head. A "pipette" can be defined by a plurality of matable components. That is, a pipette can include a tip portion and a head portion. The head portion can be defined on a manipulation tool attached to a robotic device (indirectly) that releasably attaches to different pipette tips during processing. Pipettes of different volumetric sizes may be used in a single container/processing system.

The term "Human Machine Interface (HMI)" is well known to those in the art and refers to an interface which allows an operator to input, direct, interact with or machines, and typically includes an electronic display with a "Graphic User Interface (GUI)" that programmatically provides information to and accepts control instructions from an operator.

The term "aseptic" refers to processing conditions that inhibit or prevent contamination of a target sample in an interior processing space of a container by external pathogenic microorganisms and/or undesired exogenous materials, and/or to inhibit or prevent contamination of the proximal exterior environment with the contents of the container.

The term "binding column" refers to a filtration/elution column that can be used for separating components of a sample or derivatives thereof. In some embodiments, the binding column can be used for nucleic acid (e.g., DNA and/or RNA) isolation or purification. In some embodiments, the binding column may contain a silica membrane.

The term "tray" refers to a substrate having sufficient rigidity to hold one or more components. The tray may be substantially flat or may have a bowl-like shape. The tray may also have other shapes and configurations. The tray can be configured to define integral wells or holding, regions or may be configured to sealably mate with and/or hold devices or containers, typically those components associated with at least one processing workstation.

The term "user" is a generic term for an operator, programmer, and/or maintainer.

The term "robot" refers to an automated device that can be programmatically directed to translate in desired directions to carry out defined processing steps or operations. The term "robot" is used broadly and includes a stationary mounted robotic arm with a multi-axis translation as well as a fully mobile robot and other appropriate robotic devices.

The present invention may be embodied as systems, methods, and/or computer program products. Accordingly, the present invention may be embodied in hardware and/or in software (including firmware, resident software, microcode, etc.). Furthermore, the present invention may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium, upon which the program is printed, as the program can be electronically captured, via, for instance, optical scanning of the paper or other medium, then compiled, interpreted, or otherwise processed in a suitable manner, if necessary, and then stored in computer (electronic) memory.

Apparatus and methods for automated processing in a closed environment are discussed below. The systems can be used, for example, to process, fabricate, assemble or otherwise manipulate anything in a closed environment, and is particularly useful in the fields of medicine, forensics, therapeutics, diagnostics, biotechnology, electronics and nanotechnology. For convenience of description, various aspects and features of the invention are described herein in the context of a system for processing nucleic acids. One skilled in the art will appreciate, however, that the following descriptions are intended to be merely illustrative of the invention and not restrictive. Various other applications are intended within the scope of the present invention, including, for example, systems and methods for fabricating, assembling, processing or otherwise manipulating any items in a closed container.

Overview of Exemplary Automated Systems

In overview, referring to FIG. 1, the system 10 can be configured with a robotic arm 20 that manipulates one or more items within a closed container assembly 12 with an interior chamber (also described as an interior work area or region, where the word "area" is used broadly and not in a two-dimensional mathematical manner). In some embodiments, the container assembly 12 has an interior region 18 configured to hold a plurality of items to be processed and/or otherwise manipulated. A flexible barrier 16 can be configured and dimensioned to cover the interior of and seal with a container tray 14. A tool for manipulating items within the chamber is attached to or integrated within the flexible barrier 16 and can extend into the interior region when the barrier 16 is attached to the tray 14. The tool can have an adapter or other interface that is accessible from an exterior side of the barrier, such that the tool may be manipulated by a robotic device from outside of the container when the barrier is sealed with or otherwise attached to the container tray. The tray 14 may be configured to include one or more workspaces, areas, stations, racks, holders, receptacles, wells or other devices for holding one or more items or process components or fluids in the closed container. Other tools or devices may also be disposed or otherwise accessible from within the container; for example, tools or devices for processing, manipulating, measuring, analyzing, sampling and/or storing samples or other items may reside within the chamber of the container.

Turning now to the figures, FIG. 1 shows an exemplary automated nucleic acid processing system 10. System 10 may include a container assembly 12. The container assembly 12 may be an isolation container 12. The system 10 also includes a robot 20 (typically a robotic arm) or other automated or manually directable device for manipulating items within and/or associated with the container assembly 12. The container assembly 12 comprises the tray 14 and the flexible barrier 16. The barrier 16 is configured to seal with or otherwise attach to the tray 14. An outer perimeter edge portion 16p of the barrier 16 can sealably engage the container tray 14, providing a closed, aseptic work area 18 within the container assembly 12. In some embodiments, the container assembly 12, or any portion thereof, is single-use disposable. In particular embodiments, the sample can be discharged, collected or captured outside of the container without opening the sealed container, and the sealed container 12 can be disposed of "intact" with the remainder internal contents.

The tray 14 can be substantially rigid and may be a molded body. In some embodiments, the tray 14 comprises a medical grade (such as USP Class VI or other suitable grade) molded polymer. The body of the tray 14 may comprise one or more substantially clear, translucent or transparent polished regions for optic visibility that provides for internal viewability. The tray 14 can be molded in a clean room mold and in a clean room molding facility to inhibit and/or minimize bioburden and particulates. The tray 14 may be sterilized prior to or after sealing the flexible barrier 16, by using conventional sterilization techniques, such as, for example, surface decontamination with VHP (vaporous hydrogen peroxide), gamma irradiation or ethylene oxide vapor hydrogen peroxide. For shipment, the tray 14 may be enclosed in double elastomeric sterile packaging material, such as such as sealed double plastic wrapping/bagging.

The barrier 16 can be configured to allow the robot 20 to move a tool inside the work area 18 of the sealed container assembly 12 between about 4-24 inches vertically, and horizontally at least about the width and length of the tray 14, without destroying the sealed integrity of the container assembly 12. In some embodiments, the robot 20 can direct an internal interface to have between 6-12 inches of vertical movement in the sealed container assembly 12 without destroying the sealed integrity of the seal. The barrier 16 can be sized and configured relative to the tray 14 to provide for a sufficient volume of air to allow the desired range of movement of the robot 20 without overly compressing or decompressing the interior volume of the container 12.

In some embodiments, the system 10 is used to process biological samples, including, but not limited to tissues, blood, blood products, nucleic acids, proteins, cell cultures, and the like inside the container assembly 12. In such embodiments, the container 12 may comprise, for example, items such as biological samples, reagents, wash fluids, pipettes, pipette tips, vessels, other consumables or any combination thereof.

As shown, the system 10 can be a self-standing, self-contained unit. The system 10 can include a housing or chassis 70 for supporting an isolation container assembly 12 and other components of the automated system 10, such as, for example, the robot 20, a thermal block 30 (e.g., a heat block and/or cooling block, etc. . . . ), an aliquot retrieval assembly 40 and related mechanisms for collecting processed samples, a user interface 60, and various other components and mechanisms as described in the sections that follow. The thermal block 30 may cooperate with a thermal block assembly 1000 as shown, for example, in FIGS. 10, 11.

In some embodiments of a processing system 10, an operator or maintainer may only need to access the front of the system 10 for normal operation. As shown in FIG. 1, one or more access doors 110 may open, e.g., by lifting substantially vertically or opening to a side or in another direction, to provide accessibility while installing or removing an isolation container 12.

In some embodiments, due to the automated nature of system 10, the door 110 may protect the operator from moving parts of the system during operation. The system 10 may incorporate an electronically controlled interlock or other mechanism to inhibit or prevent the operator from opening the door 110 while the system is in operation. A manual override may be provided to allow opening of the interlocked guards, and such an override may be employed, for example, if no power is available. The user interface 60, also referred to as an HMI (Human Machine Interface), can be configured to allow an operator to initiate a processing operation or otherwise control the system 10, and can be mounted on the front of the chassis 70 next to the access door 110. In one embodiment, the display screen 61 and controls (touchscreen, keypad or other input) of the HMI may be positioned to allow the user to view and operate them while standing. In some embodiments, the rear and sides of the system 10 do not need to be routinely accessed by operators. Consequently the system can be positioned against a wall or another system.

In some embodiments, a lower section of the chassis 70 can contain electronic control systems, power supplies and other components, which may not require operator interaction. These components can be housed in dedicated enclosures that protect the components from accidental fluid ingress and protect the operator from possible electrical hazards. Removable panels 120, 130, 140 may be included to provide access to the electrical components and/or other components inside the enclosures. In some embodiments, only trained service personnel are permitted or required to access the insides of these enclosures. The service access panels may or may not be interlocked, for example, to allow or disallow the system to continue to operate with the panels removed.

Figure 2:
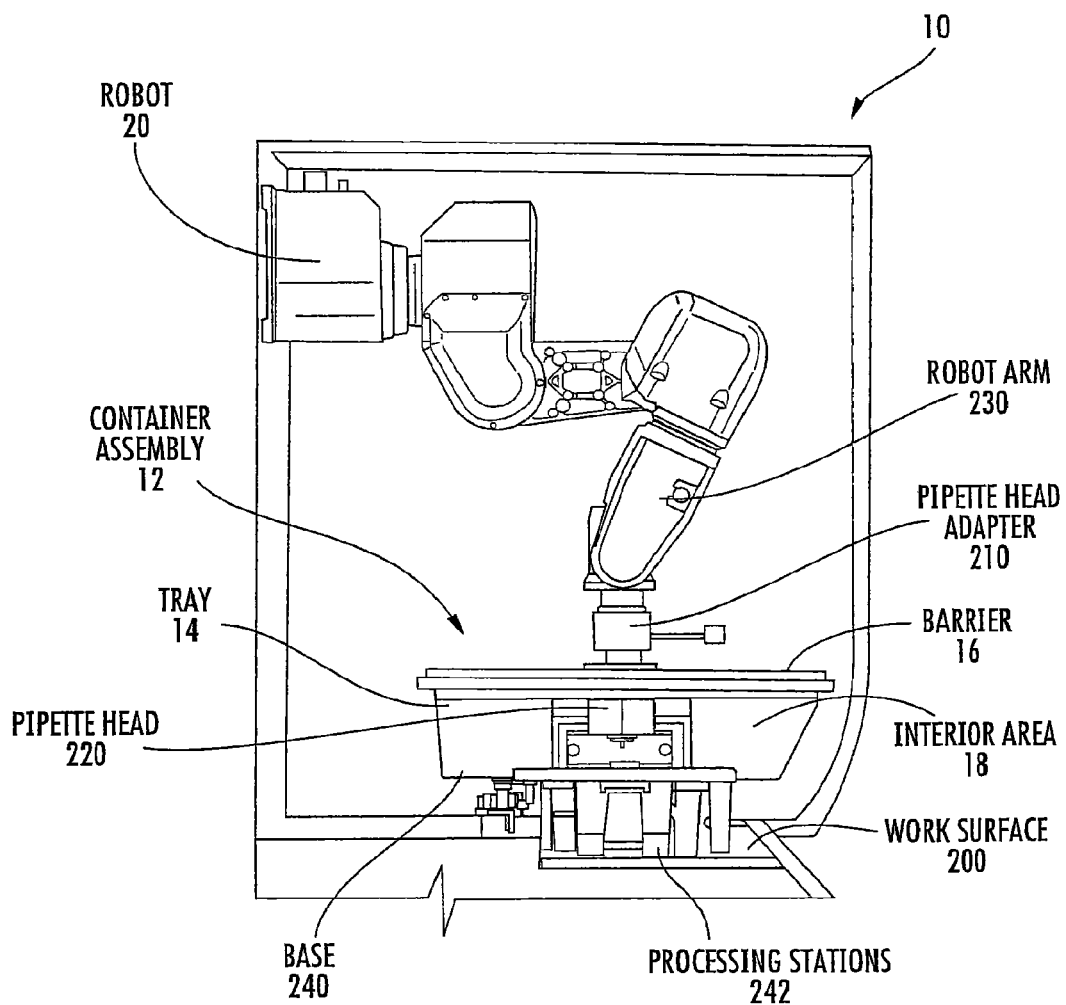
FIG. 2 is a side view of the upper portion of the system of FIG. 1, including an isolation container on a work surface.

FIG. 2 shows an enlarged side view of an upper portion of system 10, including isolation container 12 on a work surface 200. A pipette head 220 and/or other manipulation device can be attached to or integrated with or within the barrier 16, for example, such that at least a portion of a pipette head 220 extends into the interior work area 18 of container 12 when the barrier is attached to the tray 14 as shown. The pipette head 220 can include an interface on an opposite side of barrier 16 that is configured to releasably connect with an adapter 210 on an end portion of arm 230 of robotic device 20. In some embodiments, a pipette head 220 or other manipulation device does not physically pass through the barrier 16, and may not necessarily couple to a robot or other device through an adapter. Rather, such a pipette head may attach to or otherwise integrate with the inside of the barrier, and may be operated or manipulated from the opposite side of the barrier 16, for example, using the robotic arm 230 attached to the opposite side of the barrier. In other embodiments, a pipette head or other sample manipulation device integrated with the barrier 16 (which can be substantially impermeable) may be operated by a magnet or other device that supports and/or communicates with the manipulation device through the barrier 16.

When the barrier 16 is sealed over the tray 14, the barrier 16 separates the contents of the tray 14 from the robot 20 or other device that manipulates the pipette head 220. The seal between barrier 16 and tray 14 can be airtight, thereby providing a closed environment within the container 12. In some embodiments, the barrier 16 is flexible and allows the robotic arm 230 to move the pipette head 220 throughout the work area 18 within tray 14. All items or materials involved in processing the nucleic acid samples, including for example biological samples, reagents, pipette tips, or other consumables, and other tools or devices for processing the samples, can remain within the closed work area 18 during processing. The tray 14 may include a number of features or stations 242 which may be molded, formed, attached or otherwise integrated with base 240 of the tray 14, or another portion of the tray 14, to accommodate such items.

As shown, robotic device 20 may be attached to a wall of the chassis 70. In other embodiments, robotic device 20 may comprise an arm, gantry or linkage system attached to work surface 200 or to another support structure. Suitable robotic devices are known in the art. Non-limiting examples include Staubli TX90 robot, Epson E2L Scara robot, Kawasaki F Series robots, Yamaha YKL Scara robot, ST Robotics R17 Robot, etc. In some embodiments, the robotic device 20 is a FANUC LR MATE 200iB 5C, 6-axis robot or other suitable multi-axis robotic device, and is used to automatically perform the desired manipulations inside the closed container 12, such as, for example, aspiration and transfer of fluids using pipette tips and sliding or lifting a binding column manifold during processing of samples.

The multi-axis robotic arm can be used to move an interface tool releasably holding a pipette to orient the pipette in a number of different directions to help mix the liquid upon aspiration or dispensing. For example, the pipette can be oriented in a downwardly extending angled orientation with the tip proximate to a receiving surface in a receiving vessel in the closed container, then, automatically, the downwardly oriented angled pipette can be moved in a substantially straight line along a plane (similar to a typically layering or dispensing of mustard), while releasing a flowable substance from the pipette. In other embodiments, the robotic arm can automatically move the pipette to mix the liquid in the vessel prior to aspiration, then aspirate the mixed liquid into the pipette. Alternatively or additionally, in some embodiments, the liquid can be aspirated and dispensed at least once to mix the liquid. In some embodiments, the receiving or dispense vessel has a lip, and the robotic arm is configured to direct the pipette tip to move around the perimeter of the lip.

Figure 3:
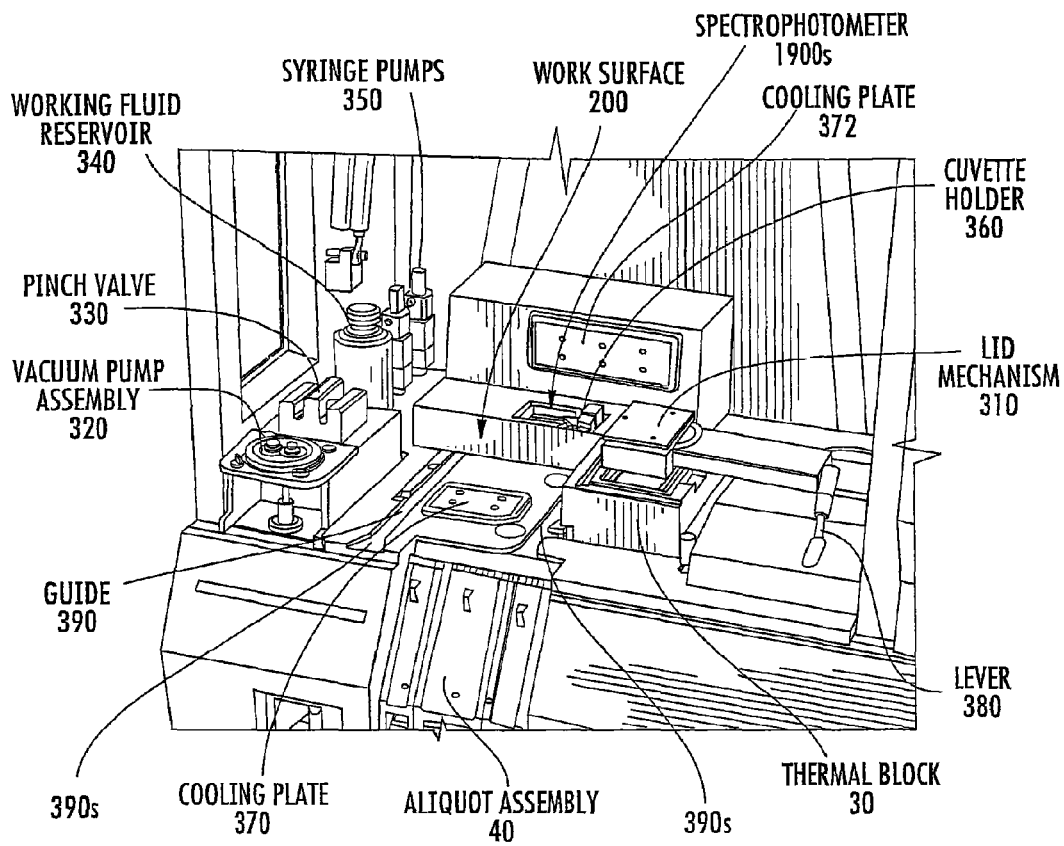
FIG. 3 is a perspective view of one embodiment of the work surface of the system of FIG. 1, illustrated without the isolation container.

As shown in FIG. 3, the horizontal work surface 200, which may be located inside of front access door 110, for example, supports various components and mechanisms that interact with an isolation container 12. The work surface 200 can include one or more guides 390, that may include guide slots 390*s* that engage components on an assembly support trolley 399 (FIG. 27) to align the container, or other location features to orient and releasably clamp to the isolation container 12 (e.g., to base 240 of FIG. 2) during processing.

Figure 27:
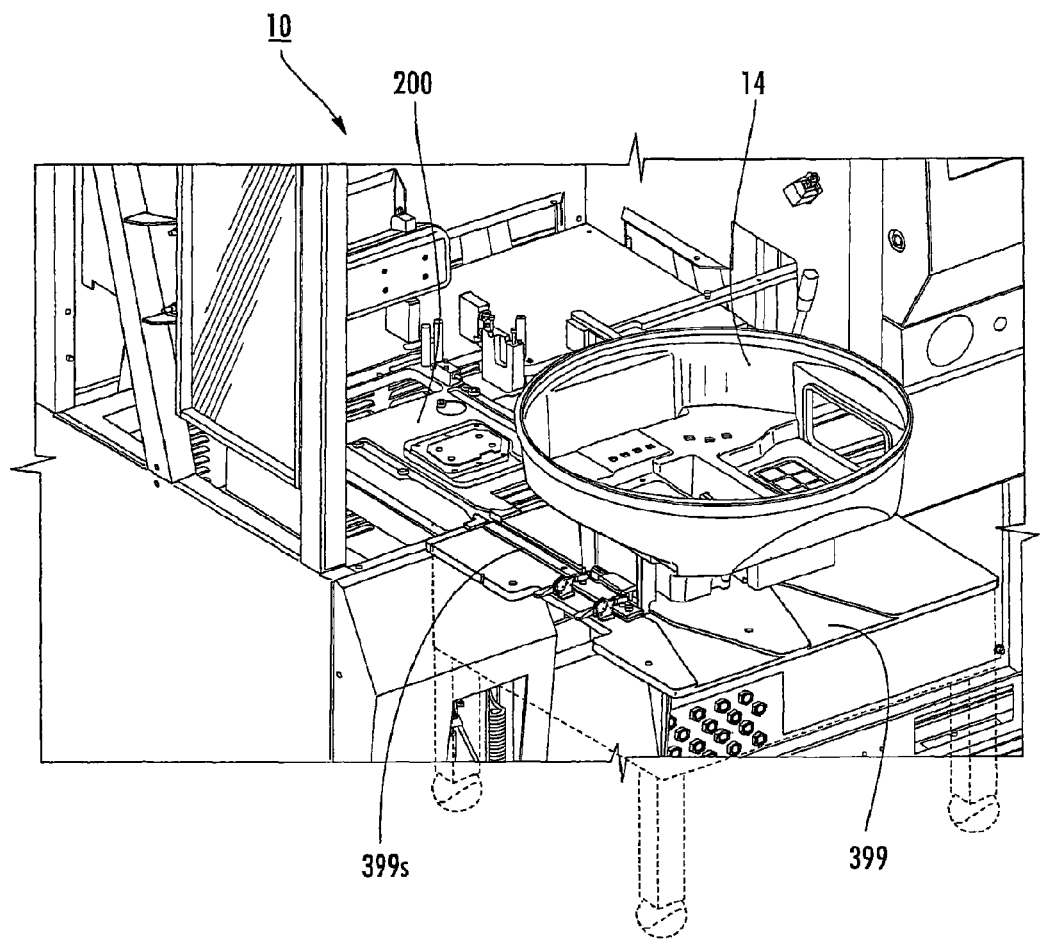
FIG. 27 is a top perspective view of a trolley that can be used to load the container onto an instrument according to embodiments of the present invention.

As shown in FIG. 27, a container assembly 12 can be prepared on a trolley 399 that can dock with the system 10. The trolley 399 can include slots 399*s* that align with slots 390*s* defined by guide 390 on a support surface of the system 10. To transfer the container assembly 12 to the system 10, an operator can roll the trolley adjacent to the system 10, so that the trolley 399 is aligned with the guide 390 of the system 10. The container assembly 12 can slide into the slots 390*s* of the system 10 into proper operative position without requiring that an operator lift the container assembly 12.

Figure 28A:
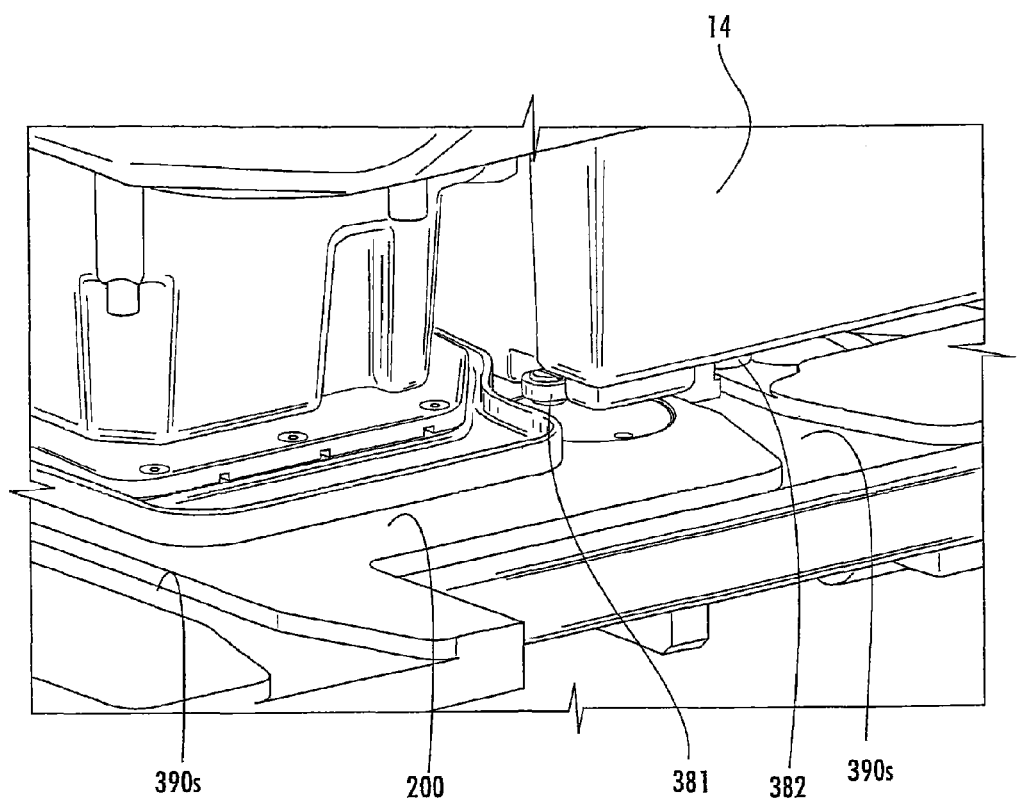
FIG. 28A is an enlarged side perspective view of a work surface with a biasing assembly configuration that can force the container into alignment with the robotic arm according to embodiments of the present invention.
Figure 28B:
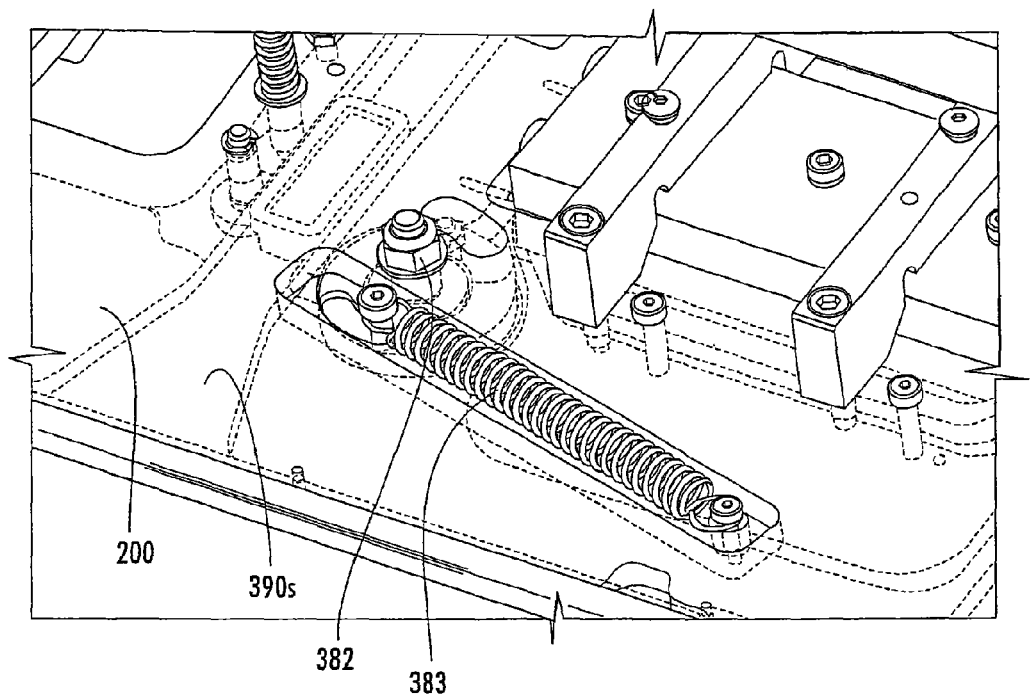
FIG. 28B is a bottom perspective view of a portion of the work surface shown in FIG. 28A illustrating a spring used to force the container in a desired direction according to embodiments of the present invention.

As shown in FIGS. 28A and 28B, the work surface 200 can include roller guides 381, 382 that contact the lower portion of the container 12 when it is in position. The roller guide 382 can be in communication with a spring 383 that can bias the container 12 inwardly so as to fit snugly against the innermost slot wall 390 to be in the desired alignment with the robotic arm for registration of workstation locations.

Referring again to FIG. 3, the work surface 200 may support a temperature control device, such as an incubation device for heating and/or cooling regions, vessels, or target objects or locations within the container. Such devices are known to those of skill in the art. In one embodiment, the system 10 includes a thermal cycler 30 for controlling temperature of a PCR plate 610 (FIG. 6) or other vessel or component during some nucleic acid amplification reactions or other reactions or processes, for example, and a thermal cycler lid mechanism 310 for selectively covering the thermal cycler 30 during such reactions. In one embodiment, a vacuum pump assembly 320 and a pinch valve assembly 330 provide for control of vacuum and circulation of air within the isolation container 12 during processing. The vacuum pump assembly 320 can releasably engage a single-use disposable vacuum head 1602 and associated tubing 1650 (FIG. 23B). The work surface 200 can also hold the container assembly 12 so as to allow a spectrophotometer 1900s to communicate with components held by the container assembly 12 as will be discussed further herein.

One or more syringe pumps 350 (shown, for example, as two pumps) may be used to drive aspiration and dispense actions of pipette head 220 (FIG. 2). In some embodiments, syringe pumps 350 may be used to pump a working fluid, e.g., from a reservoir 340, through the pipette head adapter 210 shown in FIG. 2 to provide vacuum and pressure for operation of pipette head 220. The working fluid may be substantially incompressible, and can, for example, comprise an aqueous solution of about 50% ethanol. Other fluids, even air, may be used. Additional details of an exemplary embodiment of a pump mechanism and pipette head 220 are described in greater detail below in connection with FIGS. 7 and 8.

Returning to FIG. 3, a cuvette holder 360 (see also spectrophotometer cuvette in FIG. 19A) can be coupled with a spectrophotometer 1900s typically residing in a lower portion of the chassis 70, to provide automatic concentration measurements at desired operations during processing. Optionally, the work surface 200 may include one or more cooling features, e.g., a heat exchanger such as a chiller or Peltier cooling plates 370 and 372 are positioned to engage certain portions of the isolation container 12 and help control humidity and vapor concentrations within the sealed container 12. A lever 380 or other mechanism or device may be used to secure the isolation container into place on the work surface 200.

In some embodiments, an RNA processing system may operate in a stand-alone fashion isolated from a larger production system and any data management tools or systems. An internal or external computer system may control and/or monitor the automated components of the subsystem. Users may interact with the interface 60, for example, to operate the system and monitor status. In other embodiments, the system 10 can communicate with other systems or a monitoring station (which may be in a different room or even in a different facility).

Additional details of the various components and assemblies, and exemplary methods of use, are described in sections that follow.

Exemplary Isolation Containers

Figure 5:
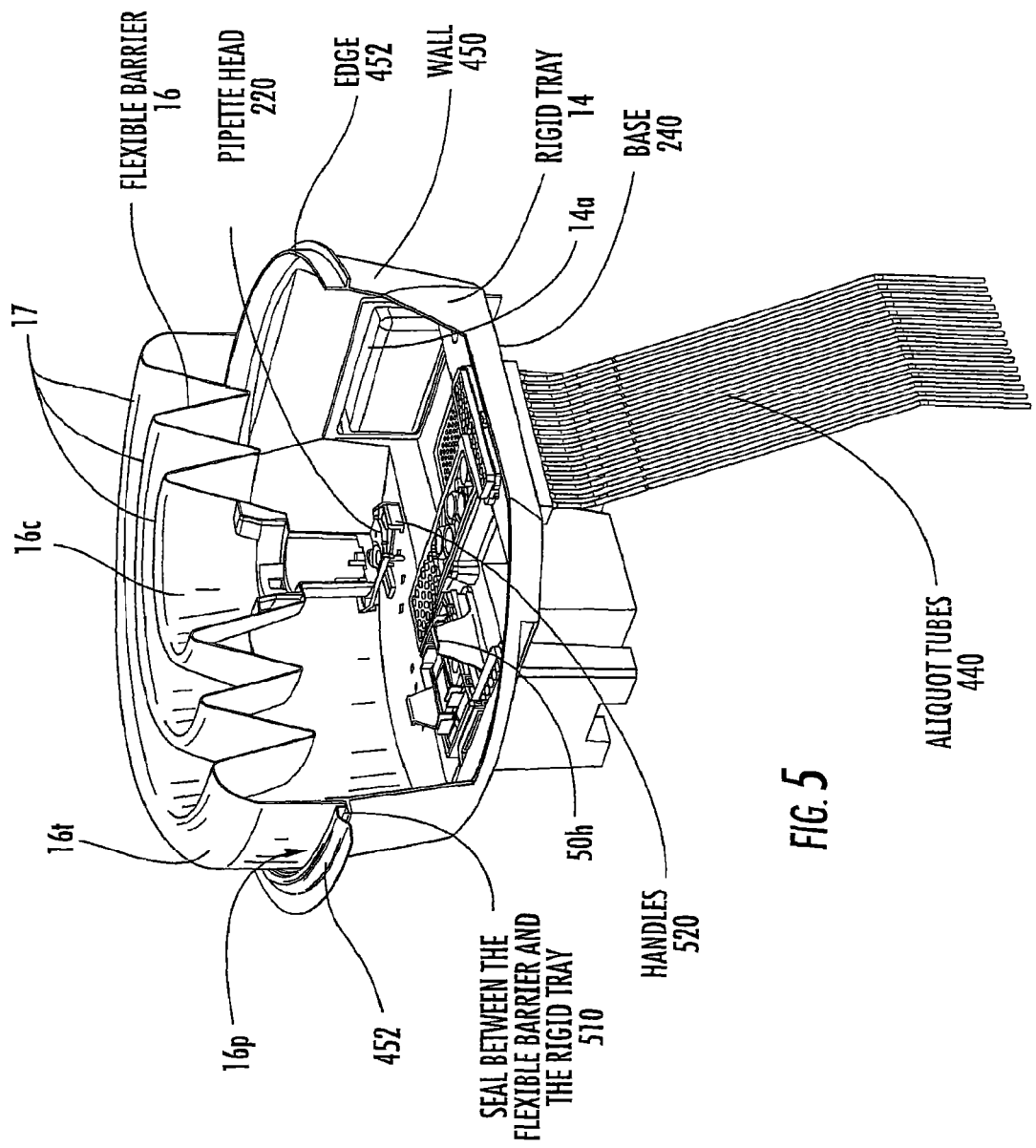
FIG. 5 is a cutaway perspective illustration of an isolation container assembly according to embodiments of the present invention.

Referring to the isolation container assembly 12, tray 14 and flexible barrier 16 are described in greater detail. The tray 14 includes an interior work area 18 and may comprise a number of inserts, recesses, racks, or rack mounting features and/or stations 242 for holding items within container 12, e.g., including one or more racks, manifolds or other holders for holding vessels, pipette tips, binding columns, other substrates and/or other consumables or devices for a desired assay or process. All items used to process the material to a desired finished state or product can be held within the container, i.e., the consumables for the system can be self-contained and sealed during processing to minimize the risk of contaminating the interior of the container, or to prevent a sample from contaminating the environment or user. The barrier 16 can have an outermost perimeter portion 16p (FIG. 5) that can be configured to releasably or permanently seal with the tray 14, for example about an annular edge 452 of tray 14 as shown in FIG. 5. When the barrier 16 is sealed with the tray 14, at least a portion of pipette head 220 and/or another sample manipulation tool or device extends from the barrier 16 into the work area 18.

, In some embodiments, the barrier 16 engages the tray 14 along a rigid top edge 452 (FIG. 5). The outermost perimeter portion 16p of the barrier 16 can reside against the top edge 452 (FIG. 5). The top edge 452 may be configured as an upstanding lip with a gap space that receives an O-ring (not shown) that pinches against the barrier 16 to seal the barrier against the tray 14.

Figure 4:
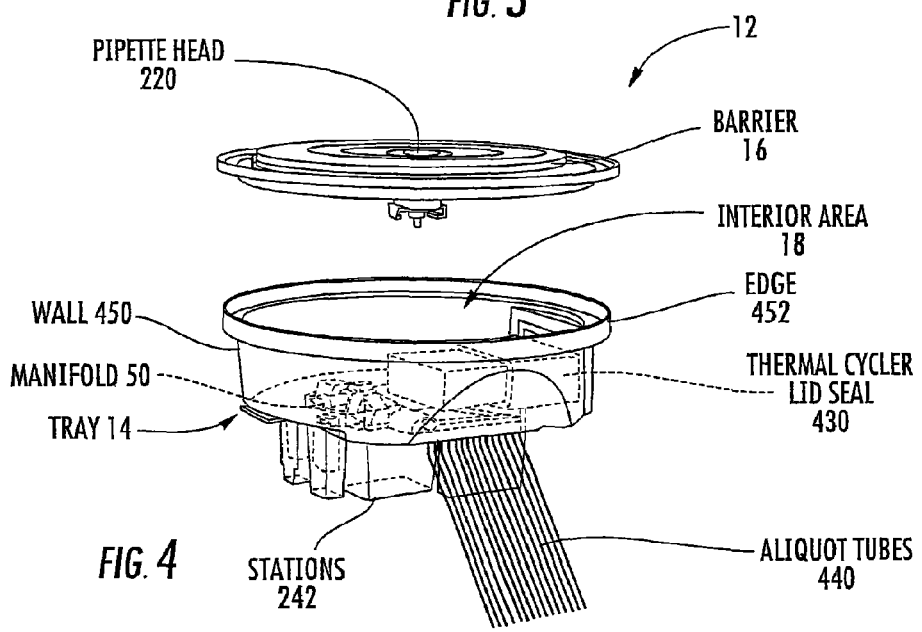
FIG. 4 is a perspective view of an isolation container assembly with the flexible barrier not yet attached according to embodiments of the present invention.

To create a closed system or environment, the isolation container tray 14 and barrier 16 may be configured to form a physical barrier between items within the container 12 and external devices, mechanisms and pieces of equipment used for processing the items in the container. For example, a flexible thermal cycler lid seal 430 may be integrated within a wall 450 of the tray 14 as shown in FIG. 4. Such a seal 430 may enclose and define a sleeve or closed channel that receives the lid 1010 (FIG. 11) and be used to allow the thermal cycler lid mechanism 310 to extend the lid into an aperture 14a (FIG. 5) in the sidewall of the tray 14 to cover samples during heating by a thermal cycler block 30, while providing a physical barrier between the lid mechanism 310 and items within the interior area 18 of container 12.

Also, cooling plates 370, 372 may engage portions of an external surface of the tray 14 to impart changes in temperature within the container 12 while not contacting any items within the isolated work area. In some embodiments, cooling plates may engage with portions of the external surface of the tray 14 and/or container 12 to control the temperature of items (such as reagents) held inside the isolated work area/space.

Similarly, as shown in FIG. 3, a cuvette holder 360 can selectively engage a cuvette 660 (FIG. 6) extending from base 240 of tray 14 to perform measurements of concentration and/or volume, but the holder 360 may not contact any items within container 12. Thus, in some embodiments, only the reagents, consumables and tools or devices that are required to directly contact the sample are contained within the isolation container. Such a configuration may have several benefits. For example, a sample can be processed in its own isolated environment and/or the processing equipment residing outside the container will not contact the sample and so is protected from possible contamination. At the conclusion of processing, a desired number of aliquots may be collected in aliquot tubes 440 (FIG. 4) and removed from the container 12, e.g., without compromising the integrity of the collected samples or the isolation container, as will be discussed further below. In some embodiments, for example, the sealed isolation container 12, along with the components contaminated by sample material, can be discarded after a processing cycle.

Figure 6:
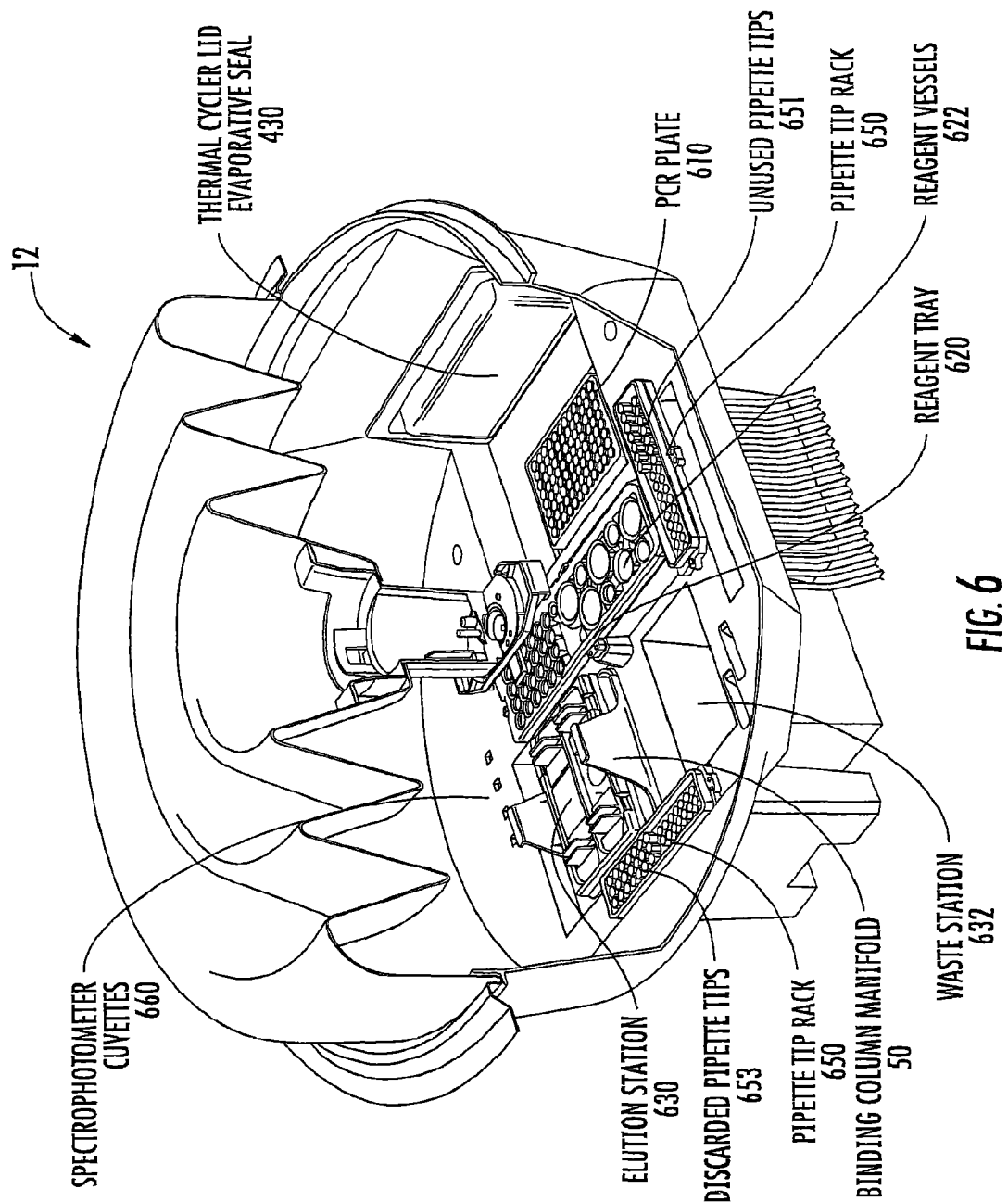
FIG. 6 is a cutaway perspective view of the isolation container assembly of FIG. 5.

FIGS. 5 and 6 show additional details of some components of exemplary isolation containers 12, including the isolation tray 14 and the flexible barrier 16. The interior work area 18 may be surrounded, for example, by base 240 and one or more walls 450. The barrier 16 can include a pipette head 220 or other device or tool, which is described in more detail in a separate section below. The barrier 16 can be configured to cover and seal with the tray 14, for example at a seal 510 along an annular edge 452 of the tray 14, such that the work area 18 is a closed, typically air-tight, compartment when the barrier 16 is sealed with the tray 14.

The tray 14 can be substantially rigid and includes a number of features and/or stations 242 which may be molded, formed, attached or otherwise integrated with tray to accommodate. Some or all of the following components are examples of features that may be integrated into the tray 14:

- elution 630 and waste 632 stations;
- vacuum inlets and outlets;
- spectrophotometer (concentration) cuvettes 660 (FIG. 19A);
- other vessels or cuvettes, e.g., volume measurement cuvettes 2060 (FIGS. 20A-E);
- a thermal cycler PCR plate 610 and/or other substrate or vessel that may be heated and/or cooled with a temperature control device;
- reagent vessels 622 in a rack 620;
- pipette tips 651 in a rack 650;
- one or more additional tip racks 650 or other disposal container, e.g., for used pipette tips 653;
- a binding column manifold 50, e.g., which may include one or more binding columns for nucleic acid processing; and
- one or more aliquot tubes 440 for processing outputs: e.g., nucleic acids, such as (e.g., DNA, RNA, tumor total RNA and/or amplified tumor in vitro transcribed RNA and the like), microorganisms, cells, medicaments, etc.

In some embodiments, the flexible barrier 16 seals with and supports a manipulation tool that interfaces with the robotic device 20 on one side of the barrier and interfaces with internal components on the inside of the barrier 16. The tool can include the pipette head 220 and additional manipulation features, such as handles 520 or other features or mechanism for engaging internal components, such as, for example, handles 50h (FIG. 5) on a binding column manifold 50 for transferring the manifold between the waste and elution stations 632, 630, respectively. The flexible barrier 16 can allow the pipette head 220 to move sufficiently to access all desired internal components housed by the tray 14. The head 220 can also engage the binding column manifold 50 to be able to transfer the binding column manifold to and/or from the waste 632 and elution 630 stations. Although not shown, the internal interface may be a plurality of serially attachable interfaces. That is, the pipette head or first interface can be releasably held and interchanged for another manipulation tool inside the closed container. The selection of manipulation tools can be held by tray 14 and/or an internal manipulation tool rack (not shown).

A mixer and/or centrifuge may cooperate with or be integrated into the tray to mix, homogenize, separate or otherwise blend or process a liquid or sample, such, as for example, a biological sample or other materials as desired (not shown). In other embodiments, the starting material may be pre-mixed, and then placed in the rack 620 or at another location. The mixer may be a rotating head mixer, a magnetic mixer or a homogenizer that can mix the desired material.

Exemplary Pipetting Systems

Figure 7A:
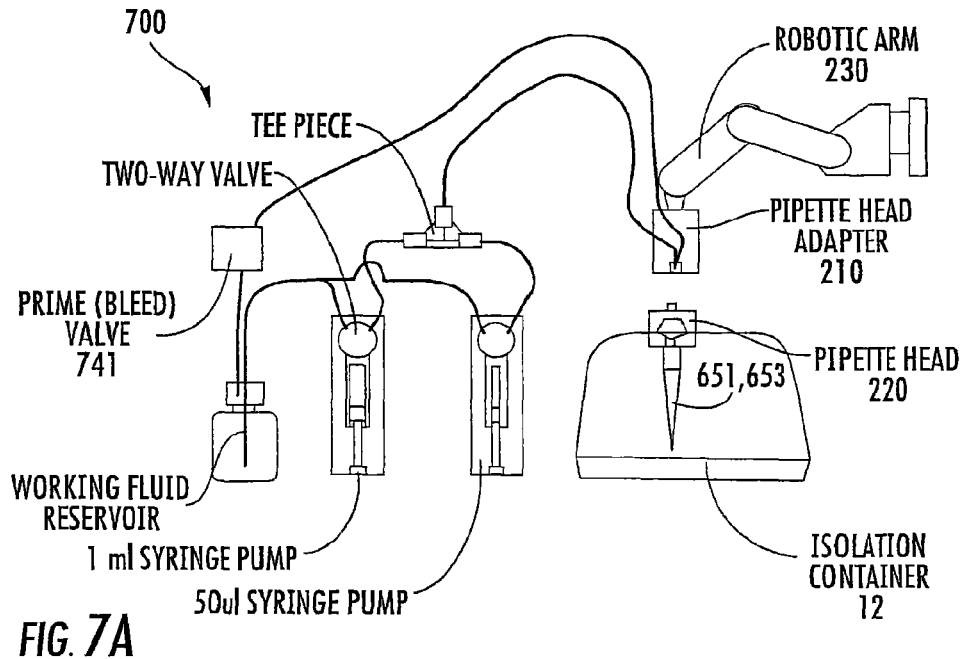
FIGS. 7A and 7B are side views of a syringe pump system according to embodiments of the present invention.

Referring to FIGS. 7A and B, a pipetting system 700 comprising a pipette head 220 and adapter 210 assembly may be used to perform fluid transfers inside the isolation container 12. In keeping with a closed isolation container design, the pipette head 220 can be configured to maintain a barrier between the fluid being transferred and the pipette pump mechanism. A filter and/or a flexible diaphragm 710 can provide the physical contamination-resistant barrier between the interior of the isolation container 12 and the outside.

Figure 7B:
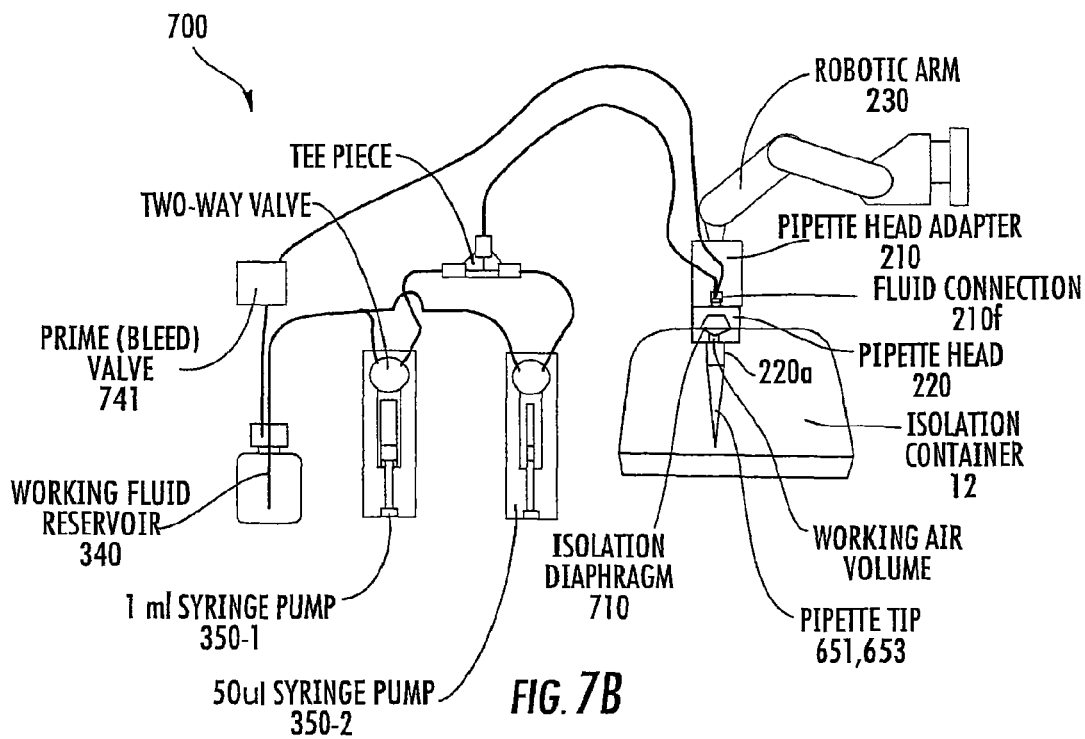

In some embodiments, to provide high volumetric accuracy, the pipetting system 700 may use two positive displacement syringe pumps 350-1, 350-2, e.g., one for low volume transfers (e.g., between about 1 μl and about 50 μl) and one for the higher volumes (e.g., between about 51 μl and about 1000 μl). In other embodiments, a single pump chamber with different reservoirs or a single reservoir with a means of metering the working fluid can be employed. The pump chambers may be hydraulically connected to the flexible diaphragm 710 via (substantially rigid) tubing and a buffer solution (working fluid). The buffer solution can be a substantially or totally incompressible hydraulic fluid that can reduce or minimize the elasticity of the pipetting system 700. The robotic arm 230 is used to position the pipette head 220 at desired locations in the workspace. To reduce the potential for reagent carryover during pipette transfers, disposable tips 651 may be used for fluid handling. That is, after each transfer, the used tip can be discharged into a "trash" receptacle, typically into a used rack, and a new sterile different tip from a sterile rack or supply station may be used for the next transfer. Other components of an exemplary embodiment of the pipetting system 700 are shown in FIGS. 7A and 7B.

In some embodiments, the pipetting system 700 is primed to introduce liquid and remove air from the pipette line prior to initial use, and may be primed prior to each time a different pipette head 220 is connected to the pipette head adapter 210, such as at the beginning of processing of a new closed container 12. For example, a bleed line connects a bleed port in the pipette head to the working fluid reservoir via a solenoid valve 741. The valve 741 may be opened during the priming sequence to allow air to be bled from the pumps 350, through the fluid lines 222, 223 (FIG. 8A) and pipette head 220, and back to the working fluid reservoir 340. The robotic arm 230 can be directed to orient the fluid lines in the pipette head 220 so that they are angled during the priming. Once the system 700 is primed, the bleed valve 741 may be closed and the pipette head 220 is ready to perform fluid transfers. At the completion of the RNA process, the bleed valve 741 may be used to drain the fluid lines 222, 223 and pipette head 220. Filling the fluid lines with air may prevent the possibility of fluid spills during disconnection of the pipette head.

Figure 8A:
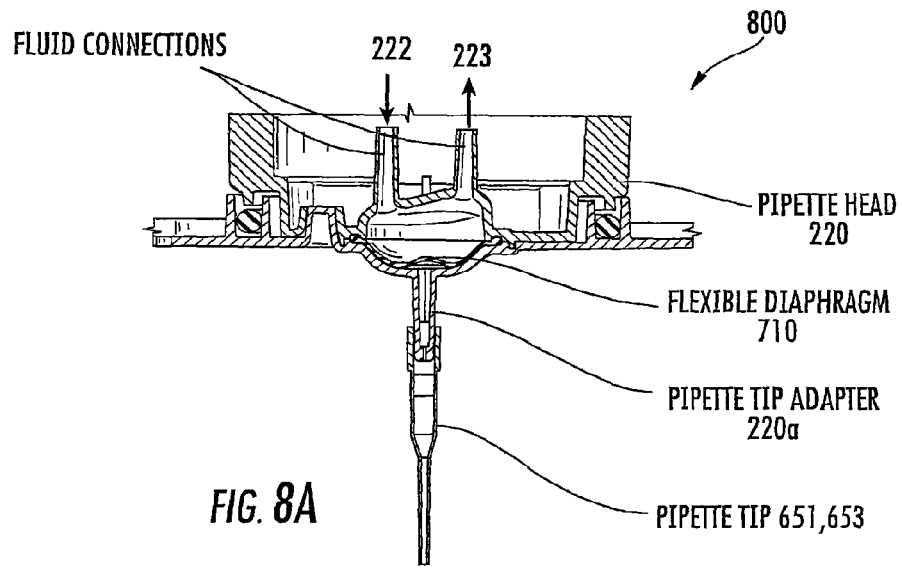
FIGS. 8A and 8B are cross-sectional side views of a pipette head adapted to cooperate with a fluid pump system according to embodiments of the present invention.
Figure 8B:
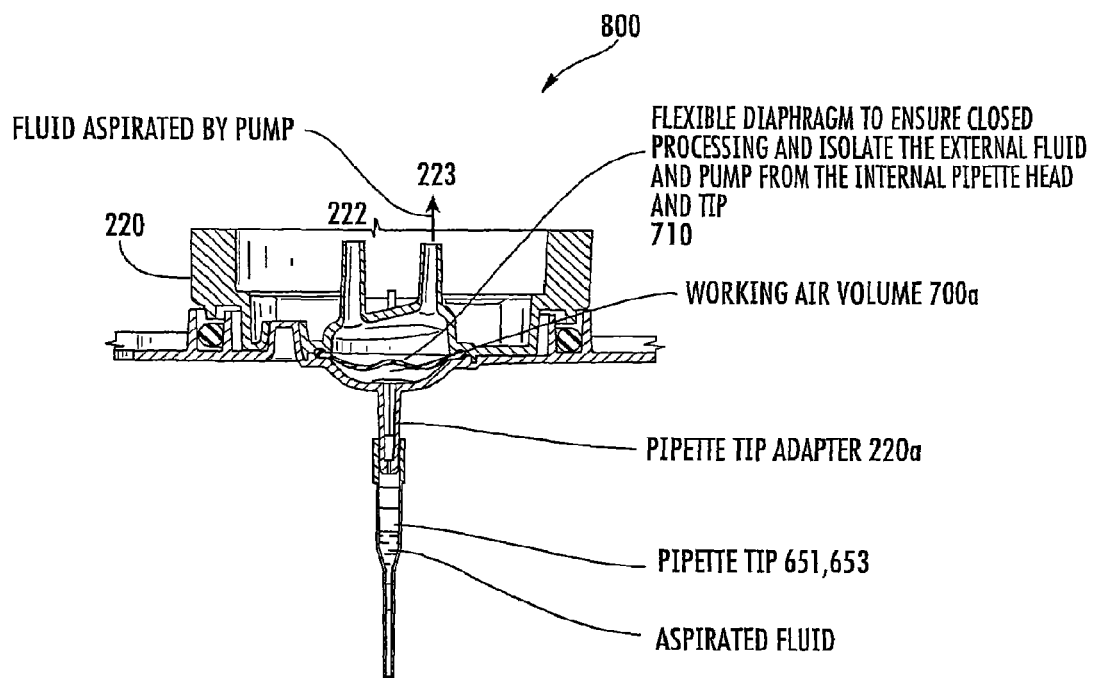
Figure 8C:
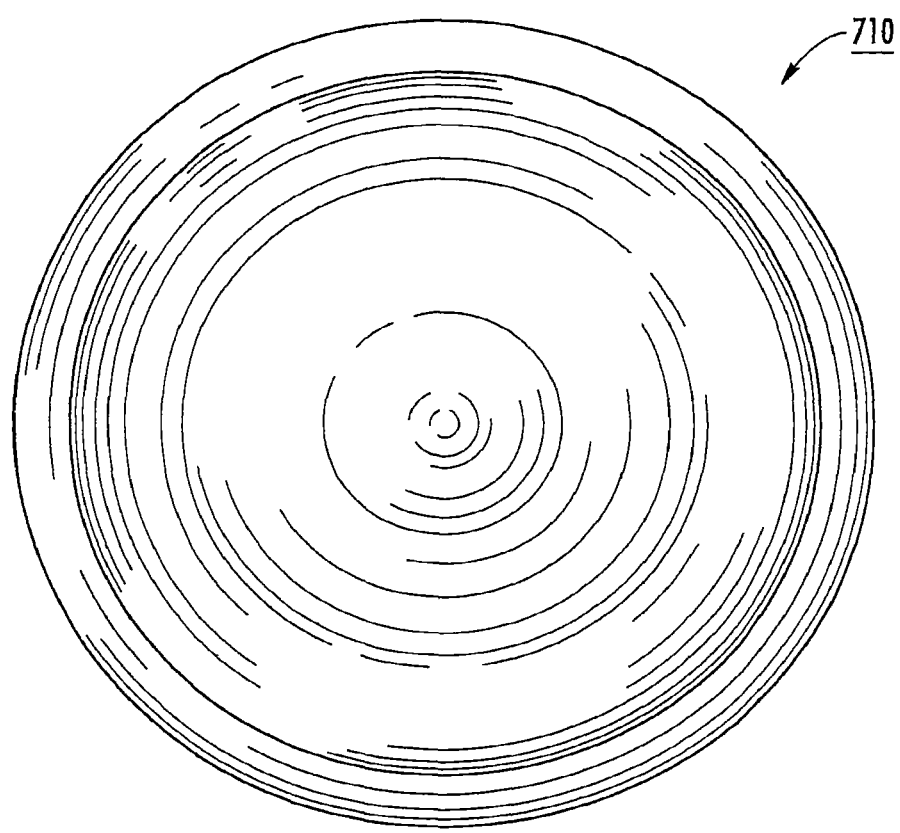
FIG. 8C is a top view of a flexible isolation diaphragm used in the pipette head of FIG. 8A, according to embodiments of the present invention.
Figure 8D:
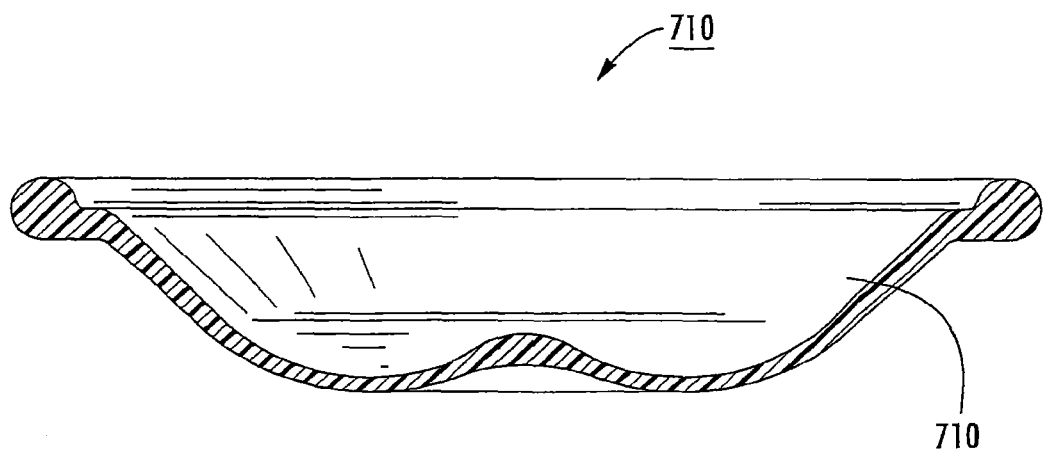
FIG. 8D is a cross-sectional view of the flexible isolation diaphragm shown in FIG. 8C.
Figure 15:
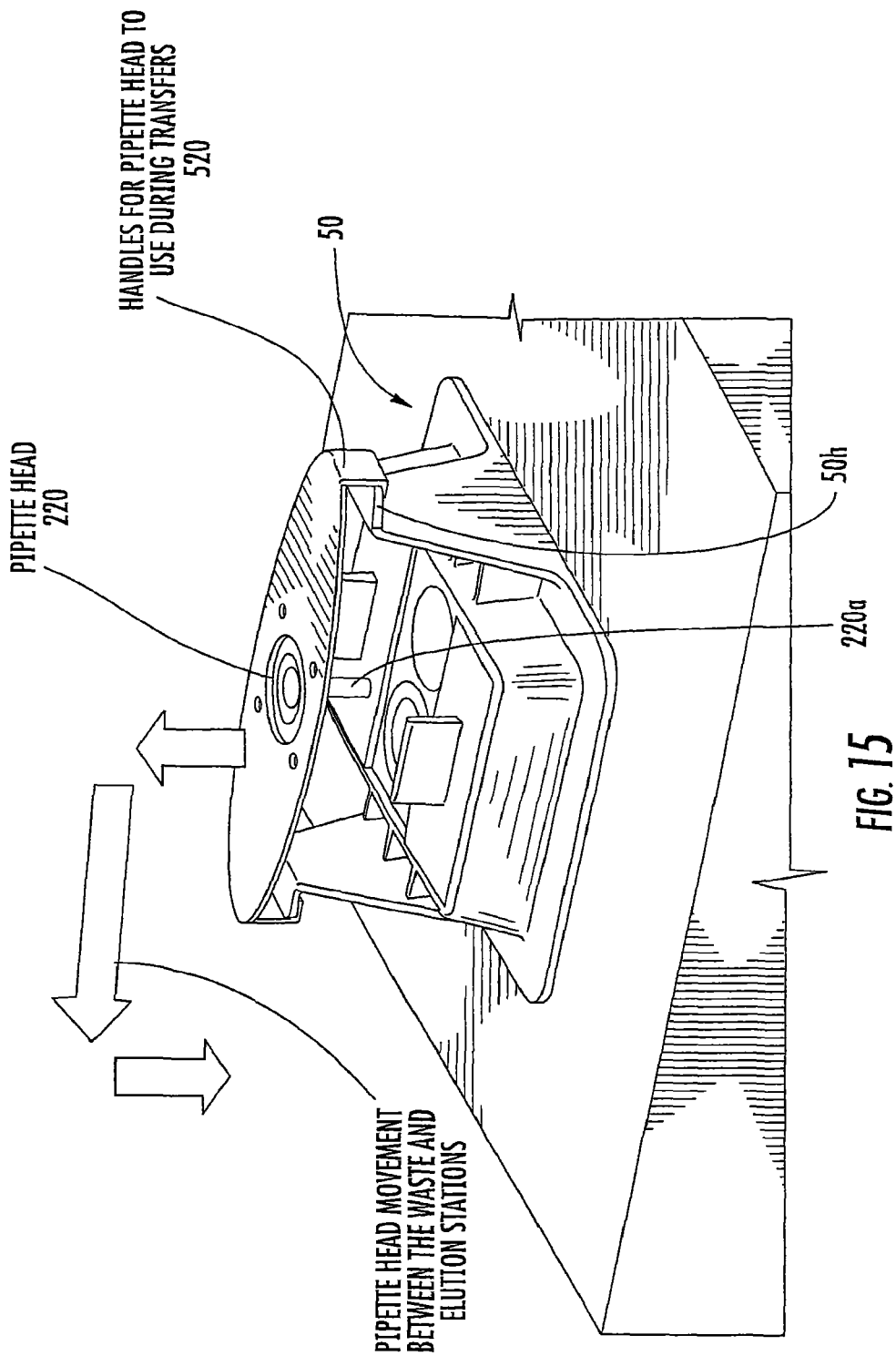
FIG. 15 is a perspective view of the manifold of FIG. 14 during engagement with a pipette head to move the manifold between stations according to embodiments of the present invention.

FIGS. 8A and 8B show a cross-sectional view of the operation of a pressure transfer mechanism 800 for transferring pressure through the pipette head 220 and to the pipette tips 651, 653. In some embodiments, the hydraulic working fluid, e.g., from reservoir 340, actuates the flexible isolation diaphragm 710 (see also FIGS. 8C and 8D) and drives the pipetting action while maintaining physical separation between the working fluid and the fluids to be aspirated by the pipette. A reservoir of working fluid can reside on one side of the diaphragm 710, which is sealed from working air on the other side. The flexible diaphragm 710 resides in the head 220 between the working fluid 340 and the internal pipette tip adapter 220a (i.e., pipette head) and aspirated fluid. FIG. 15 illustrates the adapter 220a without the diaphragm and upper assembly.

Referring again to FIGS. 8A and 8B, displacement of the diaphragm 710 affects the working air volume 700a under the diaphragm 710 and in the pipette tip adapter 220, thereby causing the pipette tip to intake or discharge (typically meted) amounts of liquid. The overall elasticity of the pipetting system 700 may be directly related to dispense accuracy. In some embodiments, reducing the air volume 700a can improve both the pipetting accuracy and precision.

In some embodiments, to facilitate thorough mixing of fluids within reagent vessels, spectrophotometer cuvettes 660 and PCR wells, a repeated aspirate/dispense cycle can be employed and/or the robotic arm 230 can be directed to move the tip of the pipette in multi-axis translation.

Figure 26A:
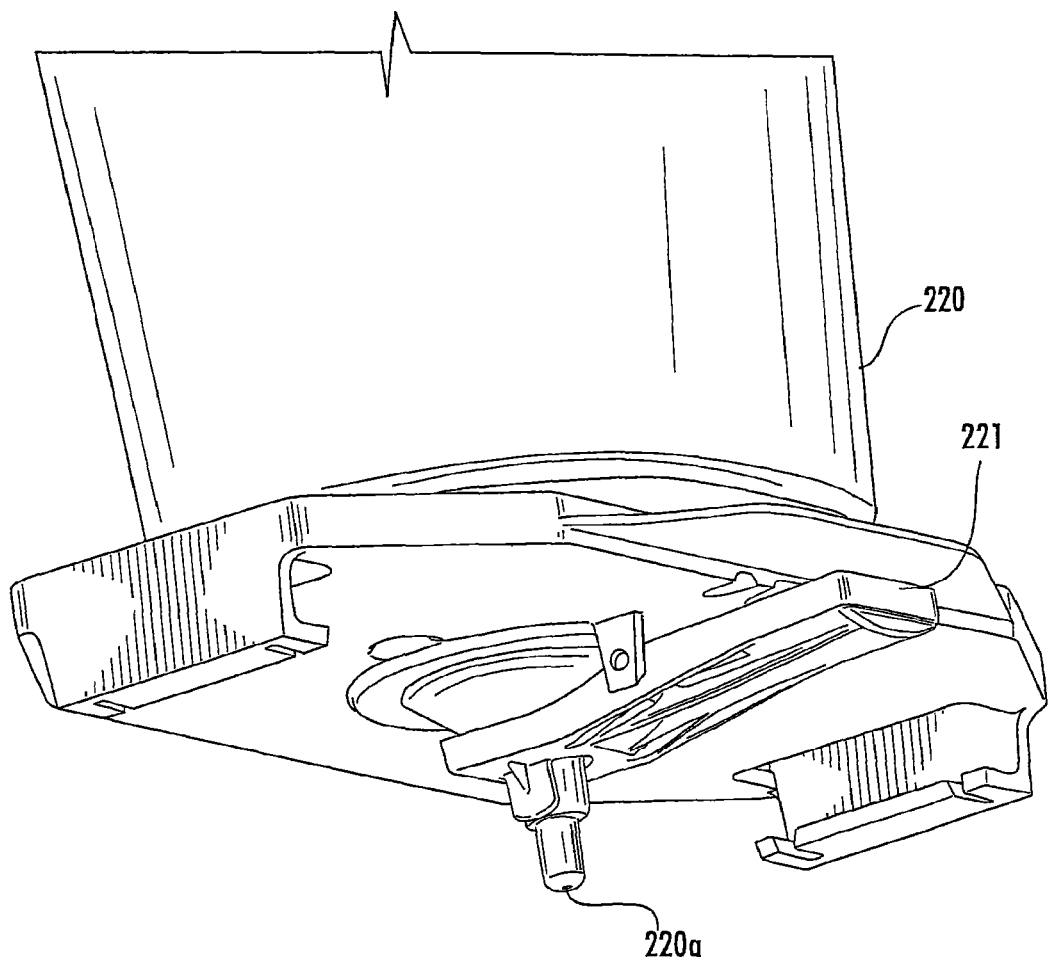
FIGS. 26A and 26B are enlarged side perspective views of the pipette head with lever according to embodiments of the present invention.
Figure 26B:
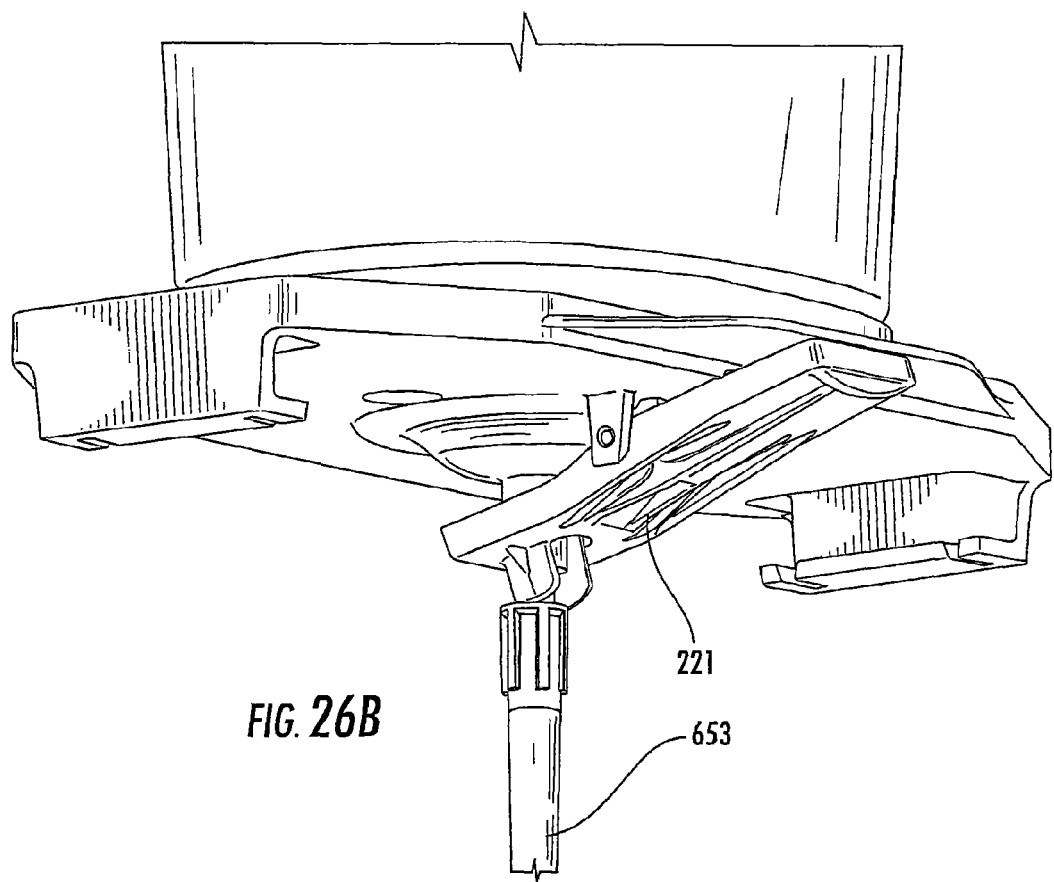
Figure 26C:
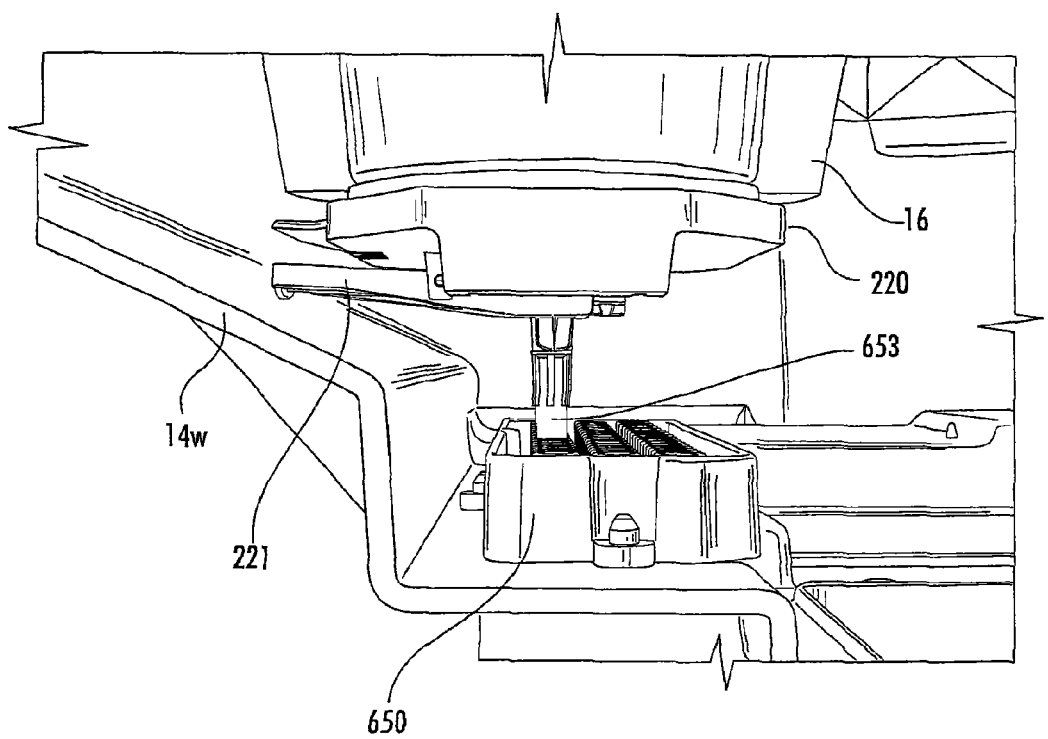
FIG. 26C is a side perspective view of the lever shown in FIGS. 26A and 26B shown engaging with an interior surface of the container to release a pipette tip according to embodiments of the present invention.

In some embodiments, the tray 14 and/or pipette head 220 may include one or more features to allow used tips 653 to be removed from the pipette tip adapter 220a (FIG. 8B). As shown in FIGS. 26A-26C, the pipette head 220 can include a lever 221 that pivots upon contact with a portion of the container proximate to the used pipette rack 650. As shown in FIG. 26C, the container sidewall 14w or a member held thereon can be angled so that upon contact with the outer end of the lever 221, the lever 221 pivots and pushes the used pipette tip 653 off the adapter 220a and into a receiving space in the rack 650. That is, as the pipette head 220 moves downward toward the used rack 650, the lever 221 contacts the wall 14w, which forces one end of the lever upward and the end over the pipette tip 653 downward to push the used tip into the rack 650. Other release configurations may also be used. For example, the used rack 650 may be configured to restrict upward movement of the pipette tip 653 to pull, push or otherwise force or strip the tip from the adapter 220a.

The pipette head 220 and/or adapter 210 may attach to fluid lines and load cell wiring which can be elevated to clear the flexible barrier 16, and a flexible conduit back to the chassis 70. The load cell wiring communicates with a load sensor in communication with the sterile or new pipette tips. The load cell provides data used to control the loading of new pipettes onto adapter 220a. For example, the robotic arm can cause the pipette head 220 to advance down with a force between about 5N to about 50N to indicate the pipette tip 651 is properly attached. Adapter 210 can also include a collar for locking and unlocking the adapter 210 to the pipette head 220, e.g., as a non-limiting alternative to an engage/release handle mechanism.

Exemplary Flexible Barriers

FIGS. 9A-9E illustrate exemplary flexible barriers 16 according to embodiments of the present invention. Any suitable material can be used for the barrier. The barrier 16 can be substantially impermeable to air, moisture, and ethanol vapor. The barrier 16 may be moldable without losing sufficient flexibility or impacting permeability. In some embodiments, the barrier 16 comprises a low-density polyethylene, but other alternatives could include a range of urethane materials. In particular embodiments, the flexible barrier is or comprises an "ARMORFLEX" material, available from ILC Dover Company, located in Frederica, Del.

The formed shape of the flexible barrier 16 can allow sufficient robot movement and give the pipette head (or other internal interface) access to the interior of the isolation container 12 without restriction or otherwise pinching or catching the flexible barrier. The shape of the molded flexible barrier 16 can be substantially self-supporting (e.g., it will not collapse into the isolation container) once the flexible barrier 16 is sealed to the tray 14 forming the isolation container 12.

Figure 9A:
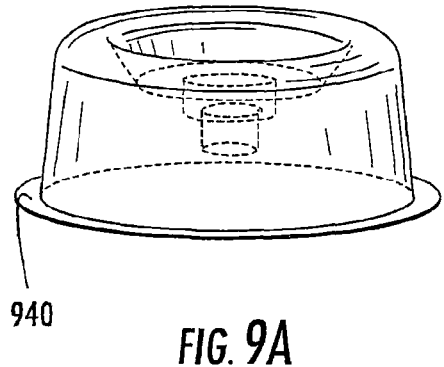
FIGS. 9A and 9B are perspective and cross-sectional views, respectively, of a flexible barrier according to embodiments of the present invention.
Figure 9B:
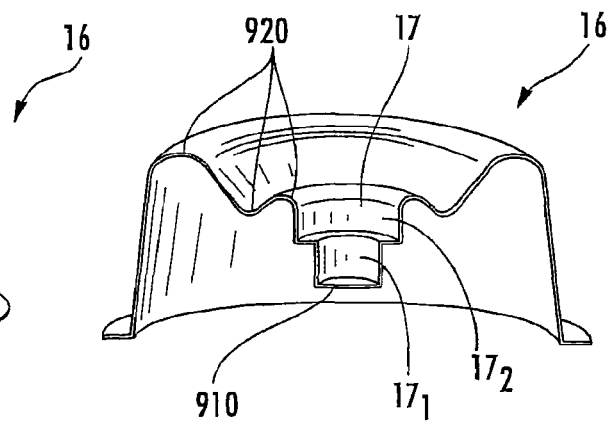

In some embodiments, a portion 910 of the barrier 16 may be adapted to integrate with, receive, hold, attach to, mate with, seal with, support, or otherwise interact with a device for manipulating samples within the container, such as, for example a pipette head 220, another fluid transfer device, and/or another manipulation tool. The portion 910 can be a substantially medial portion. The barrier 16 may include one or more folds, pleats or undulations described as "convolutions" 920, some of which may be substantially concentric with others. FIG. 9B illustrates that the portion 910 may include at least one stepped portion 17, shown as a series of substantially vertically oriented stepped portions $17_1$, $17_2$, $17_3$.

Figure 9C:
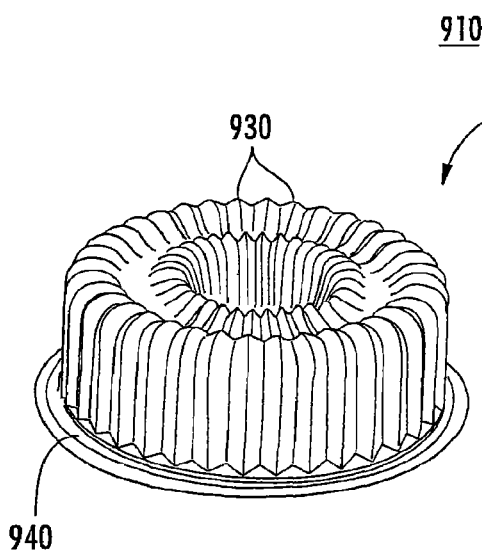
FIGS. 9C and 9D are perspective and cross-sectional side views, respectively, of other embodiments of a flexible barrier.
Figure 9D:
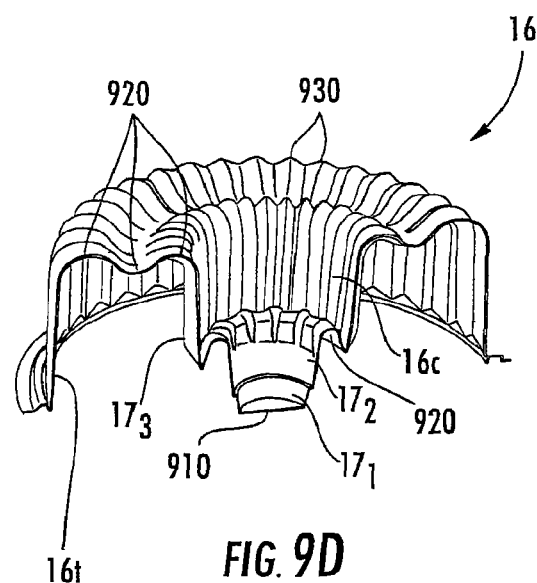

In some embodiments, as shown for example in FIGS. 9C and 9D, the barrier 16 may include one or more radial convolutions 930. The radial and/or concentric convolutions may help facilitate a full range of movement of the pipette head (or other internal manipulation tool interface), and help control the barrier shape during movement of the pipette head. A rim 940, flange or other feature may provide a surface for clamping, sealing, fixing, adhering, or otherwise attaching the barrier 16 to the tray 14.

As shown in FIGS. 9C and 9D, the flexible barrier 16 can comprise a unitary sheet of material that is stretched or formed into a series of substantially concentric folds, pleats or convolutions that can allow for the desired movement of head 220. Outer perimeter regions of the barrier sheet 16t may have a different thickness than a center region 16c. In some particular embodiments, during fabrication, thicker material can be drawn down to the center during vacuum forming causing thinner central regions and thicker perimeter regions of the barrier sheet 16. The center region 16c may include a series of columnated steps $17_1$-$17_3$, arranged smaller to larger as the barrier 16 moves away from the workspace 18. In other embodiments, rather than a unitary sheet of material, the flexible barrier 16 may comprise a plurality of co joined sealed segments of the same or different suitable materials (not shown).

Figure 9E:
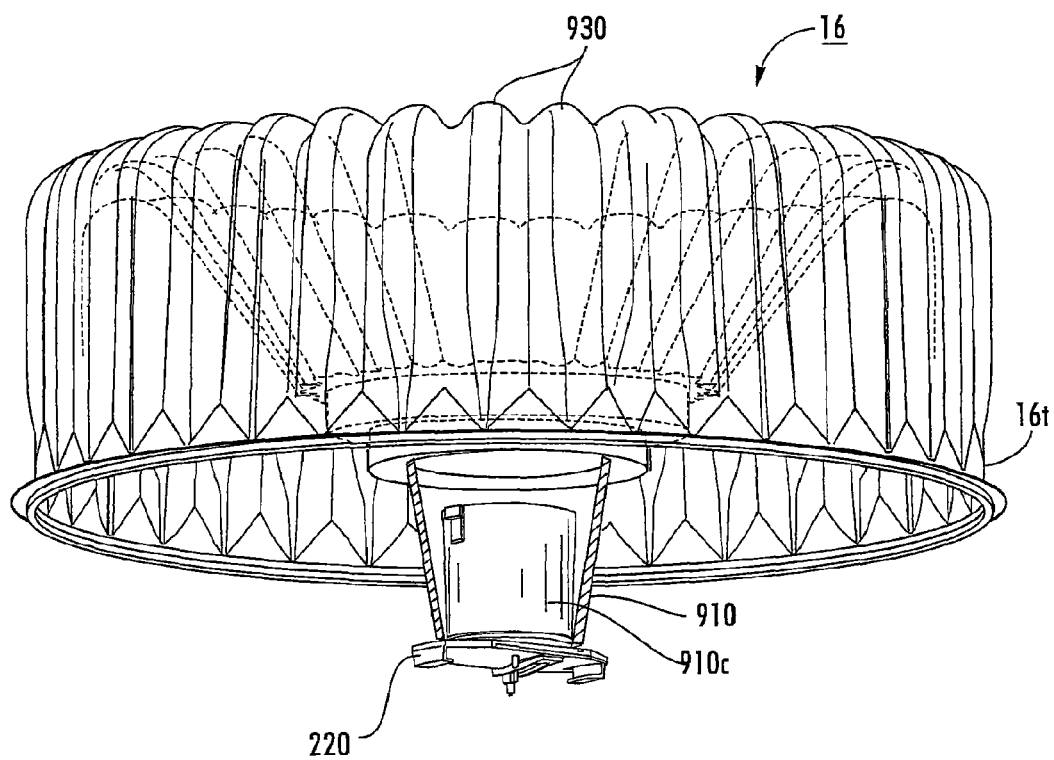
FIG. 9E is a perspective view of a flexible barrier with an integral coupler, the coupler in the barrier shown in partial section view, according to embodiments of the invention.
Figure 9F:
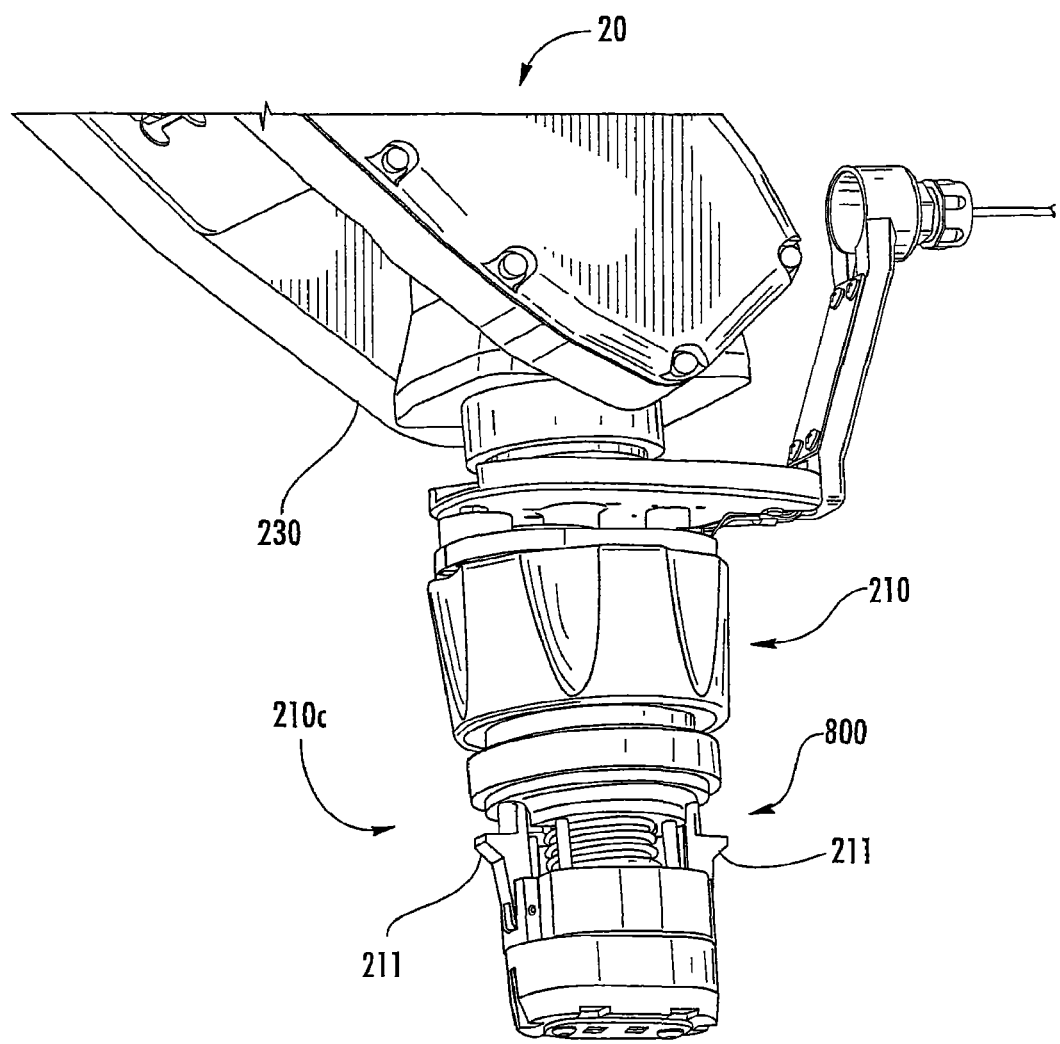
FIG. 9F is a perspective view of a portion of a robotic arm having a coupler configured to engage the barrier coupler shown in FIG. 9E according to embodiments of the present invention.
Figure 9G:
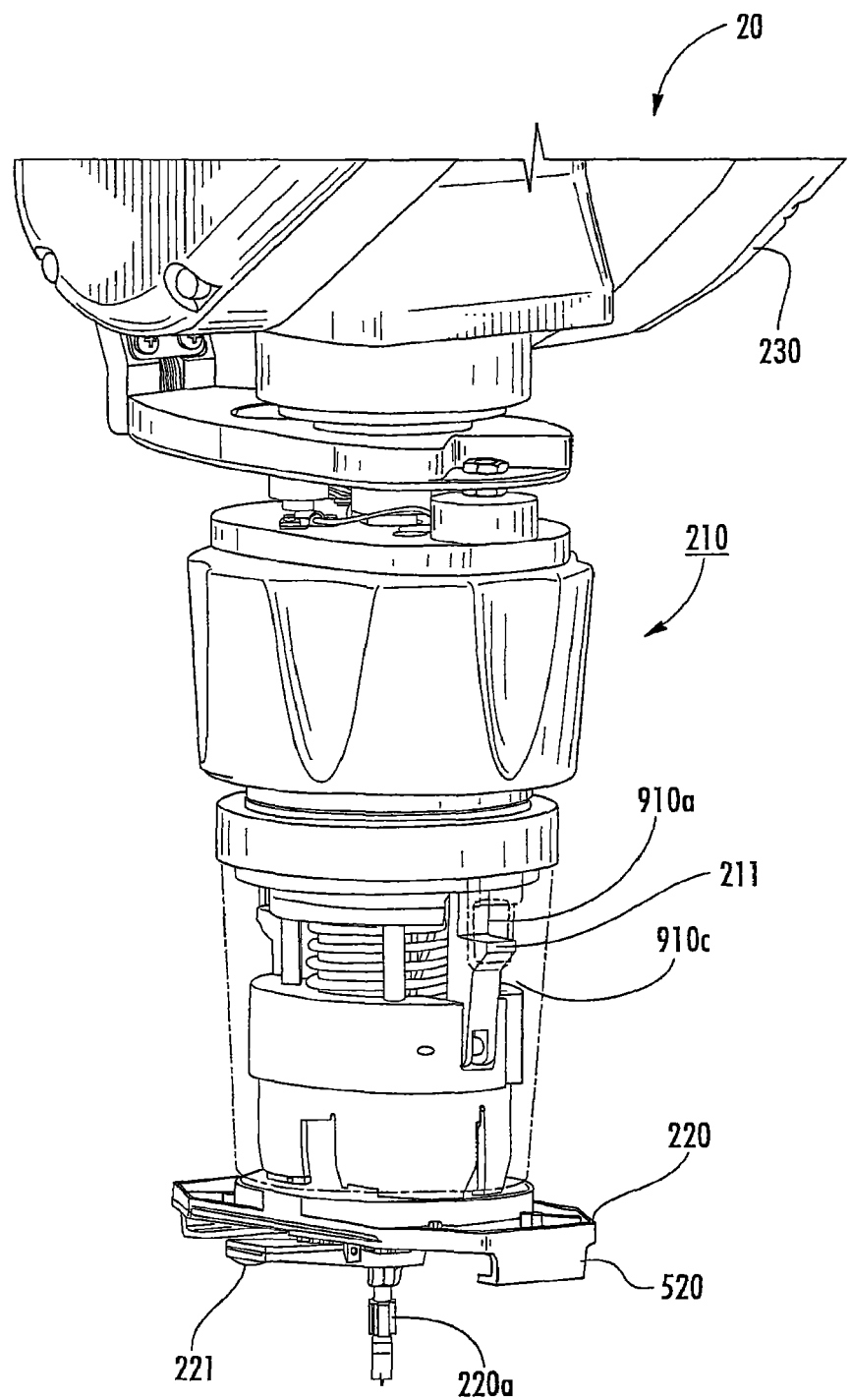
FIG. 9G is a perspective view of the assembly of the components shown in FIGS. 9E and 9F (without the flexible barrier) and with the outer housing over the internal components shown transparent and in broken line.
Figure 9H:
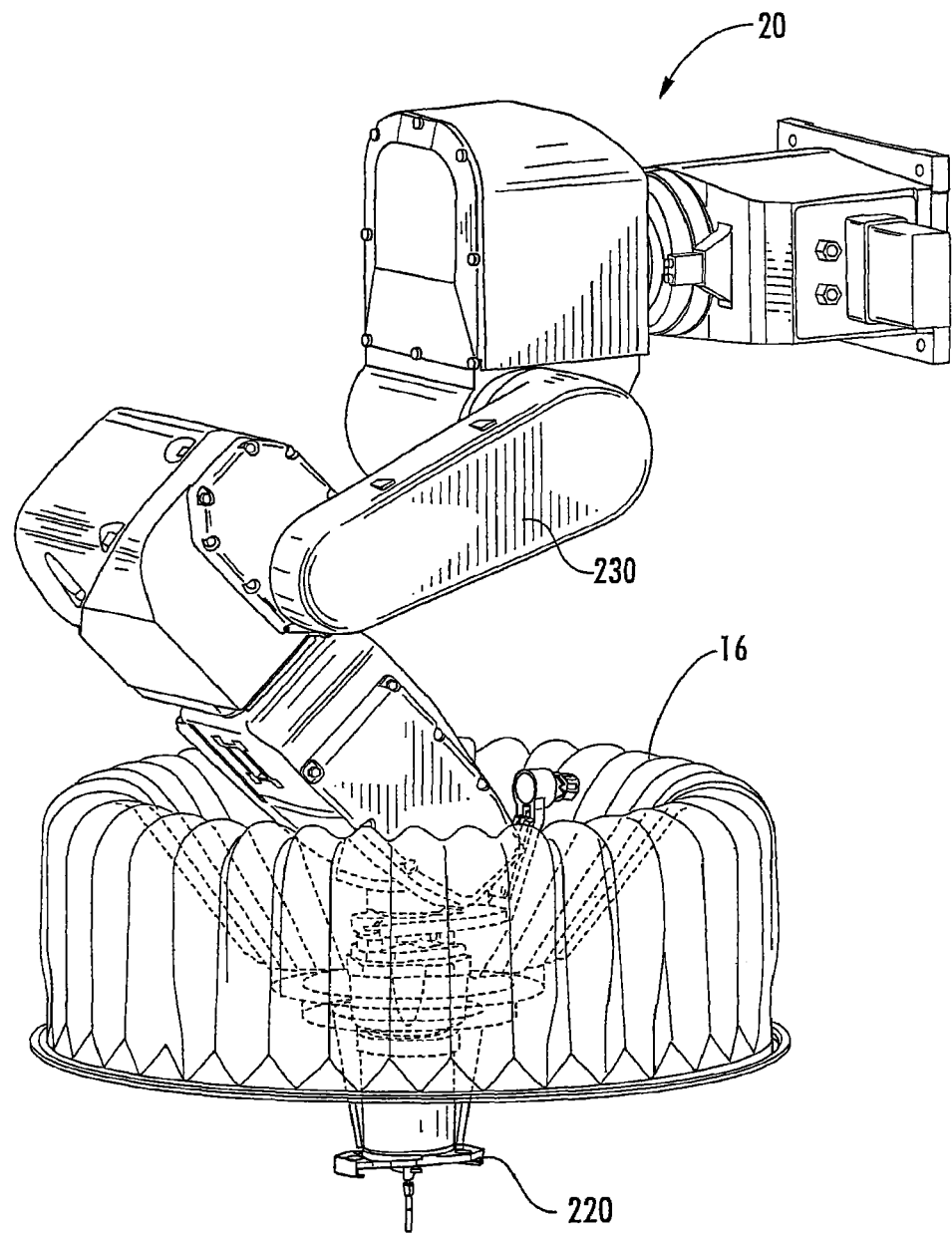
FIG. 9H is a perspective view of the assembly shown in FIG. 9G with the flexible barrier attached according to embodiments of the present invention.

FIG. 9E illustrates the flexible barrier 16 sealably attached to a lower portion of the pipette head 220 for subsequent engagement to the robotic arm 20. A robotic arm coupler 910c resides outside the barrier 16. FIG. 9F illustrates a cooperating coupler 210c that is configured to engage the coupler 910c. As shown in FIG. 9G, fingers 211 are configured to enter apertures in the coupler body 910a to releasably engage the barrier 16. The assembly is shown in FIG. 9H (without the lower container tray 14).

Exemplary Thermal Block Assemblies

Figure 10:
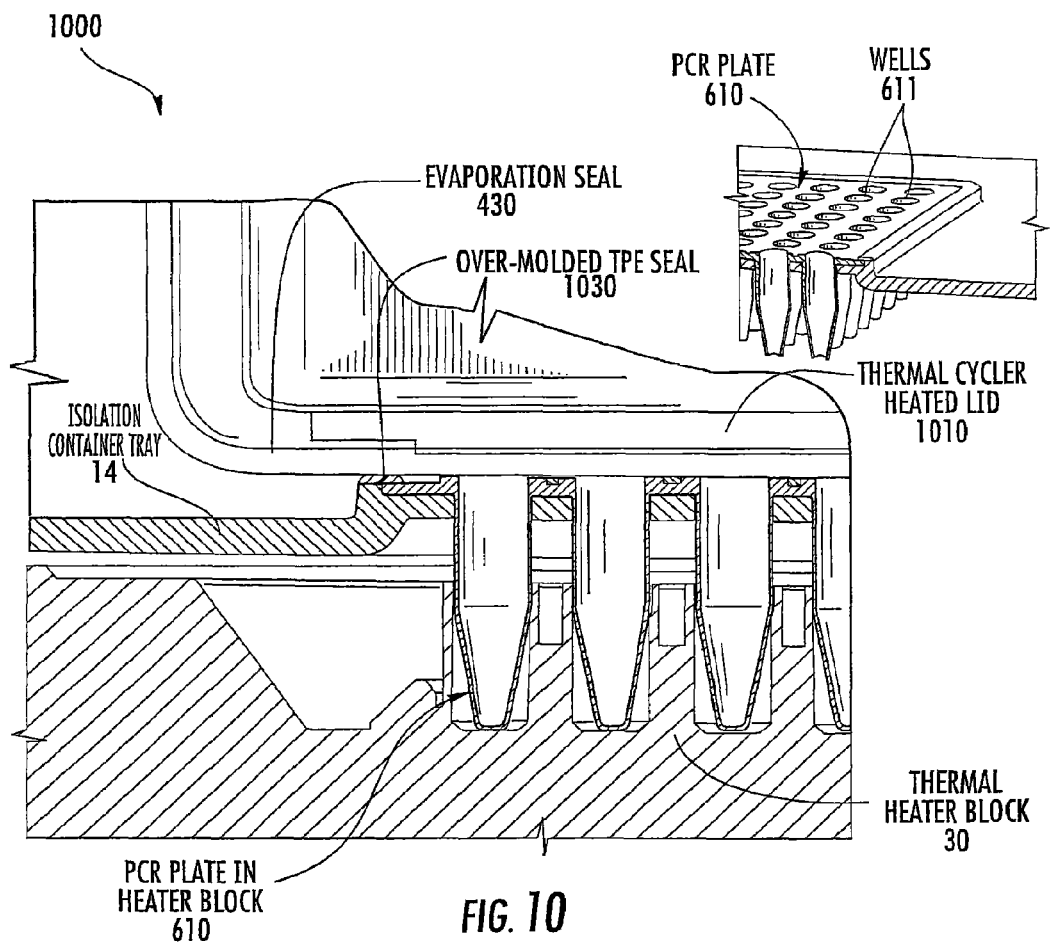
FIG. 10 is a cross-sectional view of a PCR plate and thermal cycler lid assembly according to embodiments of the present invention.

As shown in FIG. 10, a nucleic acid processing system may incorporate a thermal block assembly 1000 or any other temperature control device. For example, a nucleic acid processing system can incorporate a thermal cycler for synthesizing and amplifying nucleic acids. The thermal block assembly 1000 may include, for example, a thermal (heater) block 30, which may be configured to receive a multiwell strip or plate such as a PCR plate 610, and a thermal cycler heated lid 1010 which may be actuated by a lid mechanism 310 to cover the PCR plate 610. For example, in some embodiments, the thermal cycler assembly is used for cDNA synthesis, cDNA amplification, IVT RNA synthesis and DNA removal steps of the process. Various types of thermal blocks and/or thermal cycler devices are available.

As shown in FIG. 10, the PCR plate 610 may be incorporated into the isolation container tray 14. In some embodiments, the perimeter of the PCR plate 610 can be sealed to an open (substantially rectangular) region formed in the base of the tray 14. Lower portions of the plate 610 extend downwardly from the base of the tray to engage (typically reside in) a thermal cycler heater block 30 while the openings of wells 611 in the plate 610 are accessible from inside of the sealed container 12. The PCR plate 610 can be sealed to the isolation container tray 14 so that the downwardly extending portions of wells 611 can be in direct contact with the thermal cycler or temperature control device.

In some embodiments, a compliant gasket, O-ring or other sealing mechanism may be used to attach the PCR plate 610 to the isolation container tray 14. The compliant gasket may be attached with a heat-swaged clamping feature. In some embodiments, an over-molded thermoplastic elastomer (TPE) seal 1030 is used for attaching and sealing the PCR plate 610 to the isolation container tray 14 as shown in FIG. 10. In other embodiments, PCR plate features may be formed, such as molded and/or machined, into the isolation container tray substrate. In other embodiments, a glue, tape and/or adhesive may be used to attach the PCR plate 610 to the tray 14.

A lid, such as a heated thermal cycler lid 1010 may be used to reduce the loss of reaction fluid via evaporation. The lid 1010 may be lined, for example, with a flexible seal 430 to inhibit evaporated fluid escaping from some or each PCR well 611 and/or for maintaining isolation of the interior of the container 12. The lid 1010 can be heated to inhibit vapor condensing on the lid or any surface other than the reaction mixture. To provide access to all of the PCR wells, the thermal cycler lid 1010 may be lifted vertically to release the sealing pressure, then retracted substantially horizontally taking with it the flexible lid seal 430.

Figure 12:
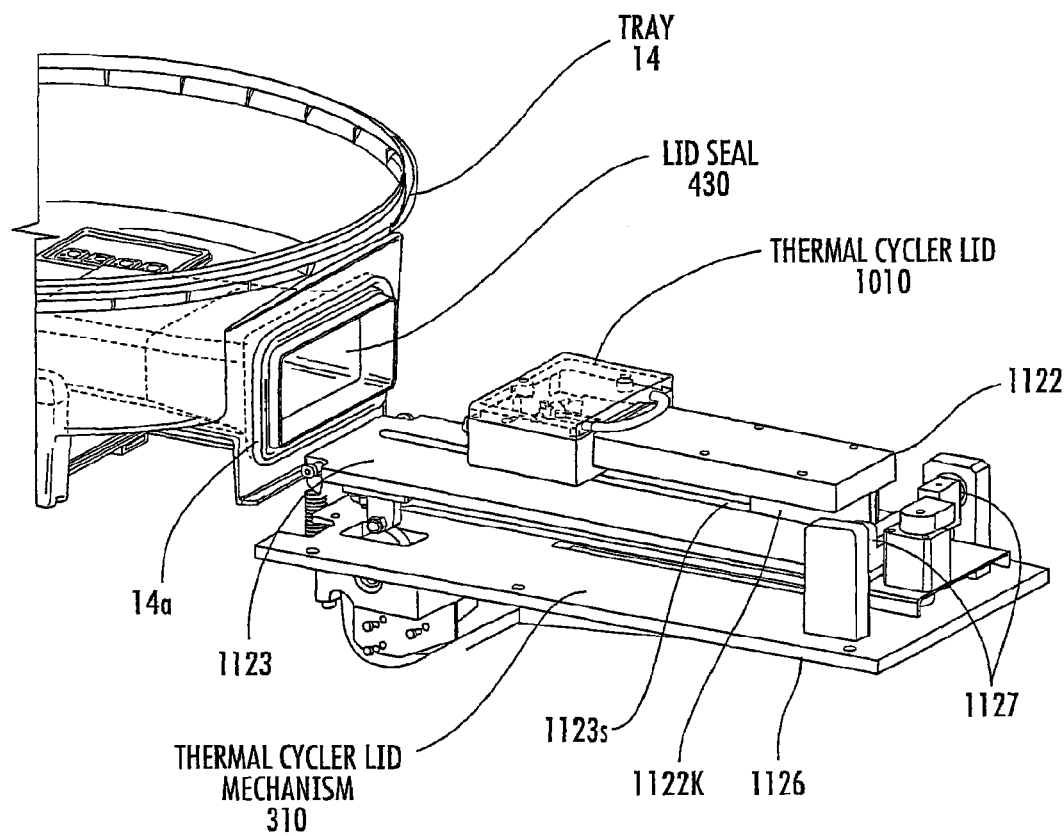
FIG. 12 is a perspective view of the thermal cycler lid drive system of FIG. 11 in use with a flexible thermal cycler lid seal of a container according to embodiments of the present invention.

A drive system 310 for controlling the automatic movement of the lid 1010 may be mounted to the work surface 200 of the processing system 10, as shown in FIG. 3. In other embodiments, the lid drive, system 310 may be mounted at other locations above or below the work surface 200. Referring now to FIG. 11, an exemplary lid drive system 310 is shown with the lid 1010 in the retracted position. The arm 1122 is connected to the lid 1010 and communicates with motor 1150; this provides for movement of the lid 1010 into and out of container 12, e.g., through a side-ingress/egress aperture 14a in the wall of tray 14 where a lid seal (which can be described as a sleeve) is disposed between lid 1010 and the interior of the container as shown in FIG. 12. Robotic tools or manual input may also be via the seal 430.

Figure 13A:
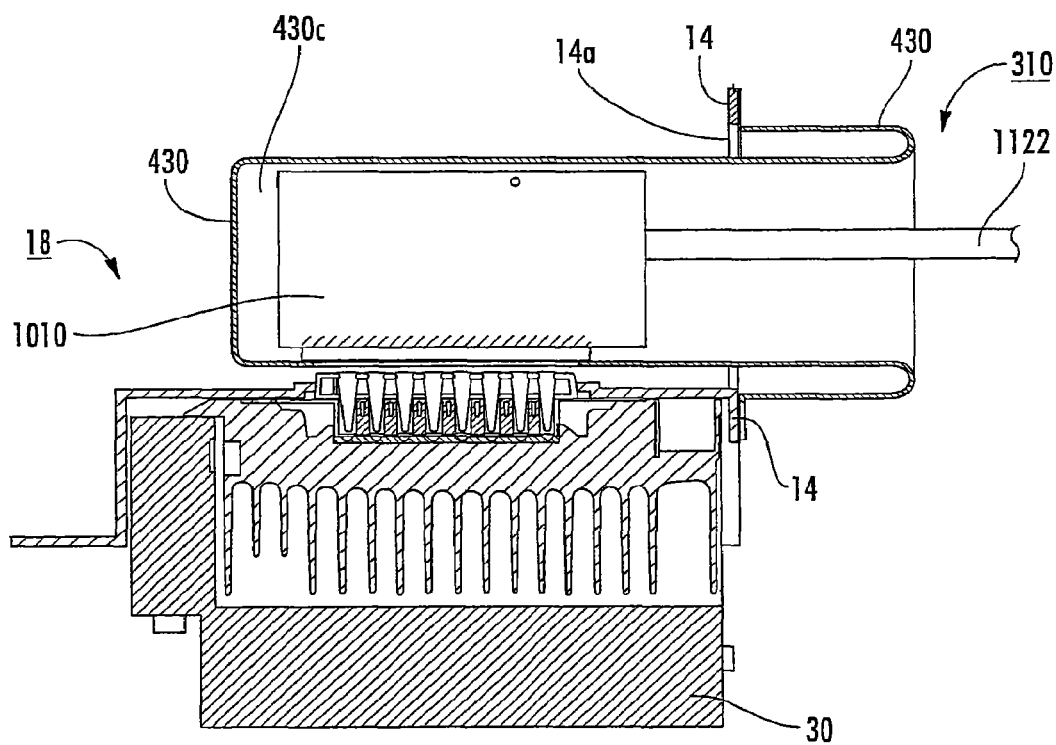
FIGS. 13A and 13B are cross-sectional views of the lid seal of FIG. 12 during movement of the thermal lid into and out of the work space of the container according to embodiments of the present invention.
Figure 13B:
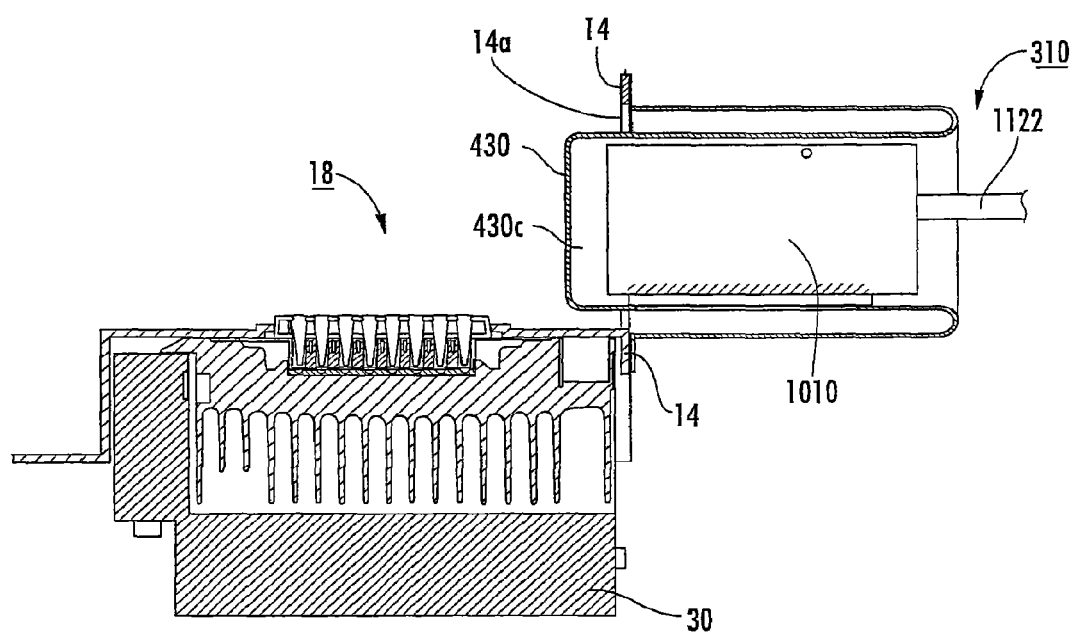

FIG. 13A illustrates an exemplary configuration of the lid 1010 in the container 12 and inside the chamber 430c of the lid seal 430 when extended. FIG. 13B illustrates the lid 1010 outside the container 12 in a retracted configuration.

The arm 1122 can be configured to direct the lid 1010 vertically as well as horizontally. In the embodiment shown in FIGS. 11 and 12, the drive system 310 includes a vertical movement mechanism 1124 that provides for vertical movement of the lid 1010, e.g., when lid 1010 is positioned over the PCR plate 610 within the container 12. The vertical movement mechanism 1124 may provide a downward force sufficient to seal the lid 1010 with the plate 610 and/or the block 30 (FIG. 10), for example, using one or more biasing members 1152. One or more motors 1150, actuators, gears, linkages or other electro-mechanical devices may be used to drive horizontal and/or vertical movement. As shown in FIG. 12, the drive system 310 includes an upper plate 1123 with a slot 1123s. The arm 1122 includes a keel 1122k that slides in the slot 1123s. The drive system 310 also includes a lower plate 1126 that is attached to the upper plate 1123 via pivots 1127 and biasing members 1152. The vertical drive 1124 is attached to the upper and lower plates 1123, 1126 and is configured to pull the upper plate 1123 down to force the lid 1010 down once the lid 1010 is in the extended configuration inside the container.

A portion of the drive system 310 can be physically attached to the interior surface of the sleeve or lid seal 430 to facilitate the seal 430 moving appropriately with the lid 1010. As shown, in FIG. 11, in some embodiments vacuum cups 1140 may be incorporated onto the lid 1010 to engage the flexible lid seal 430 and to cause the seal 430 to remain in position during vertical and horizontal movement of the thermal cycler lid 1010. In other embodiments, the lid seal 430 may be attached in other ways or may be sufficiently flexible to conform to the lid 1010 and move in concert therewith.

Figure 13C:
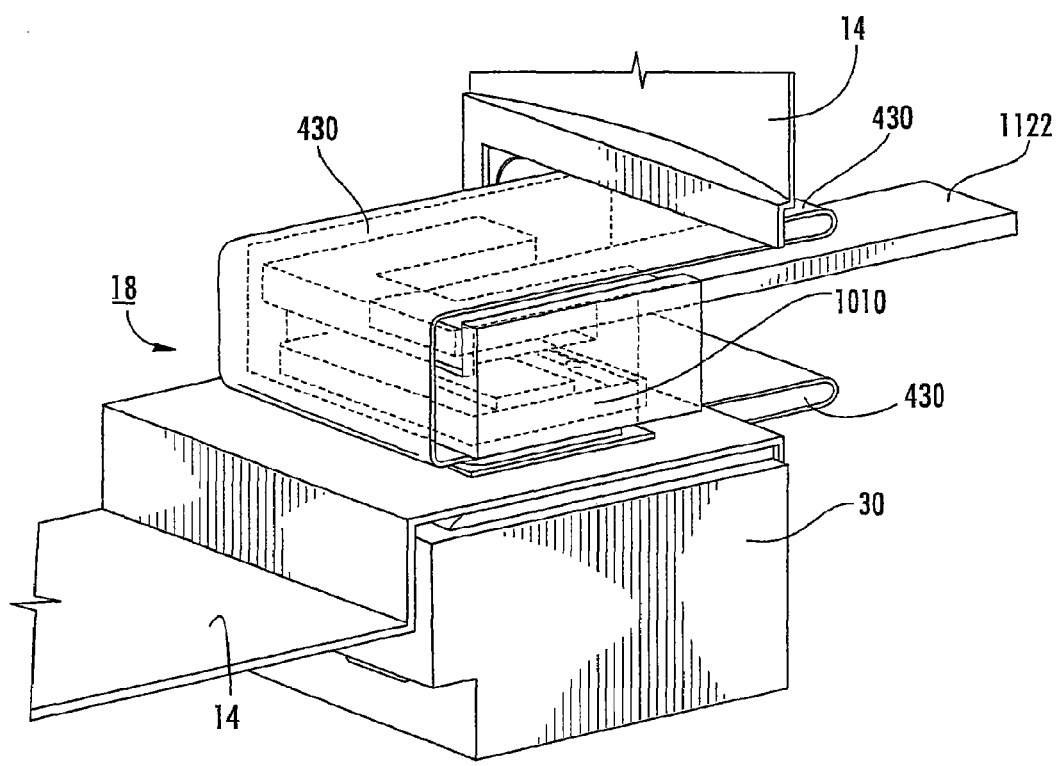
FIG. 13C is a partial cutaway side perspective view of the lid seal and container shown in FIGS. 13A and 13B.

In some embodiments, to facilitate a reliable seal between the isolation container 12 and the flexible lid seal 430, a clamp plate or other clamping member may be used to compress against an edge portion of the seal 430, such as via one or more sealing ribs (not shown) on the lid seal against the outside wall of the tray 14. In other embodiments, the lid seal 430 may be over-molded to the tray 14 using, for example, TPE as discussed above with respect to the PCR plate 610. O-rings, gaskets, adhesives, tapes, and mounting or sealing members may be used to provide the sealed connection of the lid seal 430 and the tray 14. FIG. 13A shows the lid mechanism 310 with the lid 1010 and the seal 430 extended into the interior region of the tray 18 in an engaged position while FIG. 13B shows the lid 1010 and retracted out through a wall of container 14. FIG. 13A illustrates the lid 1010 in position over a thermal cycler and 96-well plate. FIG. 13C illustrates a partial side perspective cutaway view of the lid mechanism 310 with the lid 1010 extended into the interior region of the container 18.

Exemplary Waste and Elution Systems

Various purification means can be used to process samples, such as nucleic acids, proteins, cells, tissues, and the like. Such purification devices include, but are not limited to, magnetic beads, size exclusion membranes, binding plates, filters, and binding columns. Such devices are known to those of skill in the art.

In one embodiment, the processing system 10 uses a technique of eluting from binding columns for tumor total RNA isolation, cDNA purification and IVT RNA purification. The binding column 1410 (FIG. 14) can contain a silica membrane. A vacuum elution protocol can be integrated into the isolation container design. In other embodiments, a magnetic elution protocol can be integrated into the container.

One or more types/sizes of binding columns may be used. For example, in some embodiments, binding columns (e.g., Qiagen RNeasy™ columns) are used as they have a binding capacity suitable for the quantities of RNA, cDNA and IVT RNA that are processed. An additional, smaller Qiagen "Mini" column can be included to provide the ability to concentrate the RNA.

To inhibit the waste fluid from contaminating the elution vessels, the waste and elution stations 632, 630, respectively, can be separate as shown for example in FIG. 6. In some embodiments, a manifold 50 is used to hold the binding columns (see FIGS. 14 and 15). The manifold 50 can be configured to hold one or more binding columns of various sizes/types, e.g., Qiagen maxi-, midi- and/or mini-binding columns 1410. The manifold 50 may include wells 50w for each binding column, lifting members or arms forming lift members 50h for the pipette head 220 to lift it, and one or more slidably movable lids 1430 that can be used to close off the unused binding columns. The lids 1430 can include a handle 1430h that can allow the head 220 to slide the lid 1430 in a desired direction. In other embodiments, a manifold 50 may be configured to hold other types of substrates or devices to be used during a desired process. The lift members 50h can be configured as any suitable lift, including one or more handles (as illustrated), wings, flanges, or other features to facilitate movement of the manifold 50 between stations.

FIG. 15 shows an example of a mechanism and method for moving a manifold 50 between two or more stations or area of the container 12, e.g., between the waste and elution stations 632, 630, respectively. The pipette head 220 and robot 20 may be used to move the binding column manifold 50 and the columns 1410 to and from, i.e., between the two stations. In the embodiment shown, the manifold 50 may include handles 50h, wings or other features that interface with corresponding features 520 on the pipette head 220, and are used to simplify the engagement between the robot 20 and the binding manifold 50.

Each isolation and purification process can use a different set of columns; the pipette head robot may be used to reposition the lids 1430 to close the appropriate set of unused columns. This reduces or minimizes the airflow through the manifold 50, allowing the pump to generate a sufficiently high vacuum during the isolation and/or purification processing steps. To reduce operator handling of the binding columns 1410 after sterilization, the columns 1410 may be loaded into the manifold 50, and the assembly sealed into suitable packaging and gamma-sterilized in the manifold 50. At the time of loading the isolation container at a use and/or assembly facility (such as in a suitable clean room), an operator can remove the packaging from the manifold 50 and place it into the waste station 632, without ever needing to directly handle the binding columns.

The waste and elution station configurations can be flexible and/or scalable. The manifold 50 design can be large enough to allow modification or use to suit a 96-well format, or any other type of plate, well or columns, or changes in the combination of maxi-, midi- and mini-columns 1410.

Figure 17:
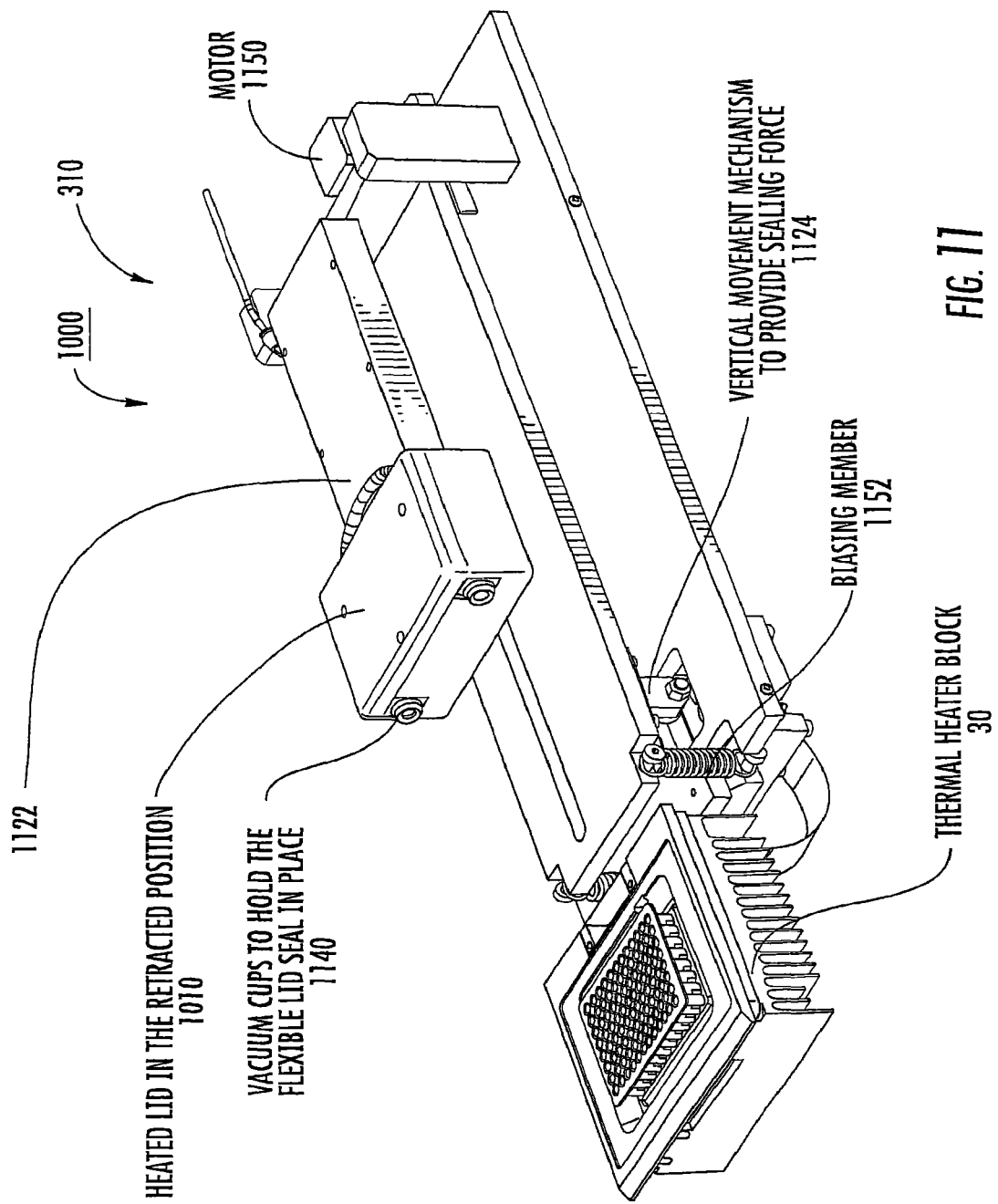
FIG. 17 is a schematic side view of the vacuum system of FIG. 16 during use with the isolation container according to embodiments of the present invention.
Figure 16:
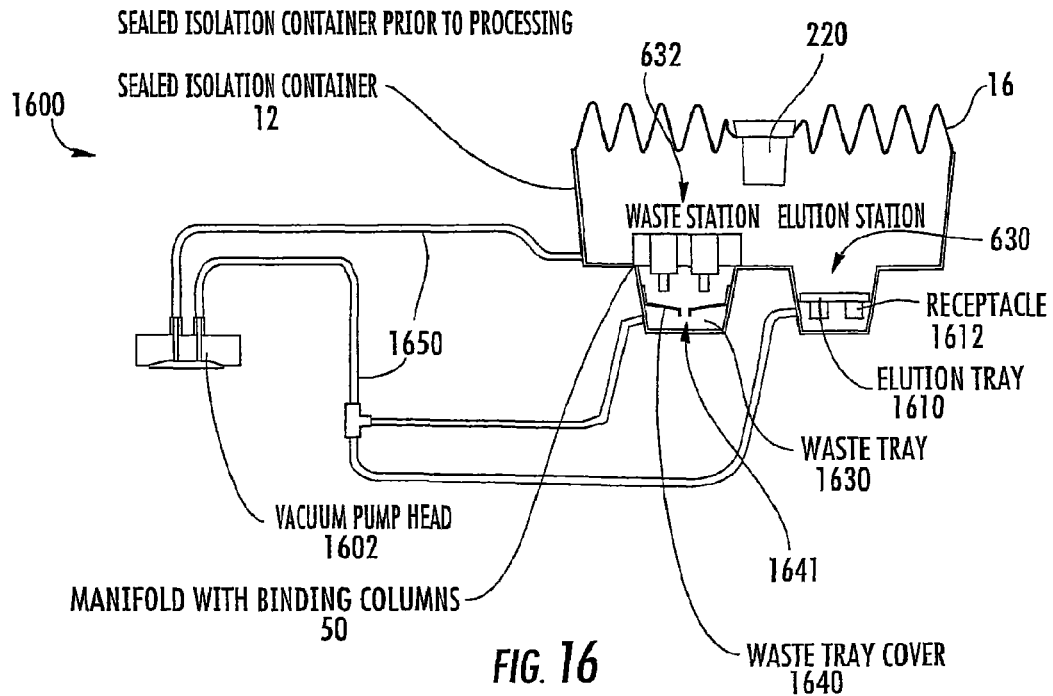
FIG. 16 is a schematic side view depicting a closed vacuum system prior to use with an isolation container according to embodiments of the present invention.
Figure 17:
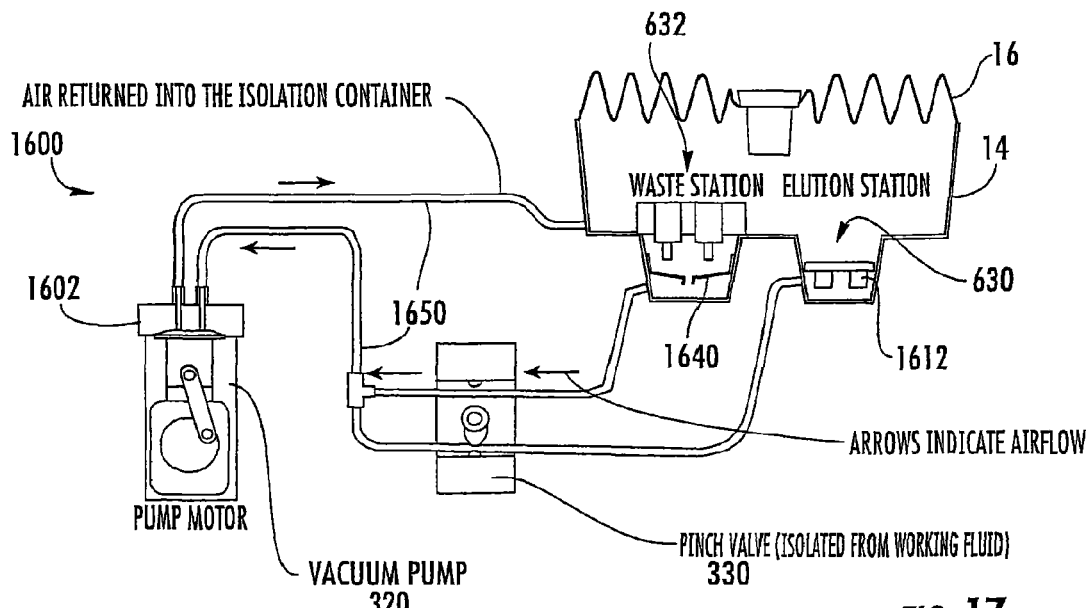

Referring now to FIGS. 16 and 17, the elution station 630 can include an elution tray 1610 configured to capture the final output of the binding columns (e.g., fluid containing DNA, RNA, etc.). To inhibit and/or prevent possible cross contamination between DNA and RNA, each binding column 1410 can have its own receptacle 1612 below it in the elution tray 1610. In some embodiments, the elution process employs a high vacuum, which may generate a significant airflow through the binding column(s) 1410. The elution receptacles 1612 may be shaped to allow splashed fluids, if any, to run off and pool in a collection vessel while deflecting the air stream away from the pooled fluid. Additional features may reduce or minimize the airflow that passes from one receptacle over another. Further discussion of the tray 1610 will be provided with respect to FIGS. 29A-29C.

Figure 30A:
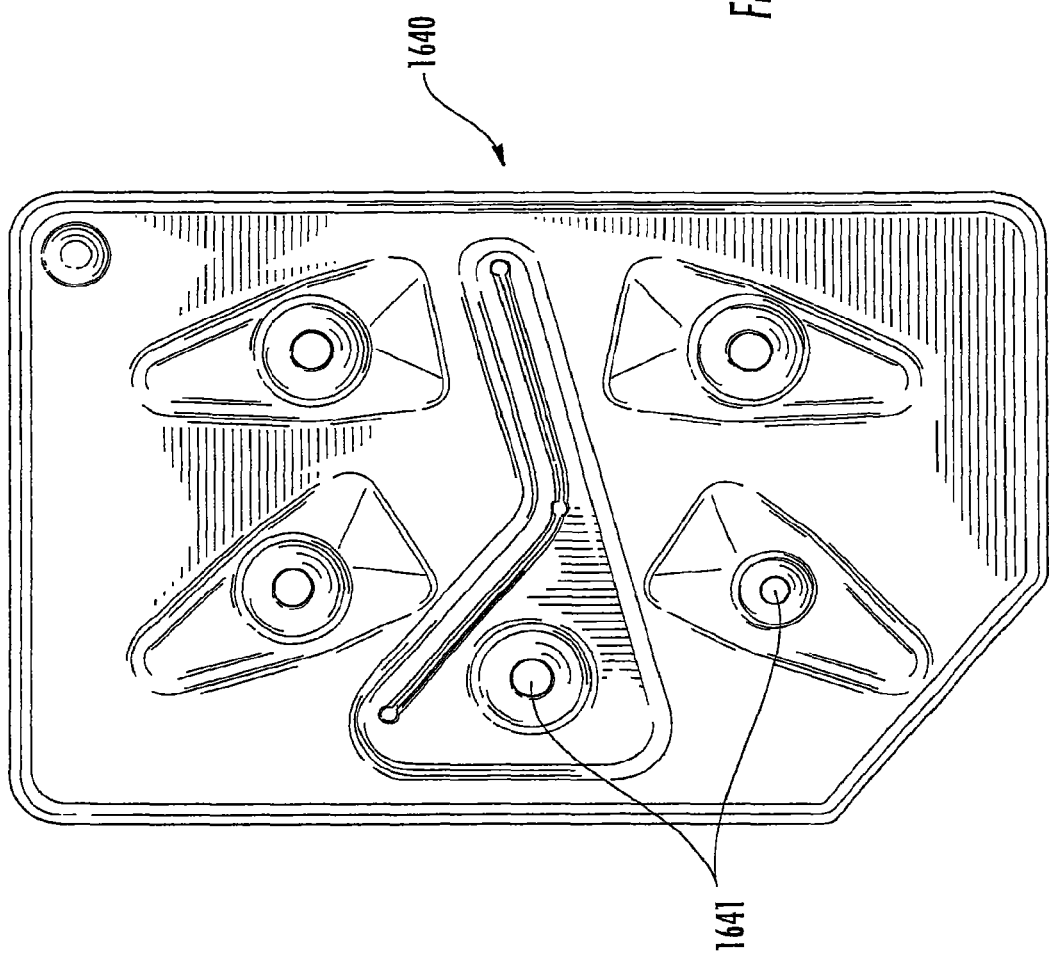
FIG. 30A is a top perspective view of a waste tray cover.
Figure 30B:
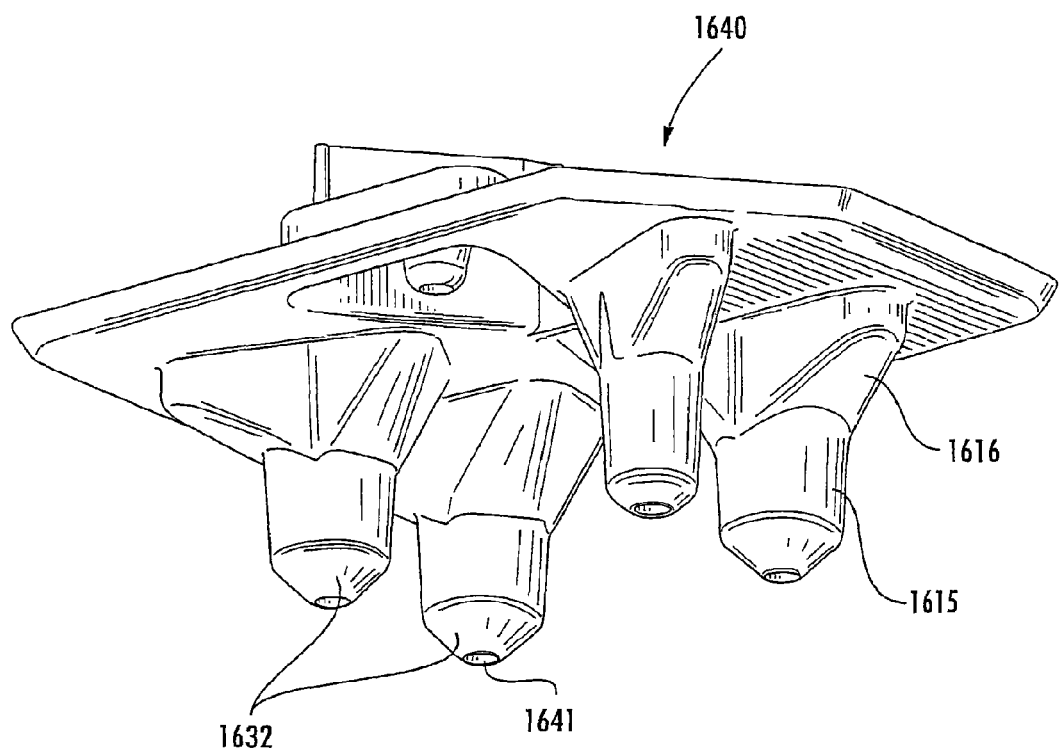
FIG. 30B is a bottom perspective view of the tray cover shown in FIG. 30A.

Waste station 632 may include a waste tray 1630 and waste tray cover 1640. A waste tray cover 1640 may be incorporated into waste tray 1630 to minimize the evaporation of the waste fluid contained in the waste station 632. The waste tray cover 1640 may be shaped to direct all waste fluid to flow down into one or more (shown as a central) drain hole 1641 where it is protected from the main airflow below the cover 1640 inside the waste station 632. FIGS. 30A and 30B illustrate another embodiment of the waste tray cover 1640 which employs a plurality of waste drain holes 1641 using a tray cover that is shaped substantially similar to the elution tray 1610. In the shielded environment below the waste tray cover 1640, the air directly above the waste fluid can maintain a high humidity, thus reducing further evaporation. Further discussion of the tray cover 1640 is provided with respect to FIGS. 30A and 30B.

In some embodiments, a vacuum system 1600 circulates air through container 12. In some embodiments, the isolation container vacuum system 1600 is configured to eliminate the need for filters. The vacuum system can comprise tubing 1650, typically flexible tubing, connected from a pump head 1602, such as via a pinch valve 330 (FIG. 17), to the waste 632 and elution 630 stations. The outlet of the pump head returns the aspirated air back into the isolation container 12.

FIG. 17 shows a circulation path according to one embodiment of the vacuum system 1600. In this embodiment, the tubing 1650 and disposable pump head 1602 may be attached to the isolation container tray 14 during manufacture. These can be sterilized and shipped as part of the assembly associated with the isolation container tray 14. Once an isolation container 12 is loaded and sealed, the vacuum system 1600 can remain closed throughout the rest of the processing. During installation of an isolation container into the processing system 10, the vacuum tubing 1650 can be inserted into the pinch valve 330 and the disposable pump head 1602 is connected to the vacuum pump 320. In some embodiments, the pump 320 only operates when vacuum is required. The pinch valves 330 may be used to direct the vacuum to the appropriate station. When processing is completed, the tubing 1650 may be extracted from the valve 330 and the pump head 1602 is disconnected from the pump 320. The tubing 1650 and pump head 1602 can be single-use disposable, along with the rest of the isolation container 12.

FIG. 18 shows a cutaway view of a tray 14 in place on the work surface 200 of a processing system 10, showing exemplary locations of the pinch valve 330 and disposable pump head 1602. Peltier plates 370 and 372 may provide cooling for a segment of the rear wall 14p of the tray 14 and for the waste station catchment in the base of the tray 14, respectively. The wall segment 14p may be substantially planar (typically substantially vertical, but may be angled) and project inward to define a receiving space for the plate 372. The wall 14p may be configured to cooperate with the plate 372 to define a condensation wall. It is noted that in FIG. 18, the thermal cycler lid drive system 310 is shown with the lid extended into container, without the seal 430 in place and the disposable pump head 1602 is shown, without the flexible vacuum pump tubing 1650, in place.

Exemplary Process Control and/or Yield Measurement Systems

Figure 19A:
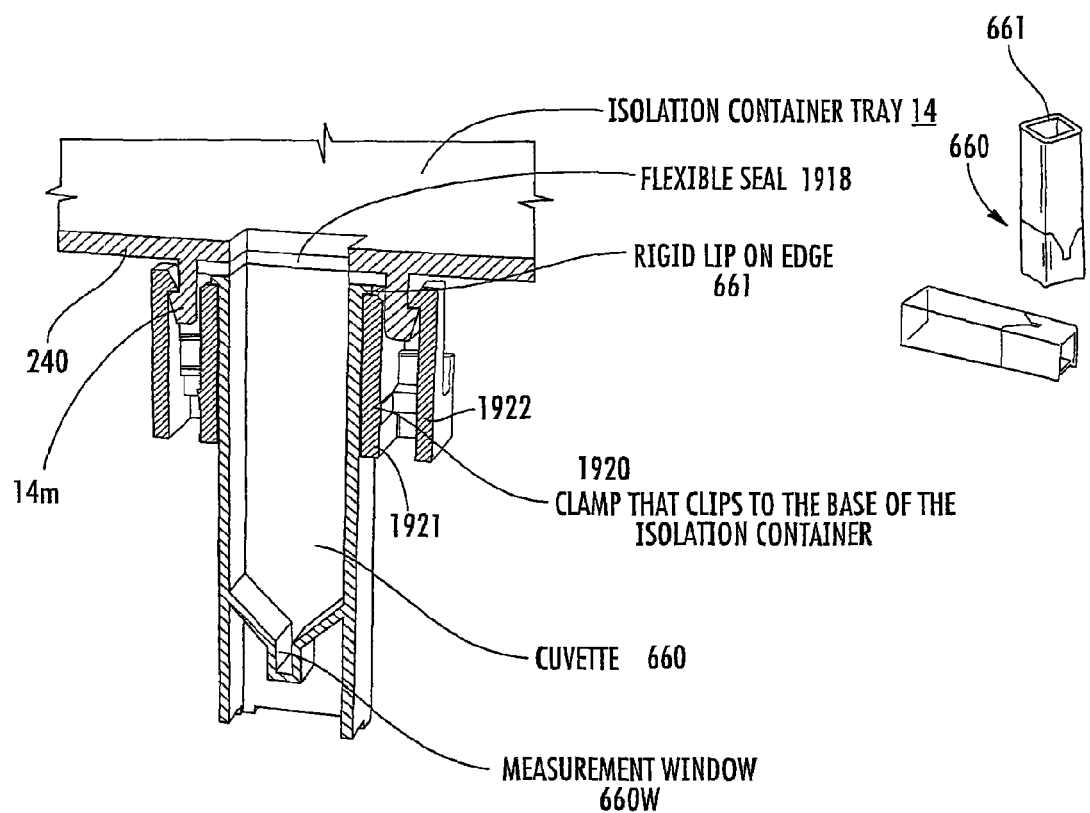
FIG. 19A is a cross-sectional perspective view of a cuvette attached to an isolation tray according to embodiments of the present invention.
Figure 20A:
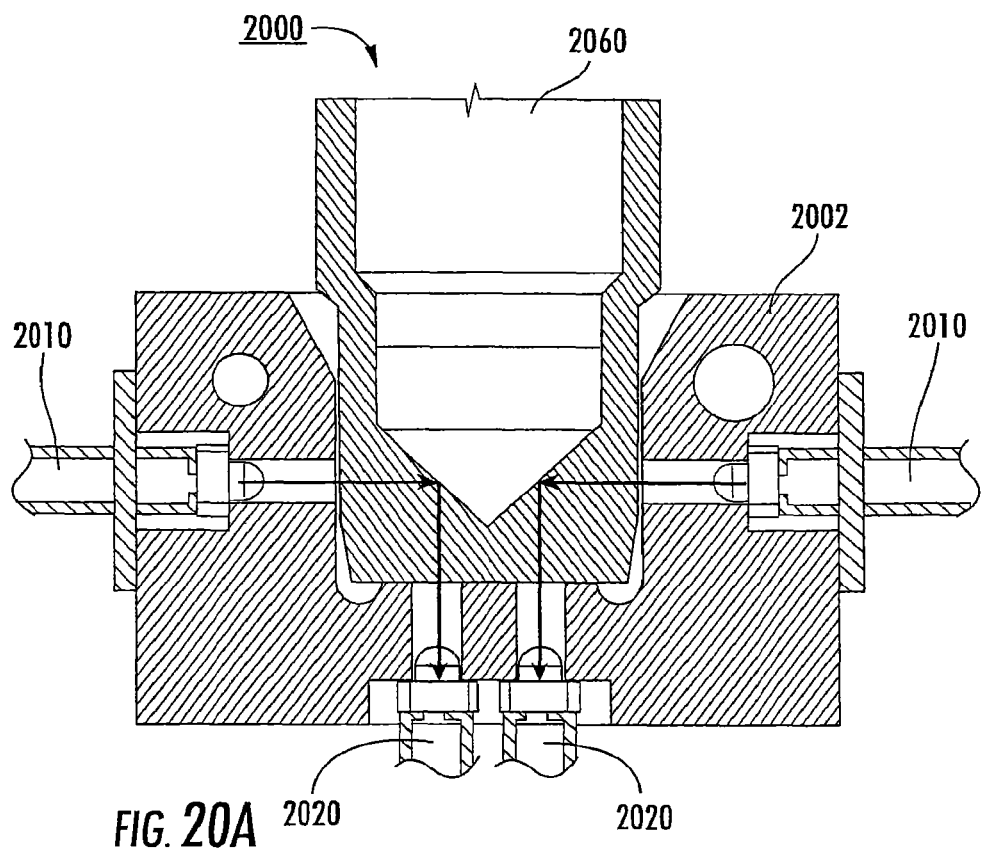
FIGS. 20A-20D are examples of operations of a system to measure volume in a volumetric cuvette according to embodiments of the present invention, each figure being a section view of the volumetric cuvette measuring system.
Figure 20B:
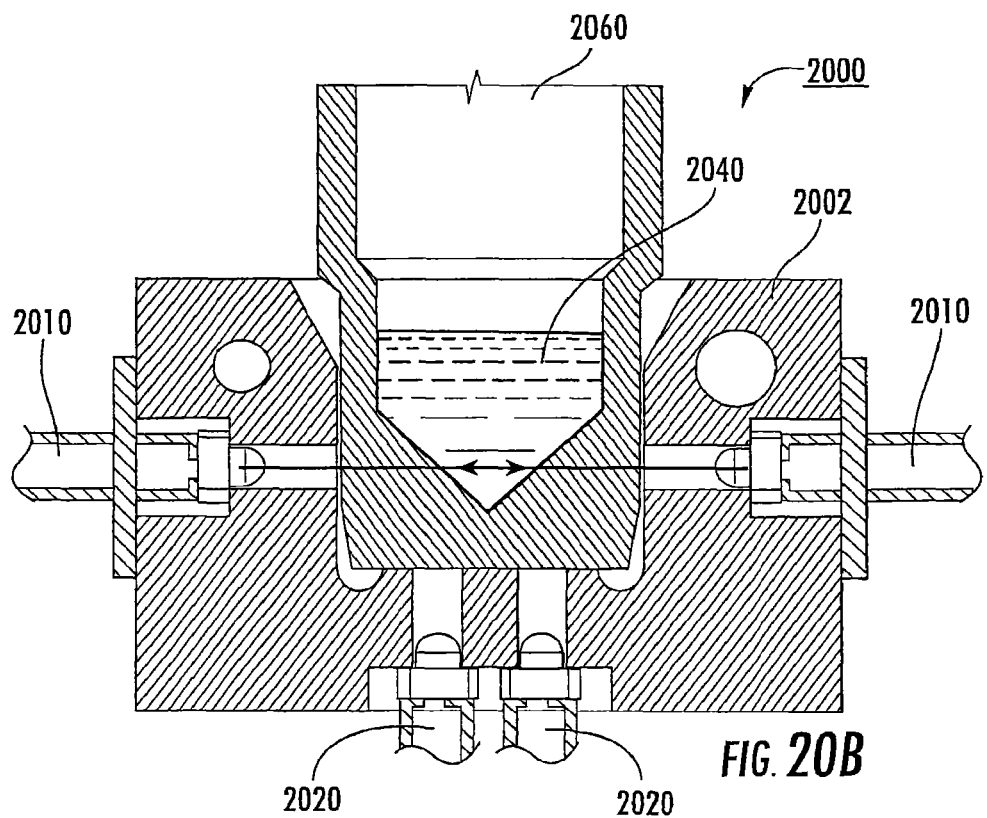
Figure 20C:
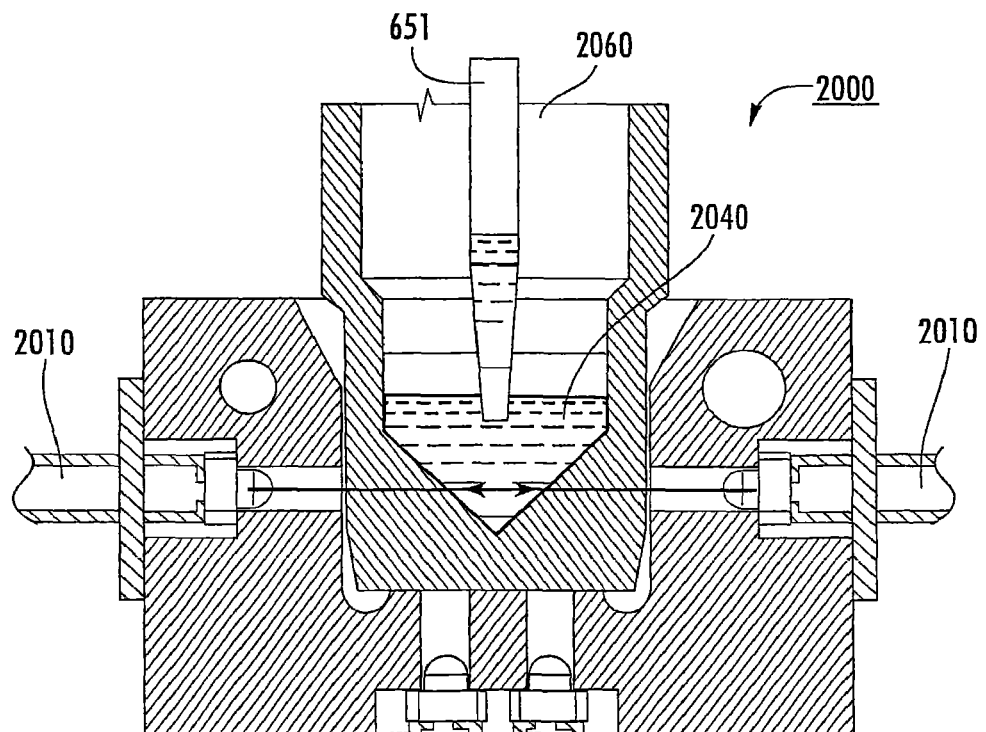
Figure 20D:
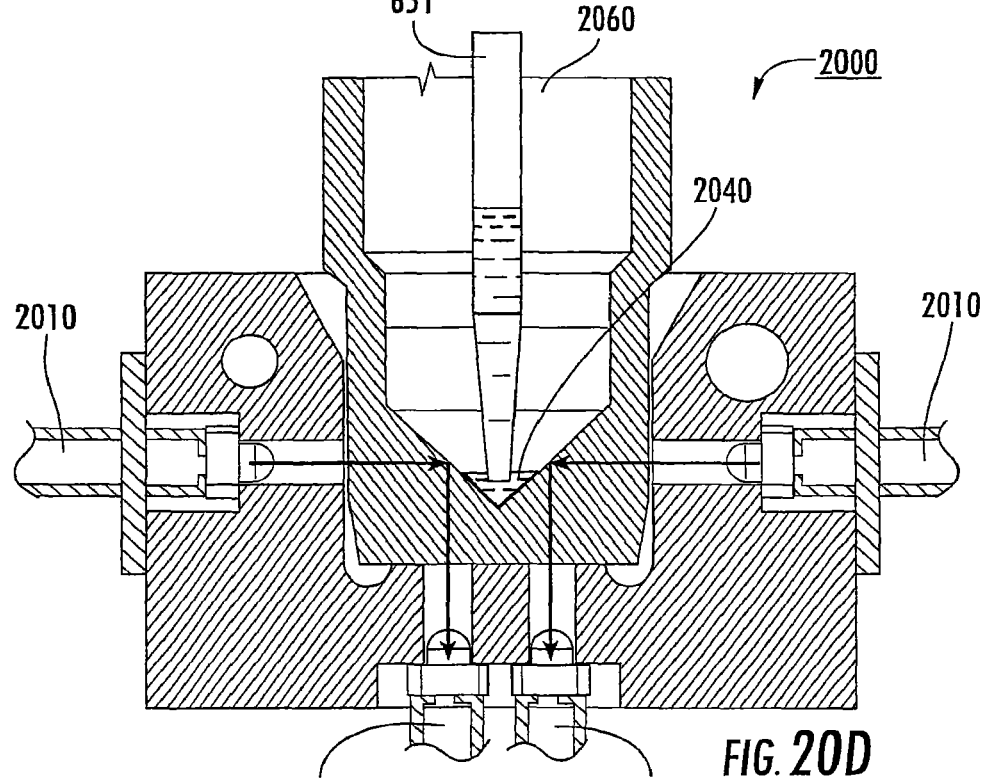
Figure 20F:
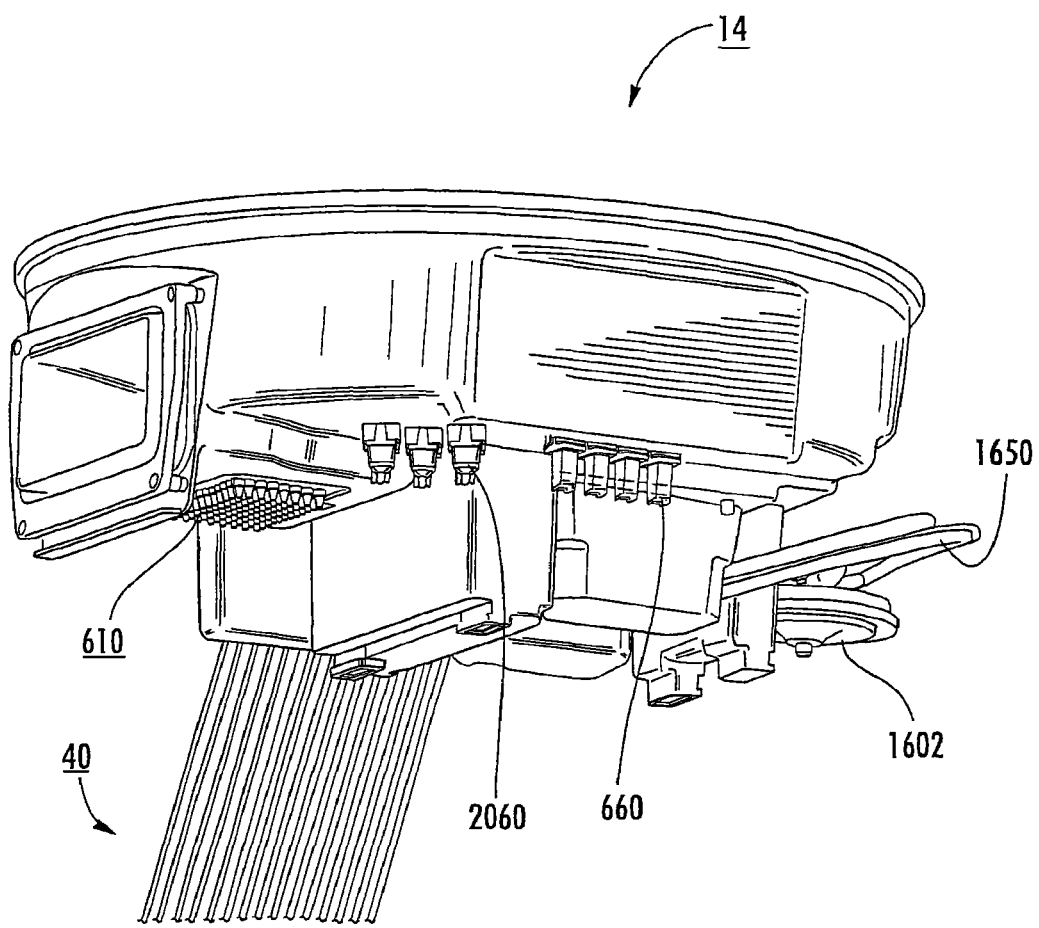
FIG. 20F is a bottom perspective view of the container shown in FIGS. 4 and 5 illustrating cuvettes extending below the bounds of the container according to embodiments of the present invention.

In some embodiments, disposable cuvettes 660, 2060 can be used, for example, as shown in FIG. 19A and FIG. 20F. One or more cuvettes 660, 2060 may be fixedly or releasably mounted to isolation container tray 14, e.g., such that cuvettes 660, 2060 extend vertically down from the bottom of tray 14.

In some embodiments, the concentration and/or purity of samples, e.g. nucleic acids or proteins, can be measured using a spectrophotometer 1900s (FIGS. 3, 19B) and cuvettes 660 (FIGS. 19A, 20F) or alternative optical methods for concentration measurements, e.g., fluorometer, can be similarly incorporated in the system.

In some embodiments, as shown in FIG. 19A, one or more disposable concentration cuvettes 660 are sealably mounted to the tray 14 via a flexible sealing member 1918, such as a gasket or O-ring. The tray 14 includes mounting members 14m that engage a clamp 1920 to hold the cuvette 660 tightly against the sealing member 1918, thus sealing the cuvette 660 to the tray 14 and maintaining the sealed processing environment inside the isolation container. As shown, the cuvette 660 can include an outer edge that is formed as a rigid upper lip 661. The clamp 1920 includes an inner upstanding arm 1921 that resides against the lip 1901 and an outer arm 1922 that engages the mounting member 14m to force the cuvette 660 against the tray 14. The cuvette 660 includes a cuvette measurement window 660w, typically at a lower portion thereof.

Alternatively, the cuvettes 660 (or cuvettes 2060) can be molded into the tray, overmolded, mechanically clamped, solvent bonded, adhesively affixed, or the like. The spectrophotometer 1900s (FIG. 3) can be mounted on the processing system 10, e.g., beneath the isolation container 12. The spectrophotometer 1900s can be configured to make absorbance measurements through cuvettes 660 (FIG. 20F) while remaining outside the isolation container.

In some embodiments, there is a cuvette 660, 2060 for each measurement, such that no cuvette need be reused. The processing system 10 can be configured to move a spectrophotometer cuvette holder 360 (see, e.g., FIG. 3, 19B) from cuvette 660 to 660 for each measurement as required. In some embodiments, cuvettes 660 and/or 2060 may be removed from the tray 14, washed and reused in subsequent trays 14. In other embodiments, removable cuvettes 660, 2060 are single-use only (i.e., single-use disposable).

Various types of spectrophotometers are known and may be utilized for nucleic acid concentration and purity measurements. The spectrophotometer 1900s may be able to communicate with and be controlled by a controller associated with the processing system 10. For example, the processing system 10 can command the spectrophotometer 1900s to take a measurement and the spectrophotometer 1900s can be able to return the absorbance measurements, typically at ultraviolet wavelengths, such as for example, at about 260 and/or 280 nm, or at any other wavelength of interest. Additionally, the geometry of the spectrophotometer 1900s and particularly that of a cuvette holder 360 can be integrated with other components of the overall system.

Figure 19B:
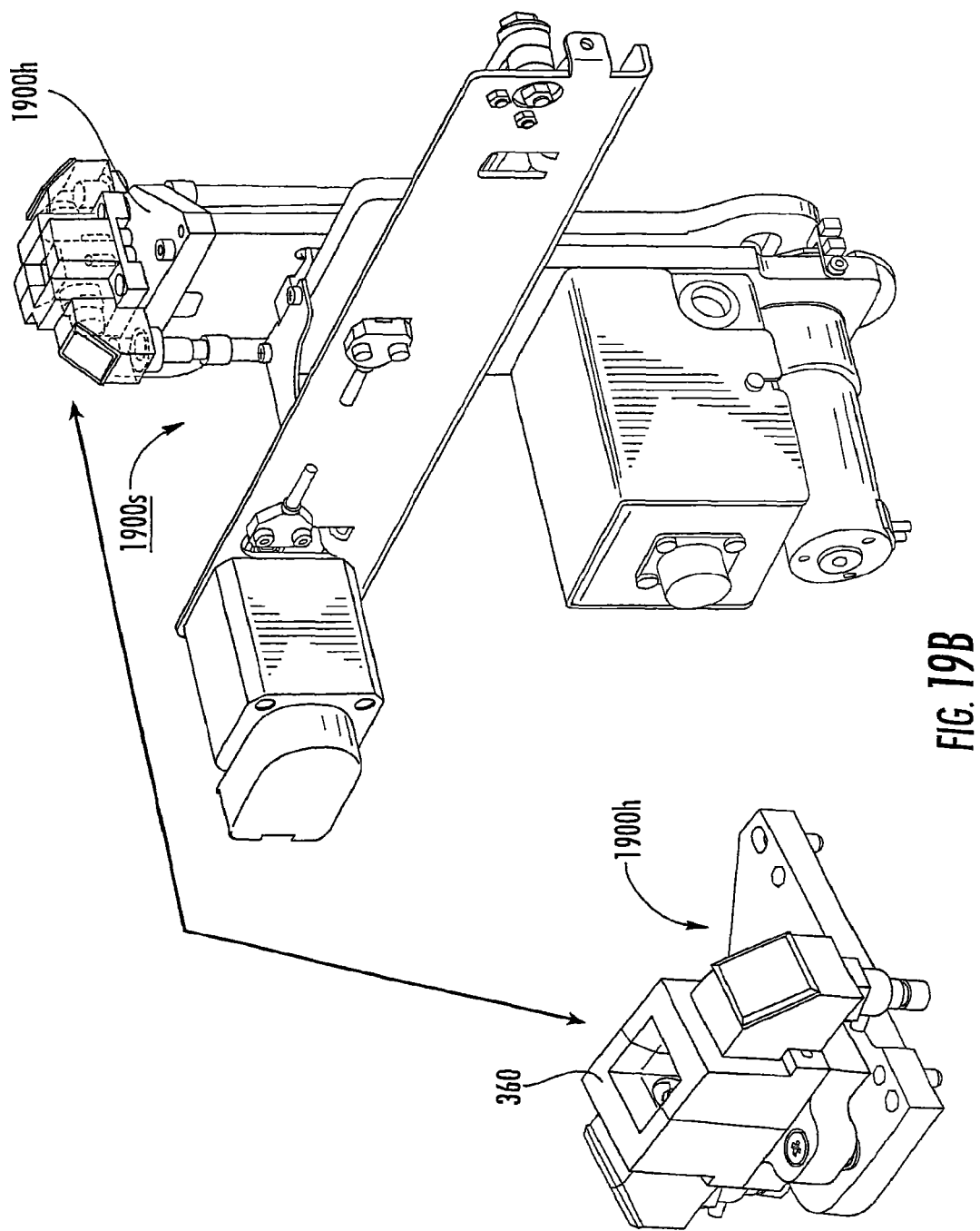
FIG. 19B is a side perspective view of cooperating components of a spectrophotometer cuvette measuring system according to embodiments of the present invention.

FIG. 19B illustrates a spectrophotometer head mechanism that is used to move a single detector head between a number of cuvettes 660, shown as (4) cuvettes 660 in FIG. 20F. A robotic operational platform may be used to position the spectrophotometer cuvette holder 360, e.g., to raise, lower and traverse between cuvettes 660. The spectrophotometer 1900s and light source may be mounted in an electrical cabinet of the system, e.g., on a left or right side of the system. Optical fibers may be used to allow the cuvette holder 360 to move while the spectrophotometer 1900s and light source remain stationary. That is, as shown in FIG. 19B, a spectrophotometer drive mechanism can be used to move a single detector head 1900h to serially hold each of the different cuvettes 660. The detector in the detector head 1900h can be coupled to the spectrophotometer 1900s via a plurality (typically two) optical fibers. In other embodiments, each cuvette 660 could be located in an individual cuvette holder 360 and the light source switched between the optical fibers connecting the light source to the multiple cuvette holders (not shown) to communicate with the spectrometer for measurements.

Volume measurement(s) of a sample may be used in combination with the concentration measurement(s) to determine yields. In some embodiments, a volume measurement unit 2000 utilizes the pipetting system and a fluid sensor in a dedicated vessel, e.g., as shown in FIGS. 20A-20E. For example:

FIG. 20A shows an empty cuvette 2060 in a detector head 2002, wherein light from two IR emitters 2010 does not pass through the cuvette 2060, and is received by two IR receivers 2020 for reflected light.

When a fluid 2040 to be measured is pooled in the volumetric cuvette 2060, e.g., as shown in FIG. 20B, light from the two IR emitters 2010 is transmitted through the cuvette 2060 and the fluid 2040 and is not received by the two IR receivers 2020 for reflected light.

While a control system monitors the presence of the fluid detected by the system 2000 at the bottom of the measurement vessel 2060, the pipette head 220 is used to aspirate the sample 2040 into a pipette tip 651 as shown in FIG. 20C.

As shown in FIG. 20D, when the sensor system 2000 reports fluid absent, the syringe pump 350 (FIG. 3) can be stopped and the volume aspirated can be electronically determined and recorded. Thus, the cuvette 2060 has a prism design in the bottom. Using a light source with detectors the instrument can determine the presence or absence of liquid in the cuvette 2060 based on the reflection. This, in combination with the pipetting device determines the volume by measuring the liquid it is removing until receiving the signal that no liquid is present. FIG. 20E illustrates that the system 2000 can employ a plurality of spaced apart detector blocks 2002, each having its own pair of transmitters 2010. Each block 2002 can be configured to hold and cooperate with a respective cuvette 2060 for obtaining a volume measurement using the volume measurement system 2000.

As shown in FIG. 20F, the tray 14 can include a plurality of both the volume cuvettes 2060 (e.g., volume measurement cuvette) and a plurality of spectrophotometer cuvettes 660 (the cuvettes 660 can be used for concentration measurements). The spectrophotometer cuvette 660 can be a standard UV visible plastic disposable such as BioRad "trUView cuvettes". The device 10 can include spectrophotometer components for measurements. Suitable spectrophotometer components can be obtained from Ocean Optics, having a place of business at Dunedin, Fla.

Exemplary Process Constituent Storage Systems

In some embodiments, reagent vessels are used to contain the reagents, the sample and mixing volumes of fluid combinations within the isolation container 12. Reagent vessels with various different capacities may be used to accommodate the range of fluid volumes used during the process.

To reduce the risk of reagent contamination, evaporation or spillage, each vessel that contains reagent can be sealed, typically over a top surface, such as with polypropylene-lined foil, prior to loading into the tray 14. The seal can be configured to be pierced by a pipette tip 651. The seal allows reagents to be loaded and sealed into the appropriate reagent vessel and stored without the risk of contamination, spillage or evaporation.

Figure 21A:
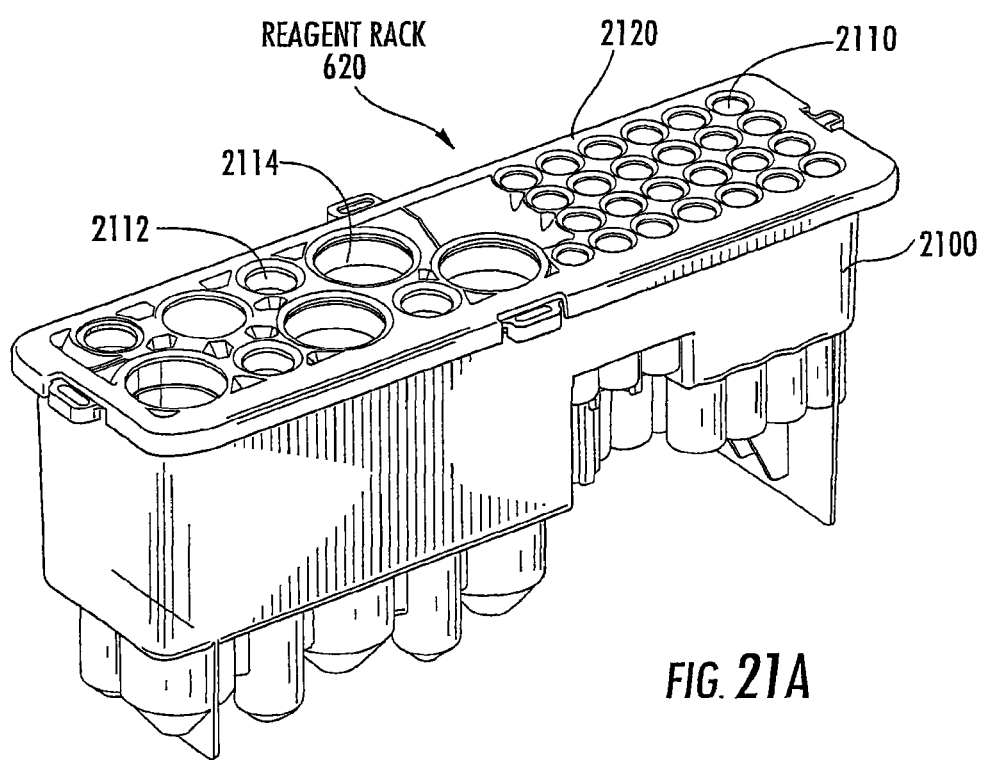
FIG. 21A is a perspective view of a reagent rack according to embodiments of the present invention.

An example of a reagent rack 620 is shown in FIG. 21A. Rack 620 may have any desired layout, can accommodate any reagent vessel size, and can be adapted for any process. In the example shown, the reagent tray or rack 620 includes a base 2100 for housing a number of vessels 2110, 2112, 2114, typically tubes, of different sizes that may contain for example sample and reagents, as well as mixing vessels. Each of the vessels can be supported within the base 2100, and a cover 2120 may be clipped or otherwise attached onto the rack 620 to ensure the vessels are kept securely in place. The cover 2120 includes apertures to allow the pipette tip to access the vessels held thereunder.

In some embodiments, reagents, samples, or other fluids can be loaded into the rack 620 as a sub-assembly, and the rack 620 is then loaded into the tray 14. In some embodiments, the design of the reagent rack 620 is such that it can only be placed into the isolation container tray in one orientation. Alternatively, the reagent rack 620 may be molded or otherwise made an integral part of the isolation container tray 14. Reagents may be loaded directly into an integral reagent tray or tubes or other vessels containing a reagent may be placed in the reagent tray. The placement of the vessels 2110, 2112, 2114 at a defined rack location (address) allows the robotic interface to automatically engage the correct vessel (reagent) at the correct time in the process.

In some embodiments, the tray layout allows access to all the vessels without the pipette tip having to pass over other dissimilar reagents, and thus reduces the chance of reagent cross contamination. Of course, other configurations may be used, for example, depending upon the desired processes to be performed.

Figure 21B:
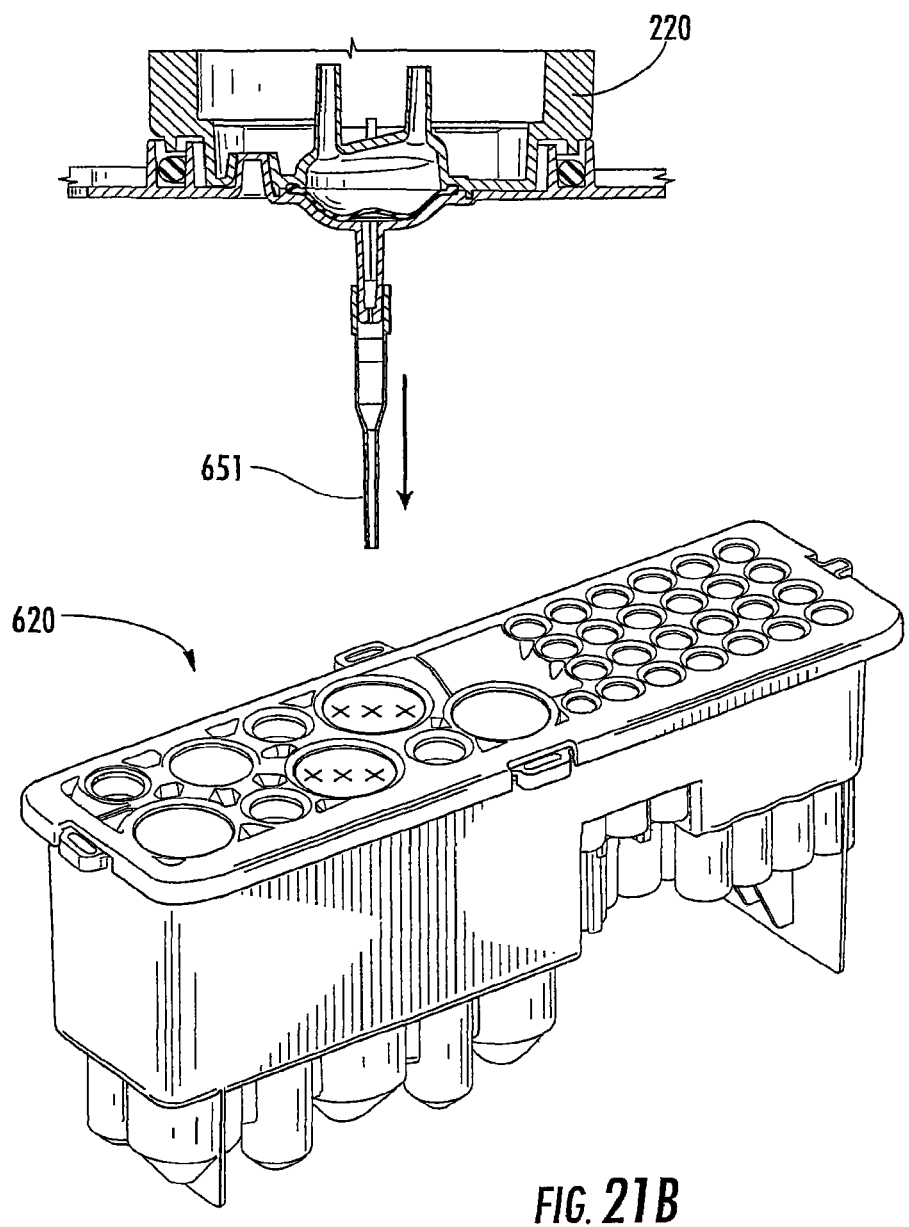
FIG. 21B is a schematic top perspective view of the reagent rack shown in FIG. 21A illustrating a piercing technique according to embodiments of the present invention.

FIG. 21B illustrates that a multi-point (shown as a three-point) piercing sequence can be used to open the seal on a vessel 2110, 2112, 2114, respectively, before withdrawing the (reagent) liquid. That is, the pipette 651 can be directed to pierce a seal covering at two outer locations before moving to the actual withdraw piercing (typically at a center location) to facilitate pipetting accuracy.

Exemplary Aliquot Removal Systems

During automated processing in system 10, one or more aliquots of a sample and/or products may be used for process evaluation, control, quality testing and/or storage for further processing (e.g., see aliquots tubes 440 in FIGS. 4 and 5).

In some embodiments, the isolation container 12 and processing system 10 allow aliquot removal during processing without compromising the sealed nature of the isolation container 12. A plurality of flexible tubes can be in fluid communication with an interior sample capture region of the container 12 and extend from the system 10 to be externally accessible by an operator. Each flexible tube is presealed or has a closed end portion. Each aliquot may be aspirated into an individually labeled container 440, for example a tube, while the container 12 remains closed. An operator or an automated sealer may seal the aliquot into the tube 440, e.g., upstream of the captured aliquot of fluid, such as by using an RF tube sealer, or other seal closure mechanism. Once sealed, an aliquot tube can be detached from the isolation container and taken away for storage, testing, or further processing.

In some embodiments, an aliquot assembly 40 is used for aspirating the aliquot fluid into the tube 440 and utilizes a clamping member and the elasticity of aliquot tubing 440 to draw the fluid from inside the container 12 into the tube. This mechanism can be automated to facilitate the tubing being clamped for a short time, thus reducing the likelihood of any change in the elasticity of the tubing caused by clamping deformation.

Figure 22:
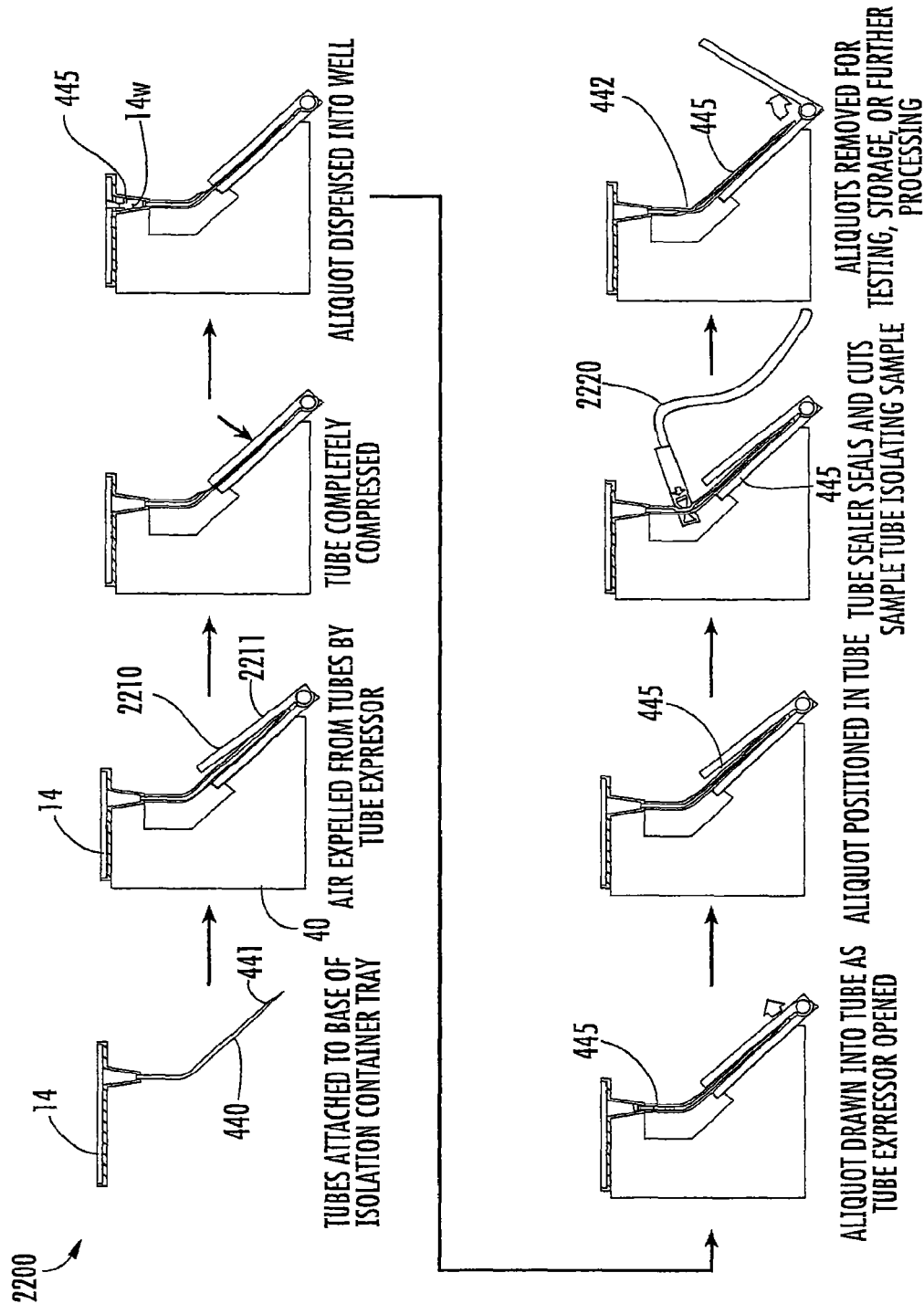
FIG. 22 is a series of schematic illustrations showing operation of an aliquot tube mechanism according to embodiments of the present invention.

FIG. 22 illustrates an exemplary method 2200 of using an aliquot assembly 40, and shows a series of steps (from left to right and top to bottom) that can be used to load the aliquot tubes 440 with an aliquot fluid 445. As shown, an aliquot tube 440 with a closed end 441 is sealably attached to the tray 14 under a well 14w. In this example, a clamping member (tube expressor) 2210 is pressed against one or more aliquot tubes 440 to expel air from the tubes (as shown by the second and third figures). After or while air is discharged in response to the tube being completely compressed by clamp 2210 (with upper clamping member 2211 forced down against the tube and other clamp surface), the aliquot substance 445 is placed or dispensed in the well 14w in communication with the tube 440. Upon subsequent release of the clamping force, an aliquot of fluid 445 is drawn into the tube 440 by a negative pressure within the elastic tube. A tube sealer 2220 (such as an RF welder) may be used to seal (at 442) and optionally cut the aliquot tube upstream of the seal to isolate the sample 445 within the tube. Other sealant mechanisms may also be used.

Exemplary Methods of Assembling a Container

Figure 23A:
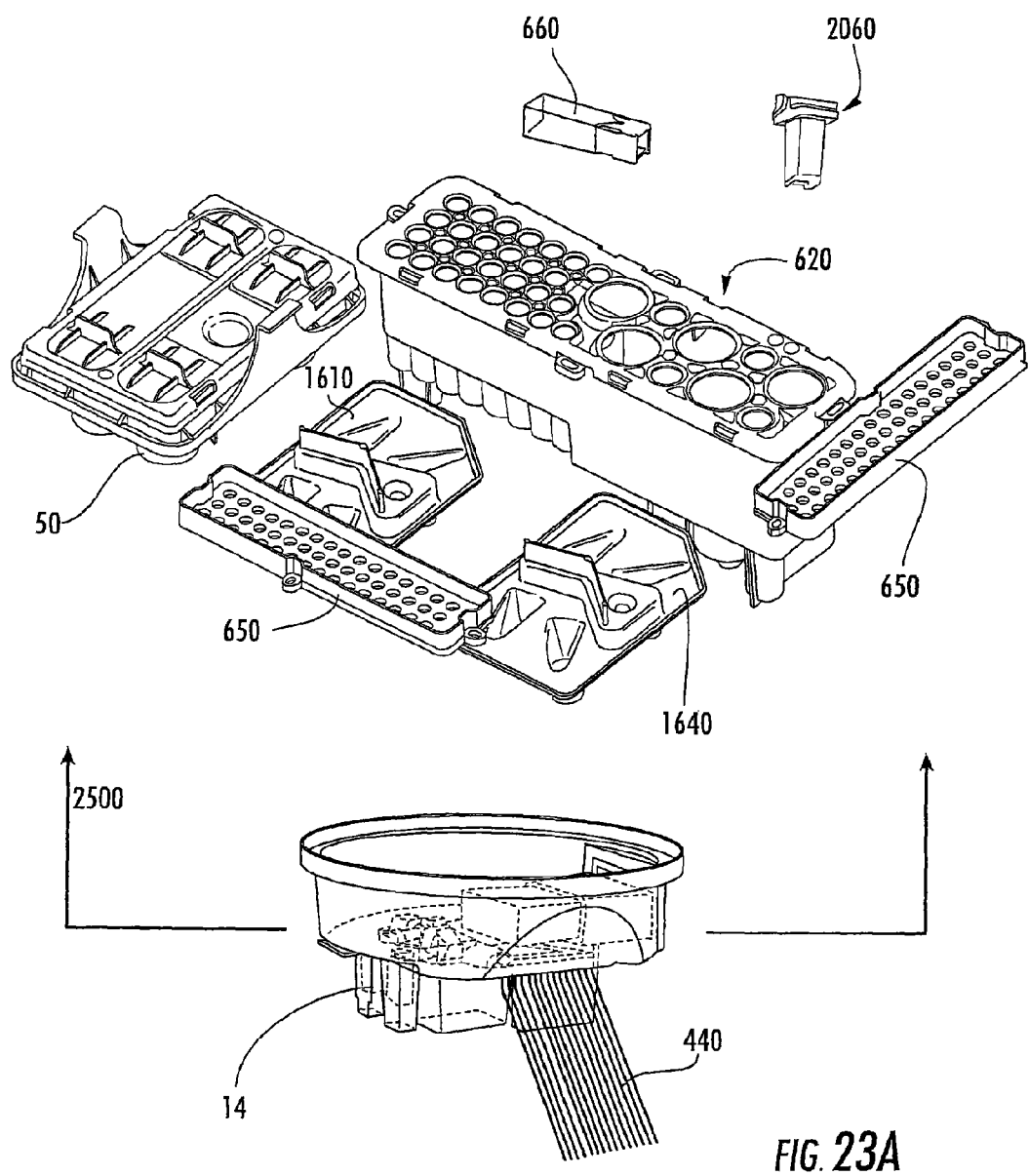
FIG. 23A is an illustration showing components that may be loaded into an isolation container tray according to embodiments of the present invention.
Figure 23B:
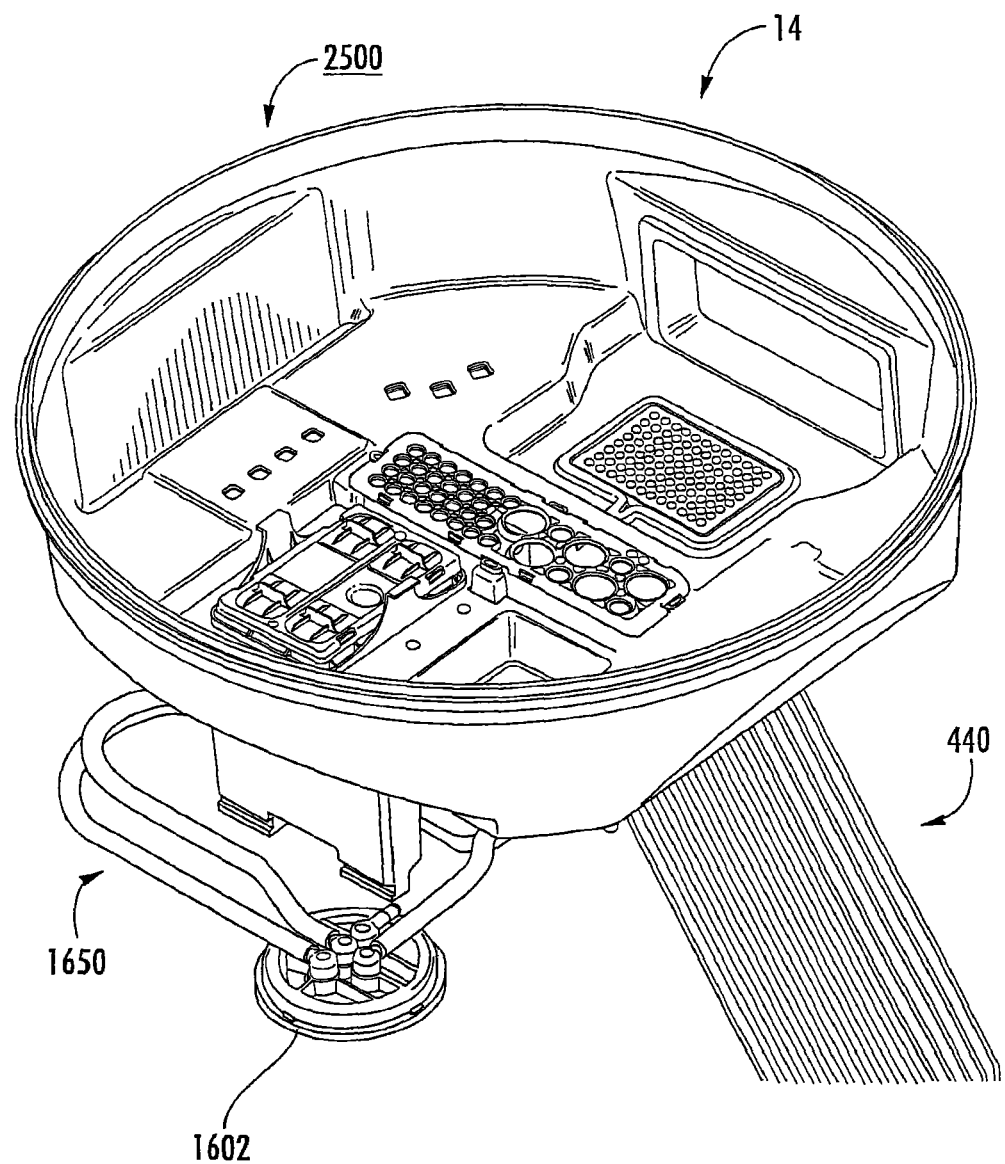
FIG. 23B is a top perspective view of a partially assembled container using the kit components shown in FIG. 23A according to embodiments of the present invention.

FIG. 23A is an exploded representation of a kit 2500 that can be provided to allow an operator to prepare a closed system for processing. The kit 2500 can include the tray 14, the binding manifold 50, the pipette tip rack 650 (and pipette tips 651), and cuvettes 2060, 660. The tray 14 can be packaged and shipped to a use site with the aliquot tubes 440 attached and/or the vacuum head and associated tubing attached. The components can be sterilized and packaged (or packaged, then sterilized) in a sterile package for shipment and handling. The components may be surface sterilized at a point of use and the assembly of the components may be in a Class 10,000, 1000, or even 100 clean room. The components may also be provided separately or preloaded in other combinations.

Figure 23D:
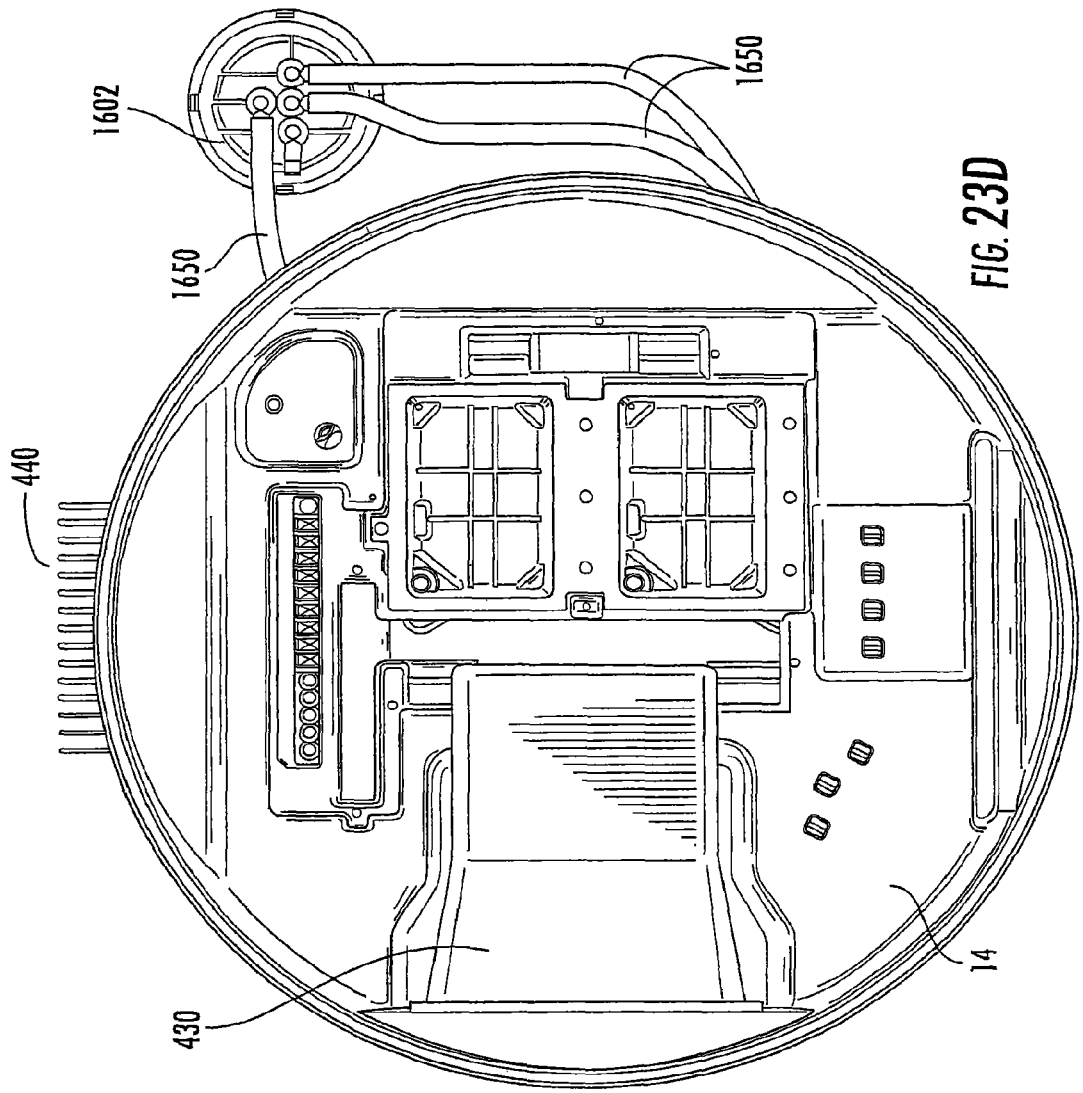
FIG. 23D is a top view of the container in the kit shown in FIG. 23A before kit components are attached at a use site according to embodiments of the invention.

FIG. 23B is a partially assembled view of the kit shown in FIG. 23A. FIG. 23C is a bottom view of the partially assembled kit shown in FIG. 23B. FIG. 23D is a top view of the container 14 shown in FIG. 23A prior to assembly of the discrete components shipped with or separate from the container or tray 14.

Figure 24:
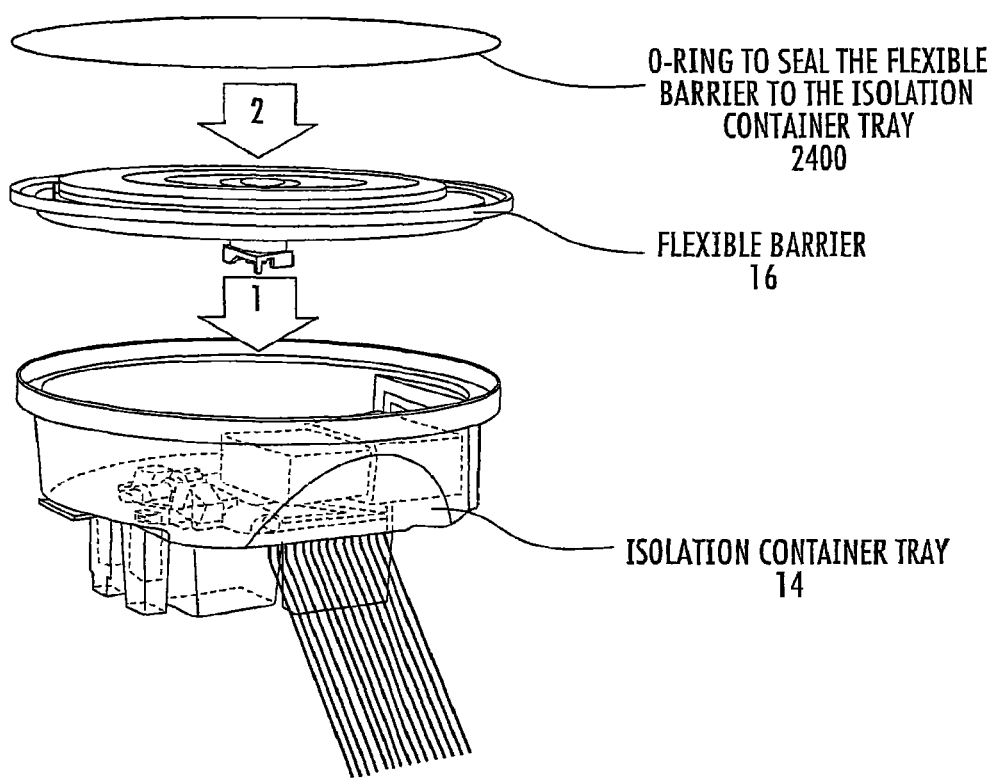
FIG. 24 is an exploded view of the isolation container tray of FIG. 23A illustrating sealing of the tray with a flexible barrier according to embodiments of the present invention.

FIG. 24 illustrates an exemplary method of sealing, respectively, an isolation container 12 according to embodiments of the invention (for example, for aseptic processing nucleic acids from one or more biological samples). For such aseptic processing, the barrier 16 and tray 14 sections of the isolation container assembly 12 may be individually pre-packaged and sterilized. When the isolation container 12 is needed for processing, the tray 14 and barrier 16 may be transferred to a biological safety cabinet or equivalent clean, controlled area for loading.

As shown in FIG. 23A, the tray 14 of an isolation container 12 may be loaded with one or more reagent trays 620 comprising samples and reagents to be used in the desired process. The assembly and/or loading of the tray 14 can take place with the tray 14 on the trolley 399 (FIG. 27) as discussed above. One or more pipette tip racks 650 and binding column manifolds 50 may also be loaded into the working area 18 of the tray 14. In some embodiments, one or more cuvettes 660, 2060 are attached to the base of tray, for example, as shown in FIG. 20F. Depending upon the desired assay or process to be performed, other samples, analytes, reagents, vessels, other consumables, devices, tools and/or other items may be loaded into tray 14.

In some embodiments, after all of the desired items are placed within or attached to the tray 14, the barrier 16 can be attached to the tray 14 to seal the assembled isolation container 12, for example as shown in FIG. 24. In some embodiments, an O-ring 2400 may be used to seal the flexible barrier 16 to the tray 14. The O-ring can be forced snugly over the barrier 16 and into the perimeter slot on the tray 14. In other embodiments, one or more gaskets, clips, clamps, fasteners, adhesives, and/or other attachment means may be used.

As shown in FIG. 27, the tray 14 can be locked to a holding surface on a trolley during transport. After the tray 14 is loaded and sealed with the barrier 16, the isolation container 12 may then be transferred to the work surface 200 of the processing system 10. Alternatively, the isolation container can be assembled and sterilized. Then, reagents and samples can be introduced into a sealed isolation container using standard aseptic transfer methods or by other closed means. The trolley can also be used to hold the tray 14 during assembly. Alternatively, a separate barrier isolator trolley-assembly cart may be used when assembling the isolation container 12 (not shown). Such a barrier isolator trolley may be integrated into the barrier isolator itself and can mate with the transport trolley as discussed above.

The isolation container assembly 12 may be installed into the system 10 and connected to each piece of equipment used for processing the samples. To ensure correct alignment, the rigid tray 14 may be clamped onto the work surface 200. The flexible barrier 16 and pipette head 220 may connect to the robotic pipette head adapter 210 (see e.g., FIG. 2). As shown for example, in FIG. 12, thermal cycler evaporative seal 430 may connect to the thermal cycler lid 1010, e.g., using vacuum cups 1140 or other fasteners or attachment means, and vacuum tubing and the disposable pump head for the waste and elution stations are fitted to the corresponding valves and pump. To remove an isolation container, the reverse procedure may be used.

Figure 25:
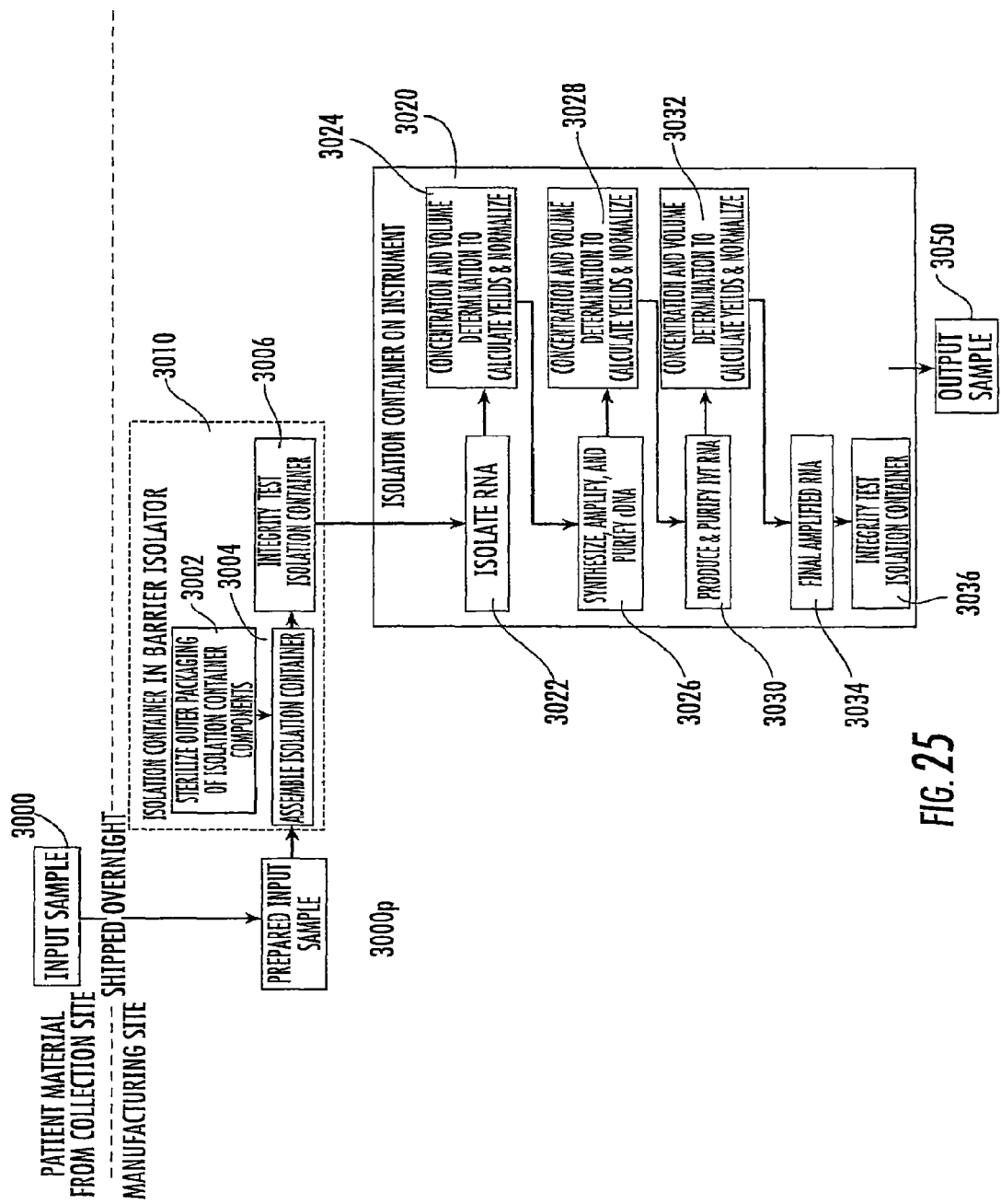
FIG. 25 is a flow chart of operations that can be carried out according to embodiments of the present invention.

FIG. 25 is a flow chart of operations that can be carried out at a manufacturing site according to embodiments of the invention. As shown, an input sample 3000 is provided (typically from a patient collection site or a subject's specimen storage site). When time-sensitive, the specimen can be shipped for receipt at the manufacturing site within 12-48 hours (such as overnight). At the manufacturing site, the isolation container 12 is prepared in a barrier isolator (block 3010) and sample may also be prepared (block 3000p) prior to placement in the container (e.g., homogenized, mixed and/or centrifuged). The outer packaging of the isolation container components, e.g., the tray 14, the barrier 16 and the container contents can be sterilized (block 3002). The assembled and sealed isolation container can be assembled (block 3004) and integrity-tested (block 3006) to confirm a sealed state.

The closed assembled isolation container can be moved to the instrument for processing (block 3020). As shown, the RNA from the patient sample can be isolated (block 3022) using silica membrane columns and appropriate RNA binding and elution reagents. Concentration and volume determinations are performed out to calculate yields and the concentration is normalized (block 3024). The cDNA is synthesized by a reverse transcription (RT) reaction, amplified through PCR, and purified (block 3026) using silica membrane columns and appropriate cDNA binding and elution reagents. Concentration and volume determinations are performed to calculate yield and the concentration is normalized (block 3028). IVT RNA is produced from the resulting cDNA, treated with DNase and purified (block 3030) using silica membrane columns and appropriate RNA binding and elution reagents. Concentration and volume determinations are performed to calculate yield and the concentration is normalized (block 3032) resulting in the final amplified RNA (block 3034). The RNA disposable can be integrity-checked (block 3036) to confirm that the system is still sealed and isolated from the environment to thereby ensure that there was no contamination during the process. Intermediate and/or final products can be output as one or more aliquot amounts (block 3050).

Figure 29A:
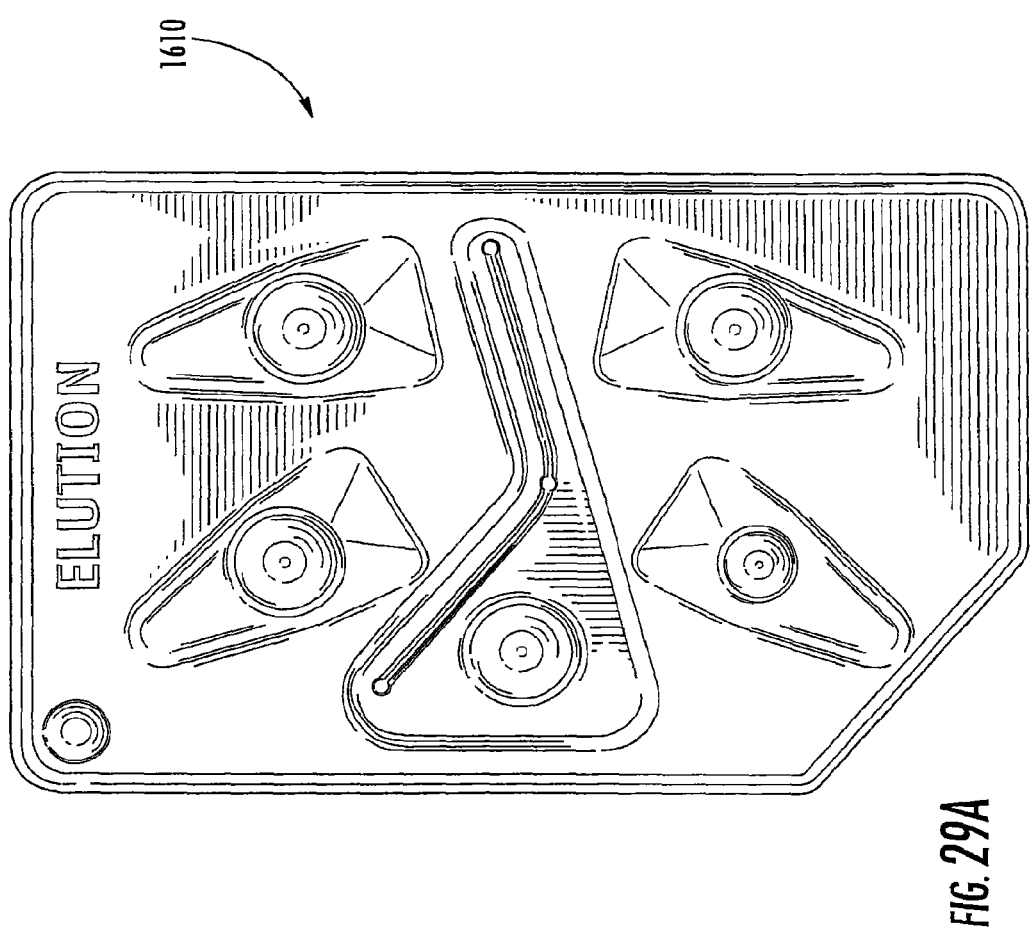
FIG. 29A is a top view of an elution tray according to embodiments of the present invention.
Figure 29B:
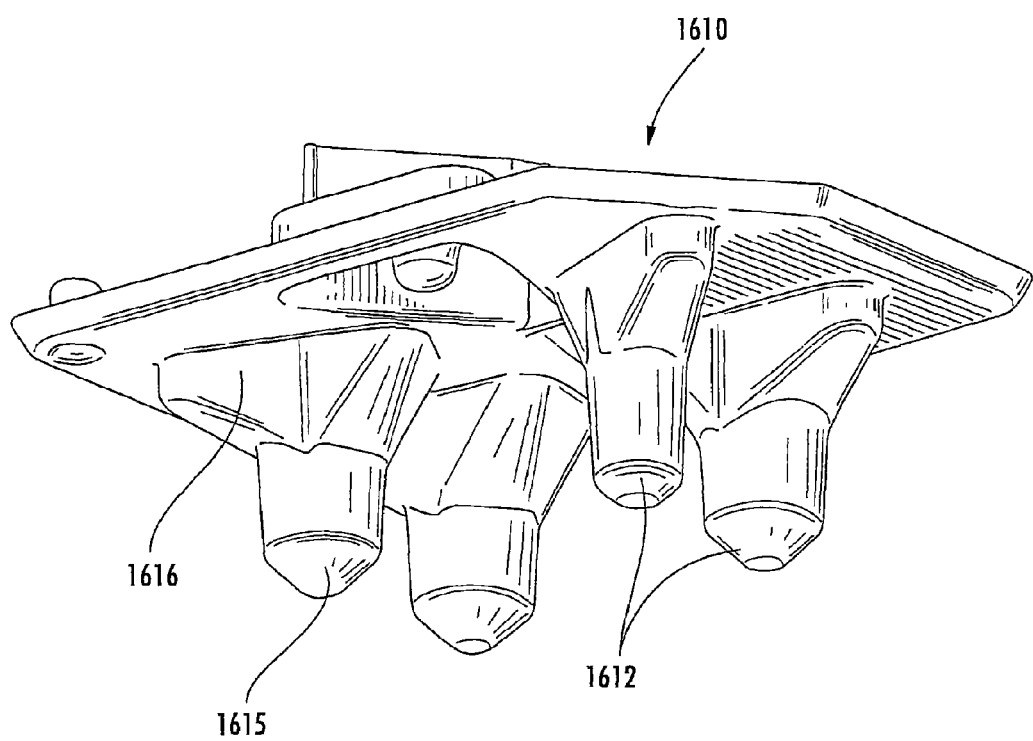
FIG. 29B is a bottom perspective view of the tray shown in FIG. 29A.
Figure 29C:
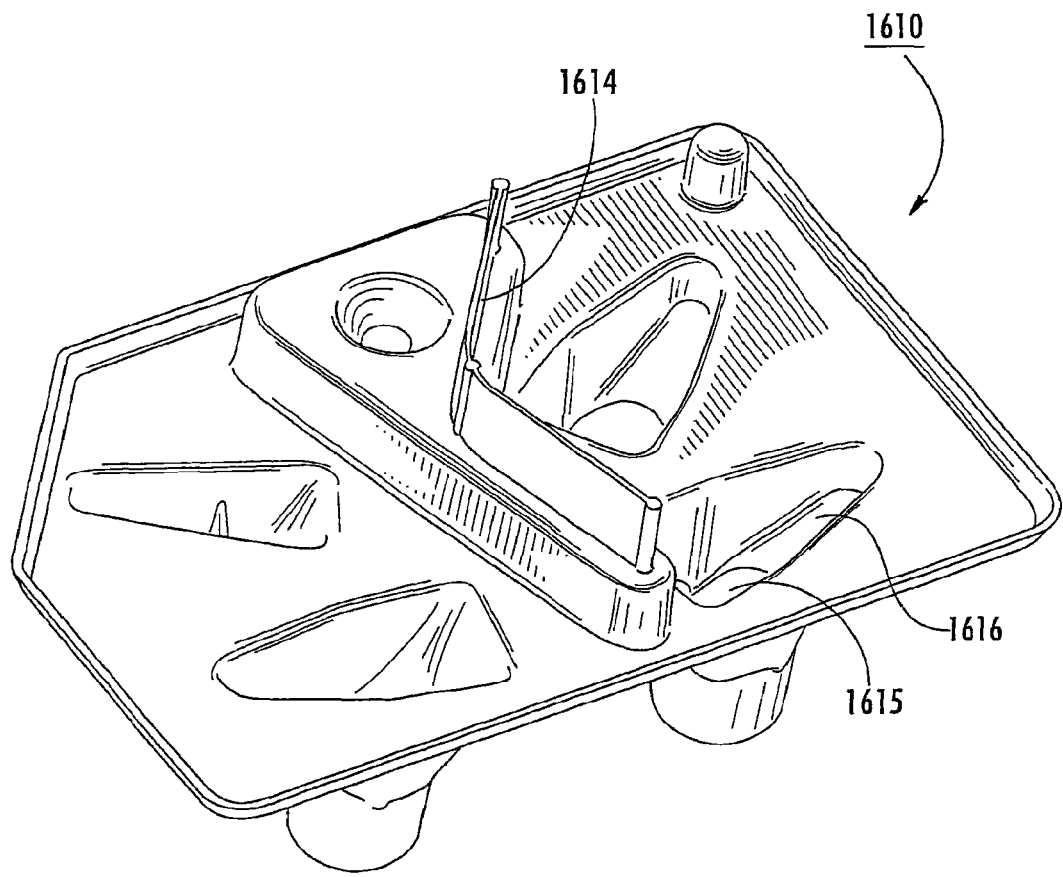
FIG. 29C is a top perspective view of the tray shown in FIG. 29A.

FIGS. 29A-29C show an exemplary elution tray 1610. As shown, the receptacles 1612 are spaced apart and angled to inhibit splash-over during use of a respective receptacle 1612. Two or more receptacles 1612 reside on each side of an upwardly extending barrier 1614 and the primary tubular receiving portion 1615 merges into a shallow channel 1616 that tapers downwardly and becomes deeper and narrower as it moves toward the tubular body portion 1615. The forward portion of the channel 1616 is also tapered inwardly and downwardly to capture splash and to direct the liquid to flow to the primary tubular portion 1615.

FIGS. 30A-30B illustrate a similar configuration for the waste tray cover 1640 but the tips 1632 of the receptacles are open or have apertures for draining the waste to the waste station 632 (FIG. 16).

Figure 31:
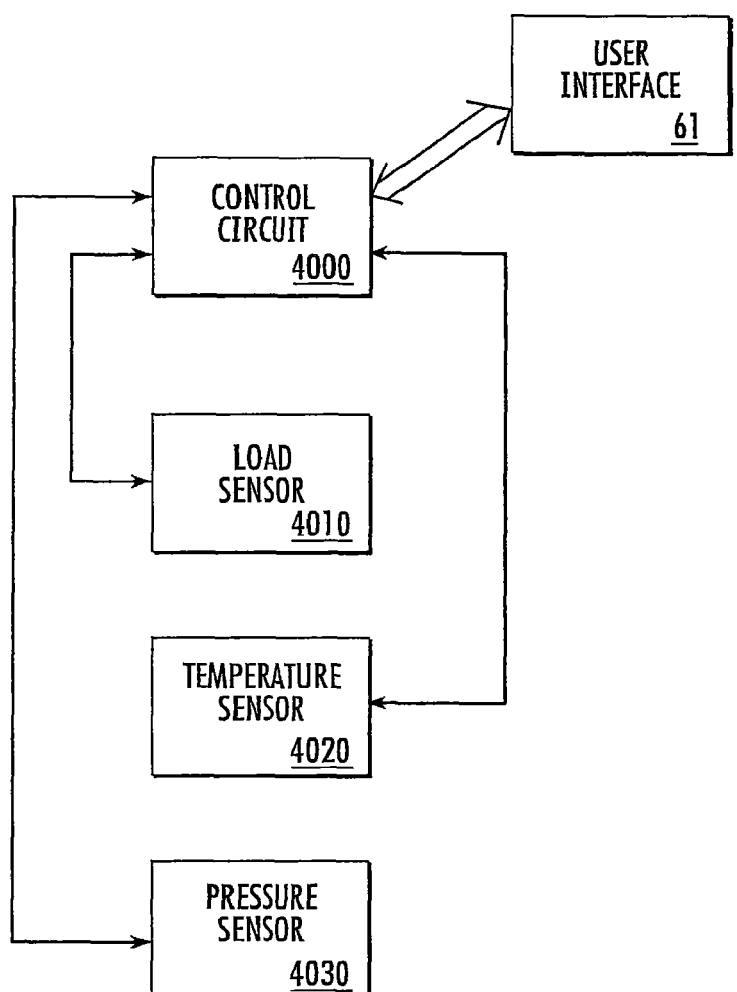
FIG. 31 is a block diagram of a circuit used in automated systems contemplated by the present invention.

FIG. 31 is a schematic illustration of a control circuit 4000 that is in communication with sensors 4010, 4020, 4030 that can be used to monitor the status of the inside of the container or provide desired feedback to allow the automatic control of components (heaters, coolers, robotic arm movement and the like). As shown, the control circuit 4000 can be in communication with the user interface 61 (FIG. 1). The sensors can include a load sensor 4010, a temperature sensor 4020, and a pressure sensor 4030. The load sensor 4010 can be in communication with the new pipette rack to provide loading force data used to control the engagement force applied by the robotic arm to engage a new pipette. The temperature sensor 4020 can provide temperature data regarding the internal environment or a particular location within the closed container environment (e.g., one or more of the workstations). The pressure sensor 4030 can be used to monitor the sealed integrity status of the closed environment and/or vacuum during isolation or purification procedures. Multiple sensors of each or some of the sensors can be used and other sensors may also be used. The control circuit 4000 may reside wholly or partially in the system 10 or wholly or partially with or on the container 12.

As will be appreciated by one of skill in the art, embodiments of the invention may be embodied as a method, system, data processing system, or computer program product. Accordingly, the present invention may take the form of an entirely software embodiment or an embodiment combining software and hardware aspects, all generally referred to herein as a "circuit" or "module." Furthermore, the present invention may take the form of or use a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic or other electronic storage devices.

Computer program code for carrying out operations of the present invention may be written in PLC code such as Graph, Ladder or SCL. However, the computer code can be alternatively or additionally written in an object oriented programming language such as Java, Smalltalk or C++ and/or conventional procedural programming languages, such as the "C" programming language or in a visually oriented programming environment, such as VisualBasic.

Certain portions (or all) of the program code may execute entirely on one or more of the system's computer(s), partly on the system computer(s), as a stand-alone software package, partly on the system computer(s) and partly on a remote computer or entirely on the remote computer. In the latter scenario, the remote computer may be connected to the system computer through a local area network (LAN) or a wide area network (WAN), or the connection may be made to an external computer (for example, through the Internet using an Internet Service Provider). In some embodiments, some program code may execute on local computers and some program code may execute on one or more local and/or remote server. The communication can be done in real time or near real time or off-line using a volume data set provided from the imaging modality.

The invention is described in part with reference to flowchart illustrations and/or block diagrams of methods, systems, computer program products and data and/or system architecture structures according to embodiments of the invention. It will be understood that each block of the illustrations, and/or combinations of blocks, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the block or blocks.

These computer program instructions may also be stored in a computer-readable memory or storage that can direct a computer or other programmable data processing apparatus to function in a particular manner, such that the instructions stored in the computer-readable memory or storage produce an article of manufacture including instruction means which implement the function/act specified in the block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the block or blocks.

Figure 32:
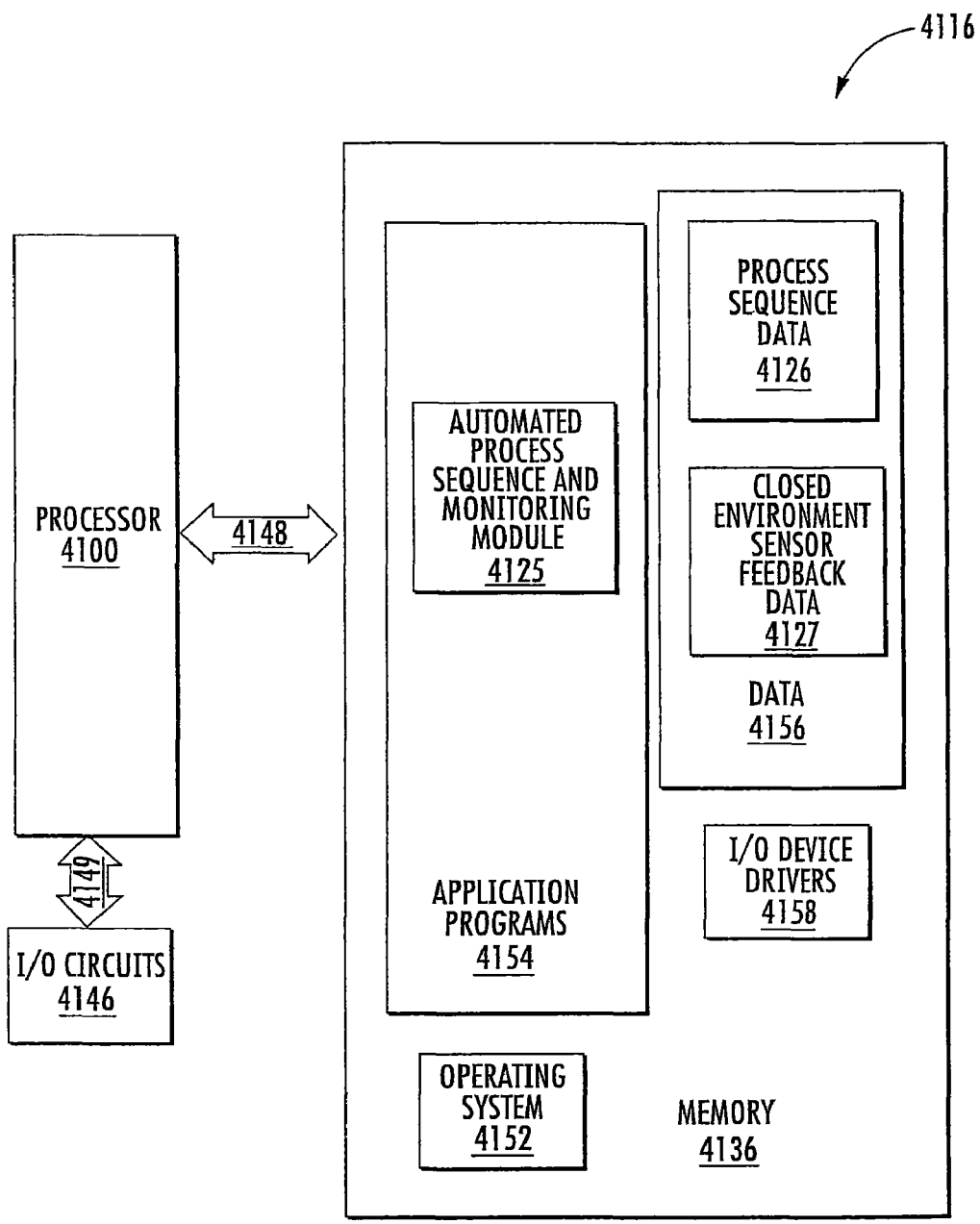
FIG. 32 is a block diagram of a data processing system according to embodiments of the present invention.

As illustrated in FIG. 32, embodiments of the invention may be configured as a data processing system 4116, which can be used to carry out or direct operations of the rendering, and can include a processor circuit 4100, a memory 4136 and input/output circuits 4146. The data processing system may be incorporated in, for example, one or more of a programmable logic controller (PLC), personal computer, workstation, server, router or the like. The system 4116 can reside on one machine or between a plurality of machines. The processor 4100 communicates with the memory 4136 via an address/data bus 4148 and communicates with the input/output circuits 4146 via an address/data bus 4149. The input/output circuits 4146 can be used to transfer information between the memory (memory and/or storage media) 4136 and another computer system or a network using, for example, an Internet protocol (IP) connection. These components may be conventional components such as those used in many conventional data processing systems, which may be configured to operate as described herein.

In particular, the processor 4100 can be commercially available or custom microprocessor, microcontroller, digital signal processor or the like. The memory 4136 may include any memory devices and/or storage media containing the software and data used to implement the functionality circuits or modules used in accordance with embodiments of the present invention. The memory 4136 can include, but is not limited to, the following types of devices: ROM, PROM, EPROM, EEPROM, flash memory, SRAM, DRAM and magnetic disk. In some embodiments of the present invention, the memory 4136 may be a content addressable memory (CAM).

As further illustrated in FIG. 32, the memory (and/or storage media) 4136 may include several categories of software and data used in the data processing system: an operating system 4152; application programs 4154; input/output device drivers 4158; and data 1456. As will be appreciated by those of skill in the art, the operating system 4152 may be any operating system suitable for use with a data processing system, such as IBM®, OS/2®, AIX® or zOS® operating systems or Microsoft® Windows®95, Windows98, Windows2000, WindowsXP or WindowsCE operating systems, Unix or Linux™. IBM, OS/2, AIX and zOS are trademarks of International Business Machines Corporation in the United States, other countries, or both while Linux is a trademark of Linus Torvalds in the United States, other countries, or both. Microsoft and Windows are trademarks of Microsoft Corporation in the United States, other countries, or both. The input/output device drivers 4158 typically include software routines accessed through the operating system 4152 by the application programs 4154 to communicate with devices such as the input/output circuits 4146 and certain memory 4136 components. The application programs 4154 are illustrative of the programs that implement the various features of the circuits and modules according to some embodiments of the present invention. Finally, the data 4156 represents the static and dynamic data used by the application programs 4154 the operating system 4152 the input/output device drivers 4158 and other software programs that may reside in the memory 4136.

The data 4156 may include (substantially real-time, archived or stored) Process Sequence data sets 4126 and/or closed environment sensor feedback data 4127. As further illustrated in FIG. 32, according to some embodiments of the present invention application programs 4154 include an Automated Process Sequence and Monitoring Module 4125. The application program 4154 may be located in a local server (or processor) and/or database or a remote server (or processor) and/or database, or combinations of local and remote databases and/or servers.

While the present invention is illustrated with reference to the application programs 4154 in FIG. 32, as will be appreciated by those of skill in the art, other configurations fall within the scope of the present invention. For example, rather than being application programs 4154, these circuits and modules may also be incorporated into the operating system 4152 or other such logical division of the data processing system. Furthermore, while the application program 4154 is illustrated in a single data processing system, as will be appreciated by those of skill in the art, such functionality may be distributed across one or more data processing systems in, for example, the type of client/server arrangement described above. Thus, the present invention should not be construed as limited to the configurations illustrated in FIG. 32, as it may be provided by other arrangements and/or divisions of functions between data processing systems. For example, although FIG. 32 is illustrated as having various circuits and modules, one or more of these circuits or modules may be combined or separated without departing from the scope of the present invention.

Other Embodiments

The foregoing exemplary system 10 was provided to illustrate various aspects and features of the present invention, and is not intended to limit the scope of the present invention to systems, devices and methods for nucleic acid processing. Rather, one skilled in the art will appreciate that various other applications fall within the scope of the present invention, including, for example, systems and methods for fabricating, assembling, processing or otherwise manipulating any items, typically in a closed container. The following sections provide additional examples of applications in which the apparatus and methods of the present invention may be employed.

Examples of Other Biological and/or Pharmaceutical Applications

In other aspects, the present invention provides methods of transferring a material, for example, a fluid, from a source to a target in a closed environment, wherein the closed environment is defined as the interior region or chamber in the container of an apparatus as described in the present application. A fluid to be transferred can contain, for example, a biologic; drug; toxin; isolate; radioisotope; virus; bacteria; eukaryotic cell; extract; analyte; biological specimen such as, for example, blood, plasma, saliva, etc.; vaccine; nucleic acid; protein; foodstuff; and the like, including suspensions, mixtures, and so on, thereof.

Applications for the instant systems and methods can be found, for example, where contamination of the material to be transferred inside the closed environment is to be avoided by substances potentially in the environment outside of container. In certain embodiments, the systems and methods can be directed to preparation of materials for, or for processing materials in, diagnostic assays, such as, by way of non-limiting examples, sterility assays, forensic analyses, or quality control assays, for example, to test purity of biologics to be used in clinical applications. In other embodiments, the instant methods can be for the preparation or manufacture of drugs and biologics, such as vaccines, and nucleic acids for experimental and/or clinical use. Various assays and methodologies that may be suitable for use in the systems and methods of the present invention are known to those of skill in the art as described, for example, in United States Pharmacopeia, *United States Pharmacopeia and National Formulary* (*USP 29-NF* 24) (2006), U.S. Department of Health and Human Services, *Guidance for Industry: Sterile Drug Products Produced by Aseptic Processing— Current Good Manufacturing Practice* (September 2004), each of which is incorporated by reference herein in its entirety.

It will be understood by those skilled in the art that a target to which a fluid is transferred can be any receptacle, such as, for example, a tube, vial, vessel, and the like, that is intended to hold the transferred fluid. In some embodiments, the target is a substrate, such as a binding column, size exclusion column, chromatography media, or filter, or the like. However, depending upon the particular application in the methods provided, any flow-through device, that is, any device intended to capture and/or separate and/or concentrate one or more components of the transferred fluid from another component of the fluid, can be used.

Figure 14:
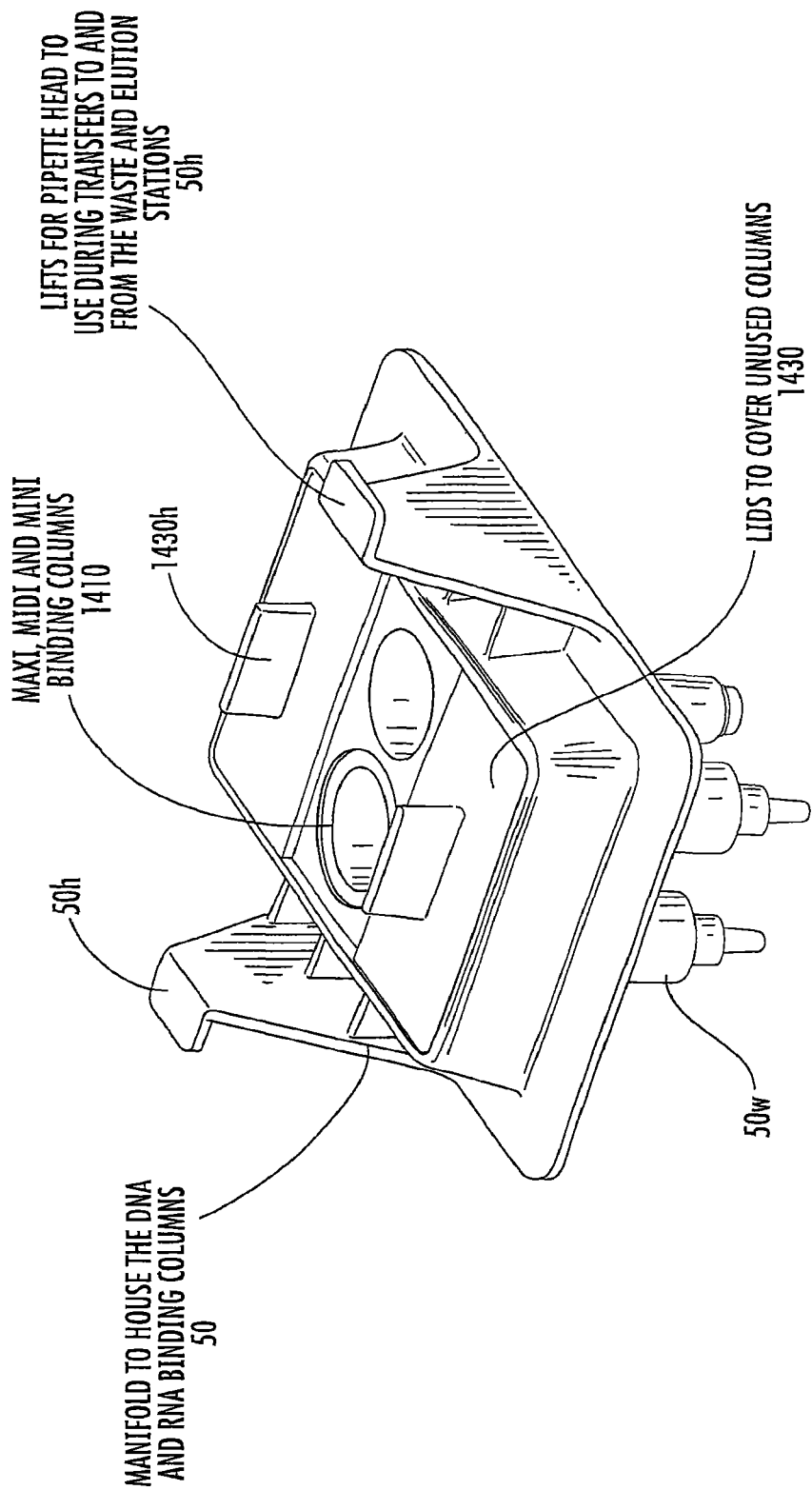
FIG. 14 is a perspective view of a manifold for housing DNA and RNA binding columns according to embodiments of the present invention.

FIG. 14 provides an example of a configuration of an exemplary apparatus wherein binding columns 1410 situated in the closed environment are a target for transferred fluid containing, for example, nucleic acids. In other embodiments, the manifold described in FIG. 14 can be adapted to fit filters or other devices discussed above.

In some embodiments, systems and methods provided by the invention can allow for aseptic preparation of an amplified nucleic acid product, comprising the steps of isolating RNA from a cell extract and amplifying a nucleic acid product from at least one RNA molecule from the isolated RNA, wherein the isolating and amplifying steps are performed in a closed environment as defined as the interior region or chamber in the container of an apparatus as described in the present application, thereby aseptically preparing the amplified nucleic acid product.

In certain embodiments for the aseptic preparation of an amplified nucleic acid product, the amplified nucleic acid product is derived from a pathogen, such as from a viral pathogen. In certain embodiments, the amplified nucleic acid product is derived from human tumor RNA. An amplified nucleic acid product from a human tumor RNA can be used, for example, in the preparation of a vaccine or immunotherapy.

The instant methods can be used for the sterilization of a material, for example, a biologic as defined under Title 21 of the United States Code of Federal Regulations, nucleic acid, and/or protein, and so forth, under aseptic conditions. Guidelines regarding the preparation of such materials for clinical applications are described in, e.g., U.S. Department of Health and Human Services, *Guidance for Industry: Sterile Drug Products Produced by Aseptic Processing— Current Good Manufacturing Practice* (September 2004).

Thus, in certain embodiments, methods are provided for the sterilization of a material comprising transferring a fluid comprising the material from a source to a filter and collecting the material after passage through the filter into a receptacle, wherein the source, filter and receptacle are contained in a closed environment as defined as the interior chamber or region in the container of an apparatus as described in the present application. Filters for sterilization are commercially available, for example, from Whatman Inc. (Florham Park, N.J.).

It will also be recognized that transferring material, for example, dispensing the material into a vial, can be hazardous if the material comprises a pathogen, such as is the HIV virus, or other certain microorganisms, or comprises a biological toxin or a radioactive substance. Transferring such materials into receptacles in a closed environment such as defined in embodiments of the present invention can be used to reduce the potential exposure of the hazardous material to the individuals undertaking the transfer. Thus, in certain embodiments, methods are provided wherein a hazardous material is transferred from a source to a target in a closed environment as in the container of an apparatus as described in the present application. These methods can be applied to a variety of procedures and assays where hazardous materials are transferred between a source and a target, as will be known to those of skill in the art.

The apparatus of the present invention can be used for other applications typical of protein purification, nucleic acid purification, and other molecular biology processes. Such applications include, but are not limited to, cell lysing (e.g., mechanical, chaotropic, thermal, or enzymatic lysing of cells), macromolecule purification (e.g., ion exchange, bead, molecular weight cutoff), and recovery (silica elution, bead elution, membrane elution).

Exemplary Lithography, Microfabrication and Related Applications

Embodiments of the present invention can be used in any situation where clean room conditions are used or isolation is desired, such as, for example, lithography and assembly processes. In some embodiments, the apparatus of the present invention satisfy the conditions of a class 1, class 10, class 100, class 1000, class 10,000, or class 100,000 clean room as set forth by the U.S. Federal Standard 209b for clean room classification. See, Federal Standard No. 209B 1992, "Clean Room and Work Station Requirements, Controlled Environment," dated Apr. 24, 1973, which is hereby incorporated by reference in its entirety. As such, embodiments of the present invention can be used for a broad spectrum of processes that use a clean room environment. Such processes include lithography processes such as, but not limited to, wafer patterning (also known as photomasking, masking, photolithography, microlithography), doping (e.g., thermal diffusion, ion implantation), heat treatment (e.g., thermal, radiation). Specific patterning processes that can be conducted in the apparatus of the present invention include, but are not limited to (i) resist application (positive or negative); (ii) exposure (e.g. by contact, proximity, scanning projection, and stepper) to high pressure mercury, X-rays, or E-beams; (iii) imaging (e.g., single layer resist, multilayer resist, application of antireflector layers, off-axis illumination, planarization, contrast enhancement; and (iv) etch (e.g., wet chemistry-liquid/vapor, dry, plasma, lift-off, ion milling, reactive ion etching. Specific heat treatment processes include, but are not limited to, hot plate, convection, rapid thermal processing (RTP), and infrared. More description of these lithography processes are described in Van Zant, *Microchip Fabrication*, Fourth Edition, Chapter 4, 2000, McGraw-Hill, New York, which is hereby incorporated by reference in its entirety.

In addition to conventional lithographic techniques, the apparatus of the present invention can be used to house next-generation lithographies such as extreme ultraviolet lithography, X-ray lithography (e.g., LIGA), charged-particle-beam lithography (e.g., electron-beam, ion-beam), scanning probe lithography (e.g., scanning tunneling microscope lithography, atomic force microscope lithography, scanning electrochemical microscope lithography), soft lithography (e.g., replica mold, micro-contact printing, micro-molding in capillaries, micro-transfer molding, solvent-assisted micromolding, near-field conformal photolithography using an elastomeric phase-shifting mask) and three-dimensional lithography (e.g., holographic lithography, lithography on non-planar substrates). Such techniques are described in Madou, *Fundamentals of Microfabrication*, Second Edition, 2002, CRC Press LLC Boca Raton, Fla., pp. 48-68, which is hereby incorporated herein by reference in its entirety.

Embodiments of the present invention can be used for protein patterning microlithographic techniques that address, for example, the problem of non-specific protein absorption competing for detection sites in immunosensors. See, for example, Clementi et al., *Structure and Motion: Membranes, Nucleic Acids, and Proteins*, Adenine Press, Schenectady, N.Y., 1985, which is hereby incorporated herein by reference in its entirety.

Devices, systems, apparatus and methods of the present invention can be used to perform dry etching techniques such as physical etching (e.g., ion etching, sputtering, ion-beam milling), plasma etching (e.g., radical etching), physical/chemical etching, deep reactive ion etching, vapor-phase etching without plasma, dry etching, and single-crystal reactive etching metallization (SCREAM) as disclosed in Chapter 2 of Madou *Fundamentals of Microfabrication*, Second Edition, 2002, CRC Press LLC Boca Raton, Fla., which is hereby incorporated herein by reference in its entirety.

The apparatus of the present invention can be used to perform pattern transfer with additive techniques such as silicon growth, doping of silicon, oxidation of silicon, physical vapor diffusion (e.g., thermal evaporation, sputtering, molecular beam epitaxy, laser sputter deposition, ablation deposition, ion plating, cluster beam technology), chemical vapor deposition, silk-screening (screen printing), sol-gel deposition, plasma spraying, spray pyrolysis, and plasma-beam deposition as disclosed in Chapter 3 of Madou *Fundamentals of Microfabrication*, Second Edition, 2002, CRC Press LLC Boca Raton, Fla., which is hereby incorporated herein by reference in its entirety.

Embodiments of the present invention may be particularly useful in deposition and arraying methods used in the BIOMEMS field, which encompasses techniques for depositing organic materials for chemical and biological sensors, often arranged in some type of array configuration. Such techniques can be used, for example, to make organic gas permeable membranes, ion selective membranes, hydrogels, organic monolayers needed for room-temperature gas sensors, ion selective electrodes, enzyme sensors, immunosensors, and DNA and protein arrays. Specific techniques in the BIOMEMS field that can be implemented on the apparatus of the present invention are spin coating, dip coating, plastic spraying, casting, type casting, glow discharge (plasma) polymerization, Langmuir-Blogett processes, ink-jetting, microspotting, and mechanical microspotting, as disclosed in Madou *Fundamentals of Microfabrication*, Second Edition, pp. 159-167, 2002, CRC Press LLC Boca Raton, Fla., which is hereby incorporated herein by reference in its entirety.

Embodiments of the present invention can be used for other clean room applications, such as packaging of small devices (e.g., integrated circuits). Specific packaging techniques that can be performed using the apparatus of the present invention include, but are not limited to, packaging of integrated circuits, dicing, cavity sealing and bonding, multi-chip packaging, and partitioning as disclosed in Madou *Fundamentals of Microfabrication*, Second Edition, pp. 478-508, 2002, CRC Press LLC Boca Raton, Fla., which is hereby incorporated herein by reference in its entirety.

Embodiments of the present invention can be used for application of photoresists in lithographic processes. For instance, the apparatus of the present invention can be used to apply either positive or negative photoresist to a substrate in a clean room environment. As such, steps such as resist spin coating, softbake, hardbake, development, post-exposure bake, and multi-layer resists processes can be performed in the apparatus of the present invention as described in Levinson, *Principles of Lithography*, SPIE Press, Bellingham, Wash., 2001, Chapter 3, which is hereby incorporated herein by reference in its entirety. The apparatus of the present invention can be used for lithographic processes such as optical lithography, electron beam lithography, x-ray lithography, deep-UV resist application, photomask fabrication, as well as metrology methods in photolithography as described in *Microlithography, Micromachining, and Microfabrication*, ed. Rai-Choudhury, SPIE Press, Bellingham, Wash., 2001, Chapters 1-6, which is hereby incorporated herein by reference in its entirety. The systems, devices, apparatus and methods of the present invention can further be used to implement methods used to fabricate photovoltaic cells, including but not limited to phosphorous diffusion, edge isolation, ARC deposition, front-contact printing, back-contact printing, co-firing, testing and sorting, as disclosed in *Handbook of Photovoltaic Science and Engineering*, Luque and Gegedu eds., John Wiley & Sons, West Sussex, England, 2003, pp. 271-279, which is hereby incorporated herein by reference in its entirety.

All references cited herein are incorporated herein by reference in their entirety to the same extent as if each individual publication or patent or patent application was specifically and individually indicated to be incorporated by reference in its entirety. However, the incorporated by reference documents are not to be used to narrow an interpretation of a claim element of the pending application or any patent issuing thereon.

While the foregoing description and drawings represent embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. The presently disclosed embodiments are therefore to be considered in all respects as illustrative and not restrictive, the scope of the invention being indicated by the appended claims, and not limited to the foregoing description.

What is claimed is:

1. A method of processing biological samples, comprising:
   providing a closed processing system comprising a container assembly comprising a first member having a substantially rigid body and a flexible barrier member sealably attached to the first member to define an internal chamber, wherein the flexible barrier member is substantially impermeable, and wherein a plurality of flexible conduits are in fluid communication with the internal chamber and extend outward from the first member;
   processing a biological sample in the internal chamber while the flexible barrier remains sealably attached to the first member, wherein the flexible barrier can move up and down during the processing; and
   automatically directing a pump in communication with at least one of the plurality of flexible conduits to flow at least one amount of the processed biological sample out of the internal chamber through at least one of the flexible conduits to at least one aliquot vessel without disrupting a sealed state of the closed processing system.

2. The method of claim 1, further comprising automatically directing an external robotic arm to move a pipette tube inside the internal chamber under the flexible barrier between processing stations while moving the flexible barrier up and down.

3. The method of claim 1, wherein the container assembly comprises a plurality of upright spaced apart liquid vessels in the internal chamber, and wherein the method comprises automatically directing the pipette tube to move back and forth between a plurality of the liquid vessels during the processing.

4. The method of claim 1, wherein the processing further comprises programmatically directing a robotic arm to cooperate with the flexible barrier to move an interface tool inside the closed container assembly through a series of operations while the flexible barrier remains sealably attached to the first member.

5. The method of claim 1, wherein the processing comprises automatically measuring volume and concentration of the biological sample at a plurality of times during an amplification procedure.

6. The method of claim 1, further comprising electronically automatically monitoring seal integrity of the closed container assembly during the processing.

7. The method of claim 1, further comprising cooling a wall segment of the first member to provide a condensation wall inside the internal chamber during the processing.

8. The method of claim 1, wherein the internal chamber comprises a PCR plate, a pipette rack with pipette tips, and a tray of sealed reagent vessels.

9. The method of claim 1, wherein the processing comprises automatically directing one or more pipette tips to enter different liquid vessels in the internal chamber for mixing and/or withdrawing liquid.

10. The method of claim 1, wherein the processing comprises directing a robotic arm to move a pipette tip adapter held in or under the flexible barrier to releasably engage different pipette tips stored within the internal chamber.

11. The method of claim 1, wherein the flexible barrier member has a center portion that merges into an outer perimeter portion, and wherein the center portion Of the flexible barrier member can move relative to the outer perimeter portion, and wherein, during the processing, the center portion is able to translate in three dimensions and change in shape while the outer perimeter portion remains sealably attached to the first member.

12. The method of claim 11, wherein, during the processing, the flexible barrier travels between about 4-24 inches in a vertical direction.

13. The method of claim 11, wherein the biological sample comprises nucleic acid samples in the sealed chamber, and wherein during the processing the nucleic acid samples are processed at a plurality of spaced apart processing stations in the internal chamber.

14. The method of claim 11, further comprising at least one of a nucleic acid binding column or magnetic bead mixing vessel in the internal chamber.

15. The method of claim 1, wherein the biological sample comprises nucleic acid samples, wherein a manipulation tool is attached to a center portion of the flexible barrier, and wherein the internal chamber comprises a PCR plate, reagents, and sterile pipettes used during the processing to process the nucleic acid samples.

16. The method of claim 1, wherein the internal chamber comprises magnetic beads for purifying the biological sample.

17. The method of claim 1, wherein the biological sample is a patient sample, and wherein the processed sample in the at least one aliquot vessel is provided as a therapy to the patient.

18. The method of claim 1, further comprising heating a thermal input in thermal communication with at least one processing station in the internal chamber during the processing.

* * * * *

UNITED STATES PATENT AND TRADEMARK OFFICE
CERTIFICATE OF CORRECTION

PATENT NO. : 9,638,707 B2  
APPLICATION NO. : 15/357347  
DATED : May 2, 2017  
INVENTOR(S) : Spence et al.

Page 1 of 1

It is certified that error appears in the above-identified patent and that said Letters Patent is hereby corrected as shown below:

In the Claims

Column 38, Claim 11, Line 27: Please correct "center portion Of the" to read -- center portion of the --

Signed and Sealed this  
Sixth Day of March, 2018

Andrei Iancu  
*Director of the United States Patent and Trademark Office*